(12) United States Patent
Henderson et al.

(10) Patent No.: US 10,983,226 B2
(45) Date of Patent: Apr. 20, 2021

(54) ELECTRONIC DEVICES AND RELATED METHODS

(71) Applicants: Xan Henderson, Mesa, AZ (US); Michael Marrs, Phoenix, AZ (US)

(72) Inventors: Xan Henderson, Mesa, AZ (US); Michael Marrs, Phoenix, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 191 days.

(21) Appl. No.: 16/220,926

(22) Filed: Dec. 14, 2018

(65) Prior Publication Data

US 2019/0137635 A1 May 9, 2019

Related U.S. Application Data

(63) Continuation of application No. PCT/US2017/037882, filed on Jun. 16, 2017.

(60) Provisional application No. 62/351,171, filed on Jun. 16, 2016.

(51) Int. Cl.
  *G01T 1/20* (2006.01)
  *A61B 6/00* (2006.01)
  *H01L 27/146* (2006.01)

(52) U.S. Cl.
  CPC .......... *G01T 1/2018* (2013.01); *A61B 6/4233* (2013.01); *G01T 1/2006* (2013.01); *H01L 27/14658* (2013.01)

(58) Field of Classification Search
  CPC .............. G01T 1/2018; G01T 1/2006; H01L 27/14658; A61B 6/4233
  See application file for complete search history.

(56) References Cited

U.S. PATENT DOCUMENTS

| | | |
|---|---|---|
| 8,383,520 B2 | 2/2013 | Marrs |
| 8,999,778 B2 | 4/2015 | O'Rourke et al. |
| 9,601,530 B2 | 3/2017 | Marrs |
| 9,721,825 B2 | 8/2017 | Marrs et al. |
| 9,953,951 B2 | 4/2018 | Howard et al. |
| 9,991,311 B2 | 6/2018 | Smith et al. |
| 2009/0146070 A1* | 6/2009 | Vieira Da Rocha ........ H04N 3/1568 250/370.09 |

(Continued)

FOREIGN PATENT DOCUMENTS

| | | |
|---|---|---|
| TW | 201117262 A1 | 5/2011 |
| TW | 201611140 A | 3/2016 |

(Continued)

OTHER PUBLICATIONS

International Search Report and Written Opinion for PCT/US2017/037882, dated Dec. 5, 2017.

*Primary Examiner* — David P Porta
*Assistant Examiner* — Fani Boosalis
(74) *Attorney, Agent, or Firm* — Bryan Cave Leighton Paisner LLP

(57) ABSTRACT

Some embodiments include an electronic device. The electronic device includes a first scintillator layer, a transistor, and one or more device elements over the transistor, and the one or more device elements include a photodetector. Meanwhile, the first scintillator layer is monolithically integrated with at least one of the transistor or the one or more device elements. Other embodiments of related systems, devices, and methods are also disclosed.

20 Claims, 37 Drawing Sheets

(56) References Cited

U.S. PATENT DOCUMENTS

| | | |
|---|---|---|
| 2009/0166546 A1* | 7/2009 | Fleischmann ......... G01T 1/2018 |
| | | 250/370.11 |
| 2010/0127279 A1 | 5/2010 | Takahashi |
| 2010/0320391 A1 | 12/2010 | Antonuk |
| 2011/0227203 A1 | 9/2011 | Marrs et al. |
| 2012/0043468 A1 | 2/2012 | Flitsch et al. |
| 2013/0082264 A1 | 4/2013 | Couture et al. |
| 2014/0008651 A1 | 1/2014 | Marrs |
| 2018/0286912 A1 | 10/2018 | Smith et al. |
| 2020/0144314 A1* | 5/2020 | Ganguly ............. H01L 27/1469 |

FOREIGN PATENT DOCUMENTS

| | | |
|---|---|---|
| WO | 2010065457 A2 | 6/2010 |
| WO | 2010065459 A2 | 6/2010 |
| WO | 2010138811 A2 | 12/2010 |
| WO | 2012138903 A2 | 10/2012 |
| WO | 2014039693 A1 | 3/2014 |
| WO | 2014039698 A1 | 3/2014 |
| WO | 2015057719 A1 | 4/2015 |
| WO | 2015175353 A1 | 11/2015 |
| WO | 2016025463 | 2/2016 |

\* cited by examiner

ELECTRONIC DEVICES AND RELATED METHODS

CROSS-REFERENCE TO RELATED APPLICATIONS

This application is a continuation of International Application No. PCT/US17/37882, filed Jun. 16, 2017, which claims the benefit of U.S. Provisional Patent Application No. 62/351,171, filed Jun. 16, 2016. International Application No. PCT/US17/37882, and U.S. Provisional Patent Application No. 62/351,171 are incorporated herein by reference in their entirety.

STATEMENT REGARDING FEDERALLY SPONSORED RESEARCH OR DEVELOPMENT

This invention was made with government support under W911NF-04-2-0005 awarded by the Army Research Office. The government has certain rights in the invention.

FIELD OF THE INVENTION

This invention relates generally to electronic devices, and relates more particularly to electronic devices having one or more processed and/or integrated scintillator layers and methods of manufacturing the same.

DESCRIPTION OF THE BACKGROUND

An increasing demand exists for imaging systems (e.g., radiography systems). For example, as the average age of the world's population increases, the need for medical imaging systems is expected to rise dramatically. Meanwhile, imaging systems are also increasingly being used in non-medical applications, such as, for example, for security applications (e.g., transportation security) and/or engineering applications. In an exemplary engineering application, imaging systems may be used to conduct non-destructive testing for integrity analysis of a structure (e.g., a pipe, an airframe, an airfoil, etc.) in order to identify micro-cracks and crack initiation in the structure.

Conventional imaging systems, which may be based on rigid substrates, may be unsuitable for performing imaging (i) in remote locations, such as, for example, in less developed countries, and/or (ii) in restricted (e.g., confined) spaces. For example, conventional imaging systems may be insufficiently portable (e.g., by size, volume, and/or weight), flexible, and/or durable to perform imaging under such circumstances. Nonetheless, medical personnel (e.g., first responders), military personnel, security personnel, etc. may find it desirable and/or advantageous to perform imaging under these circumstances.

Accordingly, a need or potential for benefit exists for portable, flexible, and/or durable imaging systems and methods of manufacturing the same.

BRIEF DESCRIPTION OF THE DRAWINGS

To facilitate further description of the embodiments, the following drawings are provided in which.

Figure 1:
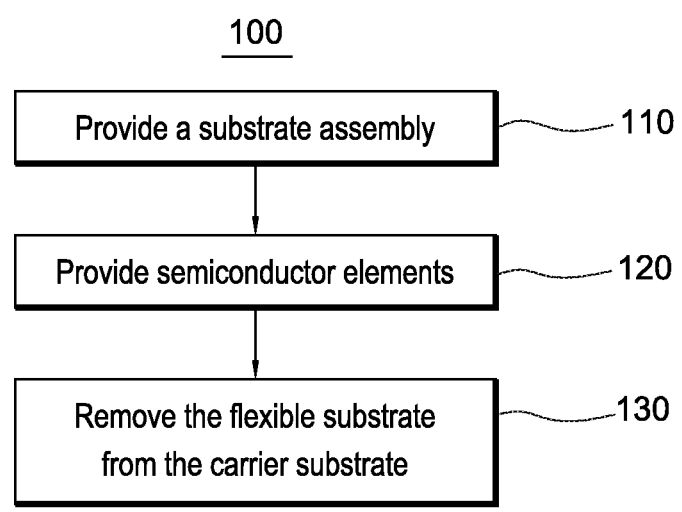
FIG. 1 illustrates an example of a method of providing a semiconductor device, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that an activity, method, system, article, device, or apparatus that comprises a list of elements is not necessarily limited to those elements, but may include other elements not expressly listed or inherent to such activity, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

The terms "bow" and/or "bowing" as used herein can mean the curvature of a layer and/or multiple layers about a median plane, which is parallel to the top and bottom sides, or major (e.g., outermost) surfaces of the layer and/or layer(s). The term "warping" as used herein can mean the linear displacement of the surface of a layer and/or multiple layers with respect to a z-axis, which is perpendicular to the top and bottom sides, or major (e.g., outermost) surfaces of the layer and/or layer(s). The term "distortion" as used herein can mean the displacement of a layer and/or multiple layers in-plane (i.e., the x-y plane, which is parallel to the top and bottom sides, or major (e.g., outermost) surfaces of the layer and/or layer(s)). For example, distortion could include shrinkage in the x-y plane of a layer and/or multiple layers and/or expansion in the x-y plane of the layer and/or layer(s).

The term "CTE matched material" as used herein can mean a material that has a coefficient of thermal expansion (CTE) which differs from the CTE of a reference material by less than about 20 percent (%). Preferably, the CTEs differ by less than about 10%, 5%, 3%, or 1%. As used herein, "polish" can mean to lap and polish a surface or to only lap the surface.

The term "flexible substrate" as used herein means a free-standing substrate that readily adapts its shape. Accordingly, in many embodiments, the flexible substrate can comprise (e.g., consist of) a flexible material, and/or can comprise a thickness (e.g., an average thickness) that is sufficiently thin so that the substrate readily adapts in shape. In these or other embodiments, a flexible material can refer to a material having a low elastic modulus. Further, a low elastic modulus can refer to an elastic modulus of less than approximately five GigaPascals (GPa). In some embodiments, a substrate that is a flexible substrate because it is sufficiently thin so that it readily adapts in shape, may not be a flexible substrate if implemented with a greater thickness, and/or the substrate may have an elastic modulus exceeding five GPa. For example, the elastic modulus could be greater than or equal to approximately five GPa but less than or equal to approximately twenty GPa, fifty GPa, seventy GPa, or eighty GPa. Exemplary materials for a substrate that is a flexible substrate because it is sufficiently thin so that it readily adapts in shape, but that may not be a flexible substrate if implemented with a greater thickness, can comprise certain glasses (e.g., fluorosilicate glass, borosilicate glass, Corning® glass, Willow™ glass, and/or Vitrelle glass, etc., such as, for example, as manufactured by Corning Inc. of Corning, N.Y., United States of America, etc.) or silicon having a thickness greater than or equal to approximately 25 micrometers and less than or equal to approximately 100 micrometers.

Meanwhile, the term "rigid substrate" as used herein can mean a free-standing substrate that does not readily adapt its shape and/or a substrate that is not a flexible substrate. In some embodiments, the rigid substrate can be devoid of flexible material and/or can comprise a material having an elastic modulus greater than the elastic modulus of a flexible substrate. In various embodiments, the rigid substrate can be implemented with a thickness that is sufficiently thick so that the substrate does not readily adapt its shape. In these or other examples, the increase in rigidity of the rigid substrate provided by increasing the thickness of the rigid substrate can be balanced against the increase in cost and weight provided by increasing the thickness of the rigid substrate.

As used herein, "polish" can mean to lap and polish a surface or to only lap the surface.

DETAILED DESCRIPTION OF EXAMPLES OF EMBODIMENTS

Some embodiments include an electronic device. The electronic device can comprise a first scintillator layer, a transistor, and one or more device elements over the transistor, and the one or more device elements can comprise a photodetector. Meanwhile, the first scintillator layer can be monolithically integrated with at least one of the transistor or the one or more device elements.

Further embodiments include a method of manufacturing an electronic device. The method can comprise: providing a first scintillator layer; providing a transistor; and providing one or more device elements over the transistor. Providing the one or more device elements can comprise providing a photodetector. Meanwhile, the first scintillator layer is monolithically integrated with at least one of the transistor or the one or more device elements.

Further embodiments include an electronic device. The electronic device can comprise a substrate assembly, and the substrate assembly can comprise a carrier substrate and a flexible substrate coupled to the carrier substrate. Further, the electronic device can comprise a transistor over the substrate assembly, one or more device elements over the transistor, and a first scintillator layer over the one or more device elements. Meanwhile, the one or more device elements can comprise a photodetector, and the first scintillator layer can comprise one or more first radiation absorbing materials and one or more first phosphorescent materials. The first scintillator layer can directly contact the photodetector, and the first scintillator layer can be monolithically integrated with the transistor and the photodetector.

Turning to the drawings, FIG. 1 illustrates an example of method 100 of providing a semiconductor device, according to an embodiment. In the same or different embodiments, method 100 can be considered a method of providing a thin film transistor on a flexible substrate. Method 100 is merely exemplary and is not limited to the embodiments presented herein. Method 100 can be employed in many different embodiments or examples not specifically depicted or described herein.

Figure 2:
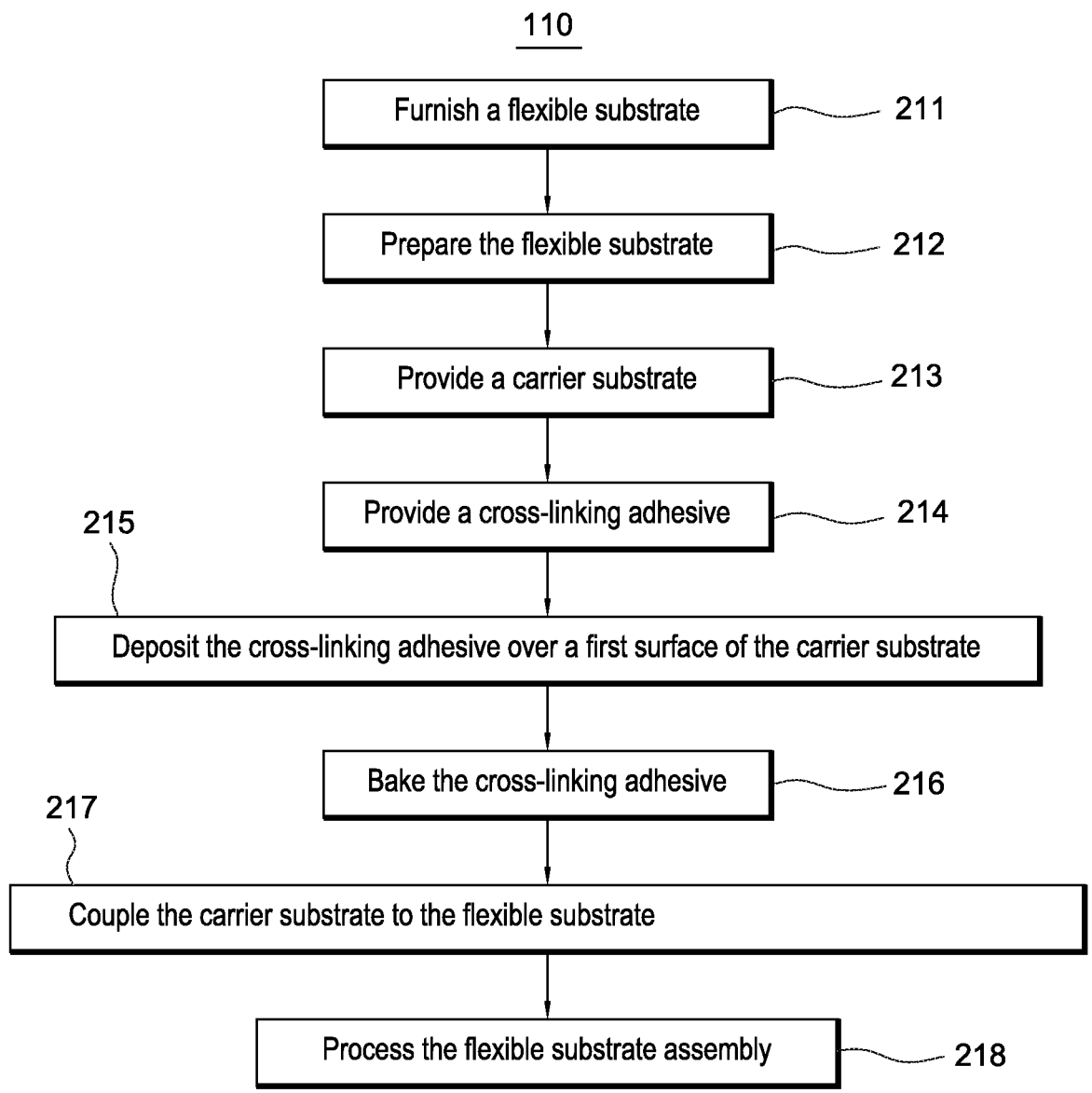
FIG. 2 illustrates an example is an activity of providing a substrate assembly, according to the embodiment of FIG. 1.

Method 100 comprises activity 110 of providing a substrate assembly. In some embodiments, the substrate assembly can comprise a flexible substrate. In other embodiments, the substrate assembly may be devoid of a flexible substrate, such as, for example, where the substrate assembly comprises a rigid substrate but not a flexible substrate. FIG. 2 is a flow chart illustrating activity 110 of providing the substrate assembly, according to the embodiment of FIG. 1. Where the substrate assembly comprises a rigid substrate but not a flexible substrate, activities 211, 212, and 214-218, as described below, can be omitted. In these examples, the rigid substrate can comprise the carrier substrate, as described below with respect to activity 213.

Activity 110 can comprise activity 211 of furnishing a flexible substrate. In some embodiments, the flexible substrate can comprise a plastic substrate. The flexible substrate can comprise any suitable material(s) having the characteristics of a flexible substrate as defined above. In many embodiments, exemplary material(s) of the flexible substrate can comprise polyethylene naphthalate (PEN), polyethylene terephthalate (PET), polyethersulfone (PES), polyimide, polycarbonate, cyclic olefin copolymer, liquid crystal polymer, any other suitable polymer, glass (e.g., fluorosilicate glass, borosilicate glass, Corning® glass, Willow™ glass, and/or Vitrelle glass, etc., such as, for example, as manufactured by Corning Inc. of Corning, N.Y., United States of America, etc.), metal foil (e.g., aluminum foil, etc.), etc.

In many examples, the flexible substrate can comprise a coating at one or more sides of the flexible substrate. The coating can improve the scratch resistance of the flexible substrate and/or help prevent outgassing or oligomer crystallization on the surface of the substrate. Moreover, the coating can planarize the side of the flexible substrate over which it is located. The coating also can help decrease distortion. In some examples, the coating can be located only at the side of the flexible substrate where the electrical device will be fabricated. In other examples, the coating can be at both sides of the flexible substrate. In various embodiments the flexible substrate can be provided pre-planarized. For example, the flexible substrate can comprise a PEN substrate from DuPont Teijin Films of Tokyo, Japan, sold under the tradename "planarized Teonex® Q65." In other embodiments, a flexible substrate can be planarized after being provided. For example, method 2700 (FIG. 27) provides a method of planarizing a flexible substrate.

The thickness of the flexible substrate can be in the range of approximately 25 micrometers (μm) to approximately 300 μm. In the same or different embodiments, the thickness of the flexible substrate can be in the range of approximately 100 μm to approximately 200 μm.

In some examples, the flexible substrate can be provided by cutting a sheet of a plastic substrate from a roll of the plastic material using a paper cutter or a pair of ceramic scissors. In various examples, after cutting the plastic substrate, the cut sheet can be blown clean with a nitrogen gun. In some embodiments of activity 110, either or both of the cutting and blowing activities can be part of an activity 212, described below, instead of being part of activity 211.

Figure 3:
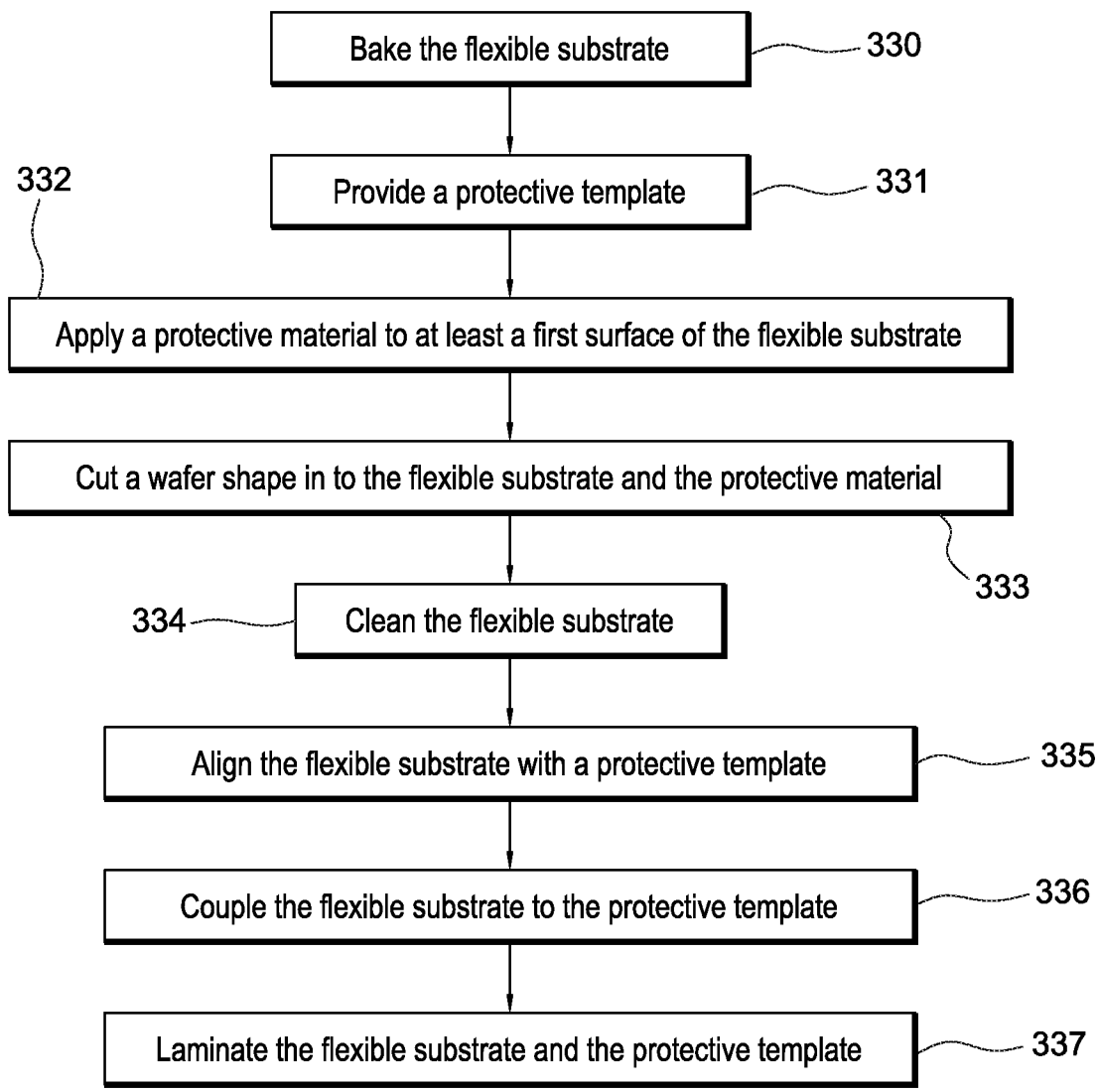
FIG. 3 illustrates an example of an activity of preparing a flexible substrate, according to the embodiment of FIG. 1.

In many embodiments, activity 110 can comprise activity 212 of preparing the flexible substrate. FIG. 3 is a flow chart illustrating activity 212 of preparing the flexible substrate, according to the embodiment of FIG. 1.

In some embodiments, activity 212 can comprise activity 330 of baking the flexible substrate. Baking the flexible substrate can help release oligomers and other chemicals in the flexible substrate that could potentially leach out later during method 100 (FIG. 1).

In some examples, the flexible substrate can be baked using a vacuum bake activity. For example, the temperature in an oven containing the flexible substrate can be ramped up over approximately two to three hours to approximately 160 degrees Celsius (° C.) to approximately 200° C. The flexible substrate can be baked for one hour at approximately 160° C. to approximately 200° C. and at a pressure of approximately one milliTorr (mTorr) to approximately ten mTorr. Then, the temperature in the oven can be lowered to between approximately 90° C. to approximately 115° C., and the flexible substrate can be baked for approximately eight more hours. Other baking activities can be also be used. After the baking activity is complete, the flexible substrate can be wiped clean of any residues or chemicals that were baked off.

In some embodiments, activity 212 can comprise activity 331 of providing a protective template. The protective template can act as both a guide for the placement of the flexible substrate as well as a protective layer between the flexible substrate and the rollers and/or handling mechanisms of various processing equipment. In some examples, the protective template can comprise a sheet of mylar or any inexpensive plastic. In other embodiments, the protective template can comprise tape (e.g., a low tack tape). In these embodiments, one or more of activity 332-335 and activity 337, as described below, can be omitted.

The protective template can be 50 μm to 15 mm thick and cut to a length of approximately 0.5 m (meters) to approximately 1.5 m. In various embodiments, as part of activity 331, the protective template can be folded in half and run through rollers (e.g., a hot roll laminator) to help lock in the fold. A line trace of a carrier substrate can also be made on the back side of the protective sheet as part of activity 331. Additionally, the protective template can be baked at approximately 90° C. to approximately 110° C. for approximately five minutes to approximately ten minutes to help flatten the protective template.

In some embodiments, activity 212 can comprise activity 332 of applying a protective material to at least a portion of a first surface of the flexible substrate. In some embodiments, a protective material can be applied over at least a portion of a planarized surface of the flexible substrate. In some examples, the protective material is not applied to a portion of the flexible substrate.

The protective material can prevent scratches and adhesive from covering the planarized surface of the flexible substrate and, thus, reduces defects. In some examples, blue low tack tape (e.g., from Semiconductor Equipment Corporation, part number 18133-7.50) or mylar could be used as the protective material. The protective material can be approximately 25 μm to approximately 100 μm thick. For example, the protective material can be approximately 70 μm thick. In some examples, the protective material is applied by rolling the protective material onto the planarized surface of the flexible substrate using a roller to remove air bubbles between the protective material and the flexible substrate.

In some embodiments, activity 212 can comprise activity 333 of cutting the flexible substrate and protective material into the shape of a wafer. A punch cut template can be used to press the wafer shape into the flexible substrate (with the planarized side, if any, up) and/or the protective material. In one embodiment, the punch cut template can be used to create a temporary or permanent impression in the protective material and the flexible substrate at the same time.

If the pressing of the punch cut template cuts completely through the flexible substrate, the flexible substrate can be scrapped because the press cut can create cracks in a coating on the flexible substrate that propagate throughout the flexible substrate. After the wafer shape is outlined into the flexible substrate and/or the protective material using the press, the flexible substrate and the protective material can be cut simultaneously with each other. In some examples, the flexible substrate and protective material can be cut using ceramic scissors approximately one millimeter outside the impression made by the punch cut template.

Figure 4:
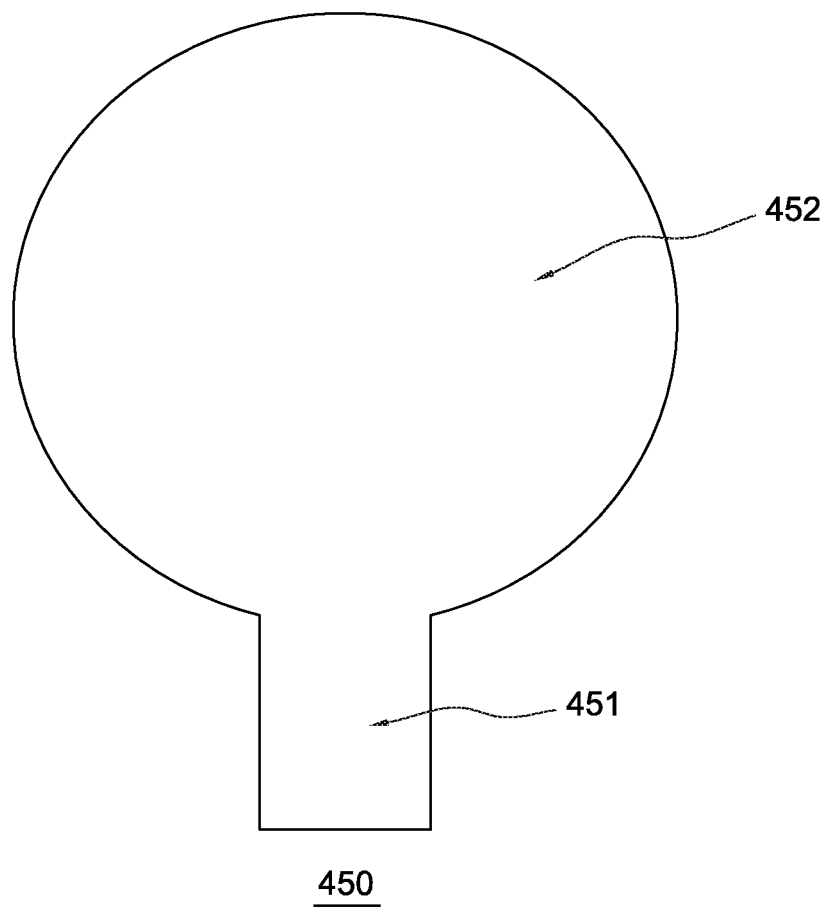
FIG. 4 illustrates a top view of an example of the flexible substrate of FIG. 3, according to the embodiment of FIG. 1.

In some examples, the flexible substrate can comprise a tab extending from the wafer shape in the flexible substrate and the protective material. The tab can be used to help align the flexible substrate to a carrier substrate when traveling through a laminator in activity 217 (FIG. 2). FIG. 4 illustrates a top view of flexible substrate 450, according to the embodiment of FIG. 1. Flexible substrate 450 can comprise body 452 and tab 451. In many examples, body 452 can have a circular shape. Although not illustrated in FIG. 4, the protective material that is located over flexible substrate 450 can also comprise a similarly shaped tab. In one embodiment, the tab is not part of the punch cut template and is cut freehand or freestyle into the flexible substrate and the protective material.

Referring back to FIG. 3, activity 212 can comprise activity 334 of cleaning the flexible substrate. In some examples, the second or non-planarized side of the flexible substrate (i.e., the side without the protective material) can be dry wiped to remove any oligomers, other chemicals, or particles. Afterwards, the planarized side of the flexible substrate having the protective material can be blown clean with a nitrogen gun. In other examples, both sides of the flexible substrate can be dry wiped and/or blown clean.

In some embodiments, activity 212 can comprise activity 335 of aligning the flexible substrate with a protective template. In some examples, the flexible substrate having the wafer shape with the tab can be aligned with the line trace of a carrier substrate drawn or made on the protective template in activity 331. The line trace of the carrier substrate can be slightly larger than the wafer shape of the flexible substrate.

In some embodiments, activity 212 can comprise activity 336 of coupling the flexible substrate to the protective template. In some embodiments, the flexible substrate can be attached to the protective template by attaching a portion of the tab of the flexible substrate to the protective template. For example, a piece of double-sided tape can couple the tab of the flexible substrate to the protective template. In some examples, a portion of the protective material can be peeled off of and removed from the tab, and the double-sided tape can be coupled to the exposed portion of the tab of the flexible substrate. In some examples, the portion of the protective material can be peeled using tweezers and can be cut from the protective template using a pair of ceramic scissors. In other examples, in activity 332, the protective material is not applied to the portion the tab to which the double-sided tape will be attached so peeling and removal of a portion of the protective material is not necessary.

Figure 5:
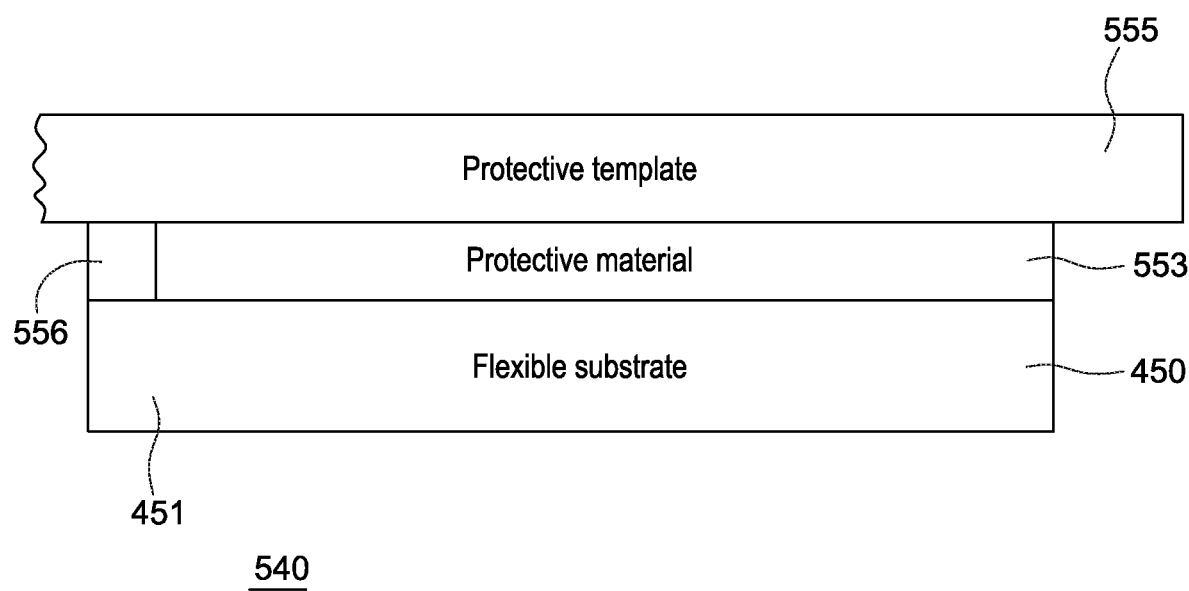
FIG. 5 illustrates a partial cross-sectional view of an example of the substrate assembly of FIG. 2 after attaching the flexible substrate of FIG. 3 to a protective template, according to the embodiment of FIG. 1.

After coupling the flexible substrate to the protective coating, the protective template is then folded over the flexible substrate. FIG. 5 illustrates a partial cross-sectional view of substrate assembly 540 after attaching flexible substrate 450 to protective template 555, according to the embodiment of FIG. 1. In this example, tape 556 can be coupled to flexible substrate 450 and protective template 555. Protective material 553 can be coupled to flexible substrate 450, as described previously.

In some examples, only one side of the flexible substrate is attached to the protective template. In other examples, both sides of the flexible substrate are attached to the protective template.

Turning back to FIG. 3, activity 212 can comprise activity 337 of laminating the flexible substrate, the protective material, and the protective template. The flexible substrate and the protective material can be located between the two folded halves of the protective template. The flexible substrate, the protective material, and the protective template can be laminated using a hot roll laminator to remove air bubbles between the protective material and the protective template and also between the protective material and the flexible substrate. In some examples, the flexible substrate and the protective template can be placed over a guide sheet (e.g., a Lexan® guide sheet) and fed into the hot roll laminator. As an example, the tab of the flexible substrate and the protective material can be fed first into the laminator. The flexible substrate and the protective template are laminated at a pressure of approximately 120 kPa (kilopascals) to approximately 160 kPa and at a temperature of approximately 90° C. to approximately 110° C. The lamination speed can be approximately one meter per minute to approximately two meters per minute.

In many embodiments, after laminating the flexible substrate and protective template, activity 212 can be complete. Referring back to FIG. 2, activity 110 can comprise activity 213 of providing a carrier substrate. In many embodiments, the carrier substrate can comprise a rigid substrate.

In some embodiments, the carrier substrate can be a 6, 8, 12, or 18 inch wafer or panel. However, when applicable, the carrier substrate can be any suitable size to accommodate a flexible substrate. In further embodiments, the carrier substrate can be a panel of approximately 300 mm by 350 mm, 300 mm by 400 mm, 320 mm by 400 mm, 365 mm by 460 mm, 370 mm by 400 mm, 370 mm by 470 mm, 400 mm by 500 mm, 550 mm by 650 mm, 680 mm by 880 mm, 730 mm by 920 mm, 1100 mm by 1250 mm, 1500 mm by 1800 mm, 1870 mm by 2200 mm, 2200 mm by 2500 mm, 2400 mm by 2800 mm, 2850 mm by 3050 mm, and 2880 mm by 3130 mm.

The carrier substrate can comprise a first surface and a second surface opposite the first surface. In some examples, at least one of the first surface and the second surface can be and/or has been polished. Polishing the surface that is not subsequently coupled to the flexible substrate can improve the ability of a vacuum or air chuck to handle the carrier substrate. Also, polishing the surface that is subsequently coupled to the flexible substrate can remove topological features of the surface of the carrier substrate that could cause roughness of the substrate assembly in the z-axis after the coupling with the flexible substrate.

In various embodiments, the carrier substrate can comprise at least one of the following: alumina ($Al_2O_3$), silicon, low CTE glass, steel, stainless steel, sapphire, barium borosilicate, soda lime silicate, an alkali silicate, or another material that is CTE matched to the flexible substrate. Where the substrate assembly comprises a flexible substrate, the CTE of the carrier substrate can be matched to the CTE of the flexible substrate. Non-matched CTEs can create stress between the carrier substrate and the flexible substrate.

For example, the carrier substrate could comprise sapphire with a thickness between approximately 0.7 mm and approximately 1.1 mm. The carrier substrate could also comprise 96% alumina with a thickness between approximately 0.7 mm and approximately 1.1 mm. In a different embodiment, the thickness of the 96% alumina is approximately 2.0 mm. In another example, the carrier substrate could be a single crystal silicon wafer with a thickness of at least approximately 0.65 mm. In still a further embodiment, the carrier substrate could comprise stainless steel with a thickness of at least approximately 0.5 mm. In some examples, the carrier substrate is slightly larger than the flexible substrate.

In some embodiments, activity 110 can comprise activity 214 of providing a cross-linking adhesive. In some examples, the cross-linking adhesive outgases at a rate of less than approximately 2×10-4 Torr-liters per second. In some examples, the cross-linking adhesive is thermally and/or UV (ultraviolet) light curable.

In various embodiments, the cross-linking adhesive can be a cross-linking acrylic adhesive. In the same or different embodiment, the cross-linking adhesive can be a cross-linking pressure sensitive acrylic adhesive or a cross-linking viscoelastic polymer. In some examples, the CTE of the adhesive can be very large compared to the CTE of the flexible substrate and the carrier substrate. However, the CTE of the adhesive may not be of concern because the adhesive may create marginal stress (i.e., viscoelasticity) between the flexible substrate and carrier substrate because the layer of adhesive is so thin compared to the thickness of the flexible substrate and carrier substrate.

In some embodiments, activity 110 can comprise activity 215 of depositing the cross-linking adhesive over a first surface of the carrier substrate. In many embodiments, depositing the cross-linking adhesive over a first surface of the carrier substrate can be performed using at least one of the following methods: spin-coating, spray-coating, extrusion coating, preform lamination, slot die coating, screen lamination, and screen printing.

For example, the carrier substrate can be coated with the cross-linking adhesive. The carrier substrate and the cross-linking adhesive can be spun to distribute the cross-linking adhesive over a first surface of the carrier substrate. In some embodiments, the cross-linking adhesive can be spin coated on the carrier substrate by spinning the carrier substrate with the cross-linking adhesive at approximately 900 rpm (revolutions per minute) to 1100 rpm for approximately 20 seconds to approximately 30 seconds and then spinning the carrier substrate with the cross-linking adhesive at approximately 3400 rpm to approximately 3600 rpm for approximately 10 seconds to 30 seconds. In a different embodiment, the carrier substrate with the cross-linking adhesive can be spun at approximately 600 rpm to approximately 700 rpm to coat the surface of the carrier substrate and then spun at approximately 3400 rpm to approximately 3600 rpm to control the thickness of the cross-linking adhesive.

Prior to spin coating, the cross-linking adhesive can be dispensed onto or over a geometric center of the carrier substrate. In a different embodiment, the cross-linking adhesive can be dispensed onto or over the carrier substrate while the carrier substrate is spinning.

The thickness of the cross-linking adhesive over the carrier substrate after the depositing activity can be between approximately three μm and approximately fifteen μm. In the same or different embodiment, the thickness of the cross-linking adhesive over the carrier substrate after the depositing activity can be between approximately ten μm and approximately twelve μm.

In some embodiments, activity 110 can comprise activity 216 of baking the cross-linking adhesive. In some embodiments, the cross-linking adhesive can be baked to remove solvents. For example, the cross-linking adhesive can be baked at 80° C. for thirty minutes and then baked for fifteen minutes at 130° C.

In other examples, the cross-linking adhesive is not baked. For example, if the cross-linking adhesive does not comprise any solvents, a bake is not necessary. Moreover, if the cross-linking adhesive is very viscous, solvents can even be added to the cross-linking adhesive to decrease the viscosity before the adhesive is deposited in activity 215.

Figure 6:
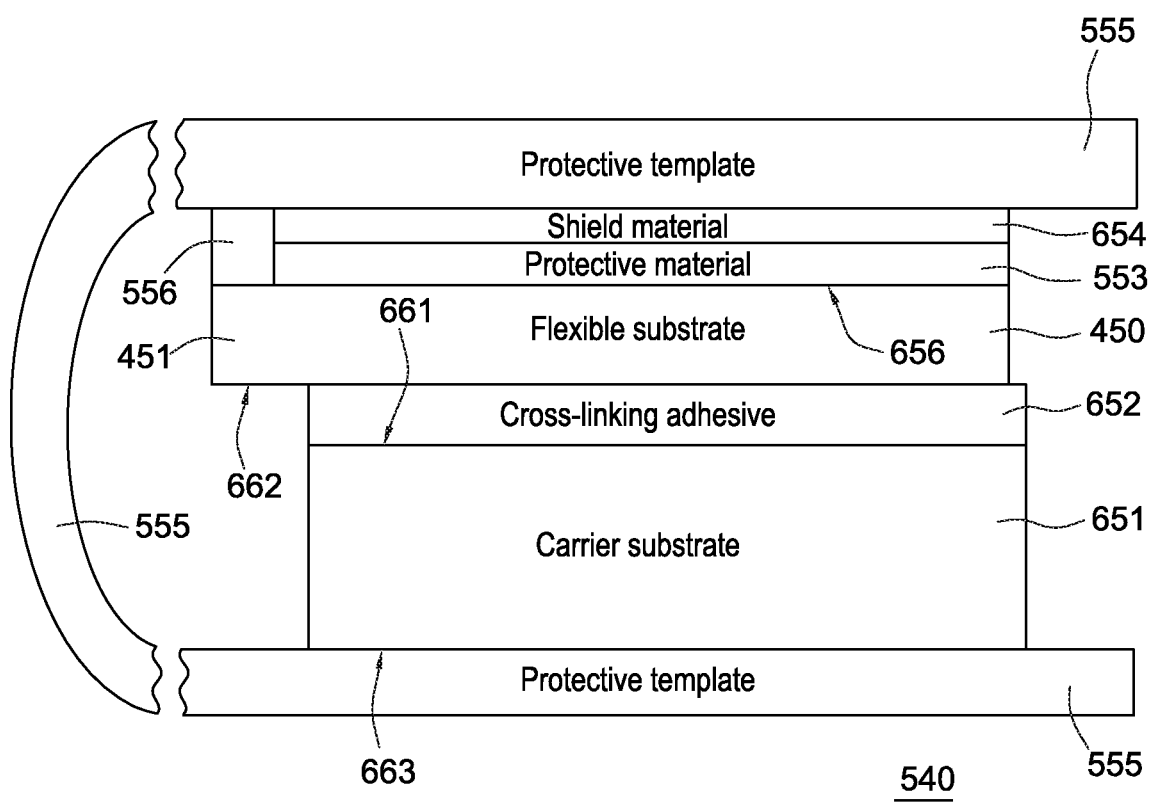
FIG. 6 illustrates a partial cross-sectional view of an example of the substrate assembly of FIG. 2 after coupling a carrier substrate to the flexible substrate, according to the embodiment of FIG. 1.

Afterwards, the carrier substrate can be placed on the protective template. The flexible substrate can be already coupled to one portion (or half) of the protective template as shown in FIG. 6, and the carrier substrate with cross-linking adhesive can be placed on another portion (or half) of the protective template. In some examples, the cross-linking adhesive can still be in liquid form at this point. Thus, the carrier substrate coated with the cross-linking adhesive can be stored horizontally for approximately eight to approximately twelve hours before being coupled with the flexible substrate.

In many embodiments, activity 110 can comprise activity 217 of coupling the carrier substrate to the flexible substrate (e.g., using the cross-linking adhesive while both substrates are located between the protective template halves). In some embodiments, the second surface of the flexible substrate can be placed over the first surface of the carrier substrate with the adhesive located between the second surface of the flexible substrate and the first surface of the carrier substrate. In other embodiments, one or more of activities 214-216 can be omitted.

In some examples, the carrier substrate can be coupled to the flexible substrate using the cross-linking adhesive by laminating the substrate assembly between the protective template halves to remove air bubbles between the carrier substrate and the flexible substrate. Laminating the flexible substrate involves first aligning the carrier substrate with the flexible substrate so that, when laminated, the carrier substrate and the flexible substrate are aligned. Then, the aligned structure can be fed through a hot roll laminator, which can be the same laminator of activity 337 of FIG. 3. The substrate assembly can be laminated at an approximate speed of 0.4 to 0.6 meters per minute.

Also, in various embodiments, the protective material may stick to the protective template when laminated. To avoid this problem, a shield material can be located between the protective template and the protective material before the lamination of activity 337 and/or activity 332. The shield material can be, for example, wax paper. In one embodiment, the shield material is originally coupled to the protective material when acquired from the manufacturer.

In the same or different embodiments, some of the cross-linking adhesive can be squeezed out from between the carrier and flexible substrates during lamination and adhere to the first side or the top of the flexible substrate, particularly because the carrier substrate and the overlying cross-linking adhesive layer is slightly larger than the flexible substrate. The presence of the protective material, however, prevents this problem from occurring. The cross-linking adhesive that squeezes out and adheres to the top of the protective material (instead of the flexible substrate) is inconsequential because the protective material is eventually removed and discarded.

FIG. 6 illustrates a partial cross-sectional view of substrate assembly 540 after coupling carrier substrate 651 to flexible substrate 450, according to the embodiment of FIG. 1. In this embodiment, cross-linking adhesive 652 can couple surface 661 of carrier substrate 651 to surface 662 of flexible substrate 450. Protective material 553 can be located over surface 656 of flexible substrate 450. Shield material 654 can be located between protective material 553 and protective template 555. Protective template 555 can be folded such that protective template 555 is also located under surface 663 of carrier substrate 651. Tape 556 can couple protective template 555 to tab 451 of flexible substrate 450. In some embodiments, such as where the substrate assembly of activity 110 comprises a rigid substrate but not a flexible substrate, substrate assembly 540 can comprise carrier substrate 651 without cross-linking adhesive 652 and flexible substrate 450.

Figure 7:
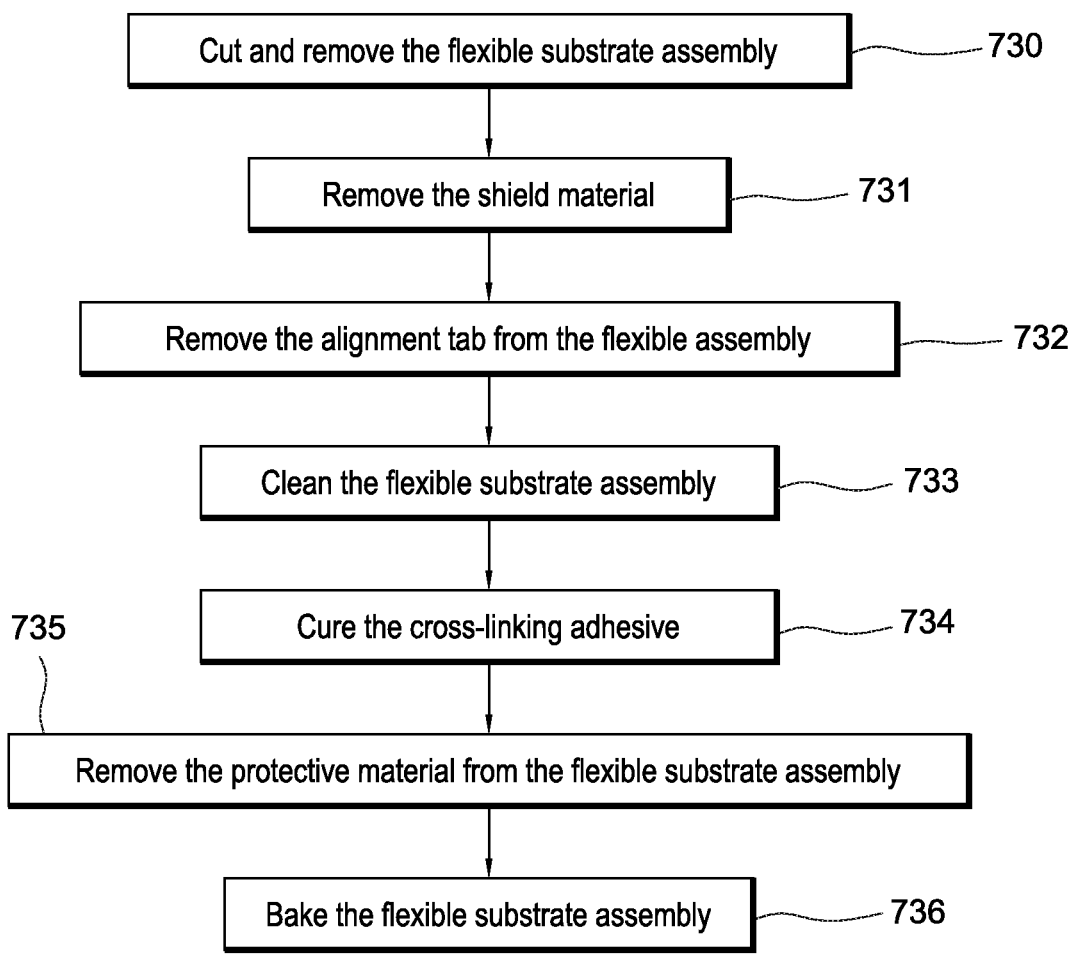
FIG. 7 illustrates an example of an activity of processing the substrate assembly of FIG. 2, according to the embodiment of FIG. 1.

Referring again back to FIG. 2, activity 110 can comprise activity 218 of processing the substrate assembly. FIG. 7 is a flow chart illustrating activity 218 of processing the substrate assembly, according to the embodiment of FIG. 1.

Figure 8:
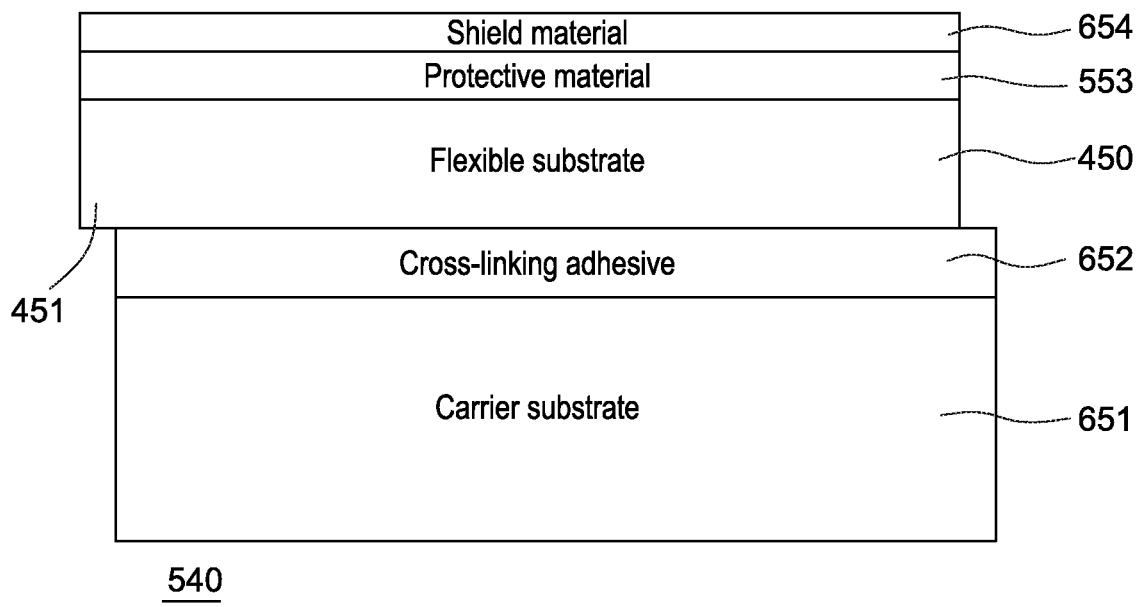
FIG. 8 illustrates a cross-sectional view of an example of the substrate assembly of FIG. 2 after cutting the substrate assembly and removing the protective template of FIG. 5, according to the embodiment of FIG. 1.

Activity 218 can comprise activity 730 of cutting the substrate assembly. In some examples, a pair of ceramic scissors can be used to cut the protective template and across the alignment tab of the flexible substrate located between the protective template, but the alignment tab is not removed entirely. After cutting the substrate assembly, the protective template can be peeled away from or otherwise removed from the shield material and the carrier substrate by hand. FIG. 8 illustrates a cross-sectional view of substrate assembly 540 after cutting the substrate assembly and removing the protective template, according to the embodiment of FIG. 1. More specifically, in FIG. 8, protective template 555 (FIGS. 5 & 6), and tape 556 (FIGS. 5 & 6) of flexible substrate 450 have been removed.

Referring again to FIG. 7, activity 218 can comprise activity 731 of removing the shield material by hand. In some examples, the substrate assembly can be placed at an edge of a table with the shield material facing the table. The substrate assembly can be slowly moved off the table while the shield layer is removed (e.g., peeled) from the substrate assembly. That is, the shield layer can be removed by pulling the shield material downward away from the edge of the table while the substrate assembly is moved horizontally off the table. In some examples, if the flexible substrate is not properly centered on or otherwise aligned with the carrier substrate after removing the shield layer, the flexible substrate can be slid into alignment with the carrier substrate.

Figure 9:
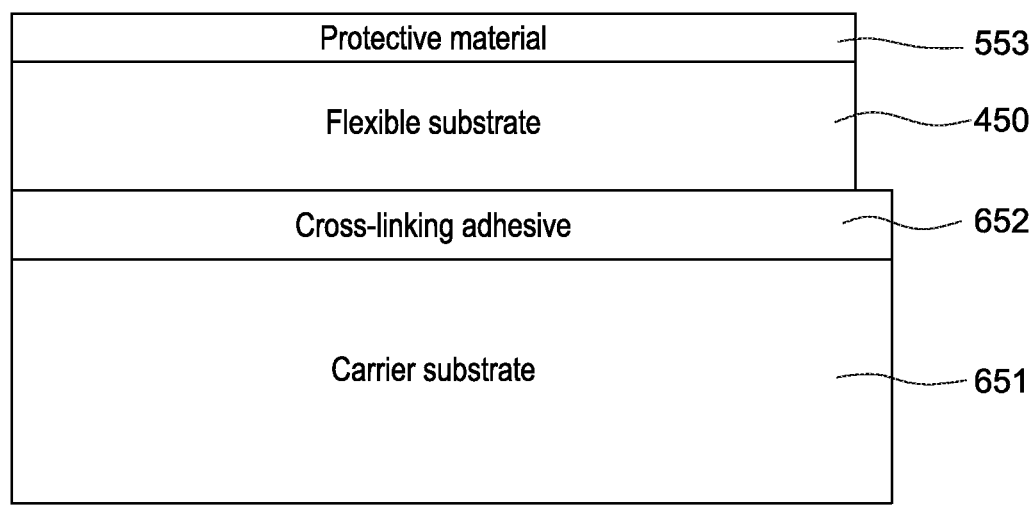
FIG. 9 illustrates a cross-sectional view of an example of the substrate assembly of FIG. 2 after removing an alignment tab, according to the embodiment of FIG. 1.

Further, activity 218 can comprise activity 732 of removing the alignment tab from the flexible assembly. In some examples, the alignment tab can be cut from the flexible substrate using ceramic scissors. The cut should be made slowly as any movement of the flexible substrate in the z-direction (relative to the carrier substrate) might cause de-lamination of the flexible substrate from the carrier substrate. If de-lamination occurs, the substrate assembly can be re-laminated. FIG. 9 illustrates a cross-sectional view of substrate assembly 540 after removing the alignment tab, according to the embodiment of FIG. 1.

Activity 218 can comprise activity 733 of cleaning the substrate assembly. In some examples, the substrate assembly can be cleaned with hexanes. The hexanes can be applied by spinning the substrate assembly and spraying the hexanes on the protective material. After the protective material is cleaned, the exposed surface and edge of the carrier substrate can be wiped clean with hexanes.

Activity 218 can comprise activity 734 of curing the cross-linking adhesive. In the same or different embodiment, the cross-linking adhesive can be UV cured. For example, the substrate assembly can be exposed to UV light for approximately 15 to 25 seconds and room temperature to cure the cross-linking adhesive. In some embodiments, the cross-linking adhesive can be cured with UV light in the UV light range of approximately 320 nm (nanometers) to approximately 390 nm and with an intensity of approximately 75 mW/cm$^2$ (milliWatts per square centimeter). A Dymax 2000-EC UV Curing Flood Lamp, manufactured by Dymax Corporation of Torrington, Conn., can be used to cure the cross-linking adhesive.

In various examples, the cross-linking adhesive can be thermally cured during the baking in activity 736. In some examples, the edges of the cross-linking adhesive can be UV cured, and the rest of the cross-linking adhesive can be thermally cured during the baking of activity 736.

Figure 10:
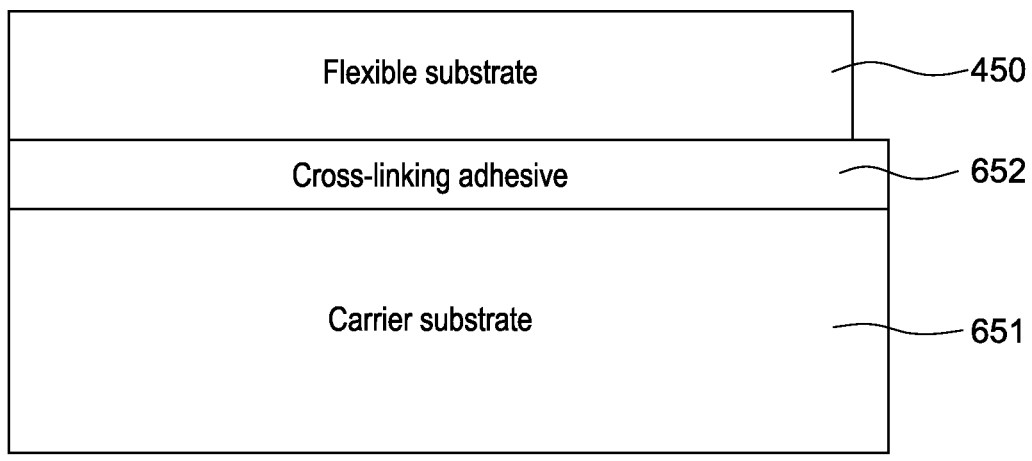
FIG. 10 illustrates a cross-sectional view of an example of the substrate assembly of FIG. 2 after removing a protective material from the substrate assembly, according to the embodiment of FIG. 1.

In many embodiments, activity 218 can comprise activity 735 of removing the protective material from the substrate assembly. In some examples, the protective material can be slowly removed using tweezers. During the removal activity, the protective material can be kept as flat as possible to avoid de-laminating the flexible substrate from the carrier substrate. In other examples, the protective material can be releasable by UV light. In these examples, the protective material would lose its tack during a UV light exposure. FIG. 10 illustrates a cross-sectional view of substrate assembly 540 after removing the protective material from the substrate assembly, according to the embodiment of FIG. 1.

In many embodiments, activity 218 can comprise activity 736 of baking the substrate assembly. Baking the substrate assembly can help decrease the distortion, bow, and warp in the flexible substrate. In some embodiments, baking can also cure the adhesive.

In some examples, the substrate assembly can be baked using a vacuum bake activity. For example, the temperature in an oven containing the substrate assembly can be ramped up over two to three hours to approximately 160° C. to approximately 190° C. The substrate assembly can be baked for approximately 50 minutes to 70 minutes at 180° C. and with a pressure of approximately 1 mTorr to approximately 10 mTorr. The temperature in the oven can then be lowered to between approximately 90° C. to 115° C., and the substrate assembly can be baked for approximately seven more hours to approximately nine more hours. Other baking activities also can be used. After the baking activity is complete, the flexible substrate assemblies are cleaned and placed in an oven at approximately 90° C. to 110° C. for a minimum of approximately two hours.

In many embodiments, after baking the substrate assembly, activity 218 can be complete, and therefore, activity 110 (FIG. 1) also can be complete.

Where the substrate assembly of activity 110 (FIG. 1) comprises a flexible substrate (e.g., flexible substrate 450 (FIG. 10)), activity 110 (FIG. 1) and/or activity 120 (FIG. 1), as described herein, and similar activities can allow fabrication of one or more electrical components on the flexible substrate with zero or at least minimal distortion (e.g. approximately the limits of the sensitivity of an Azores 5200, manufactured by Azores Corporation of Wilmington, Mass.). Prior art methods of fabricating electrical components on the flexible substrate suffer from significant distortion problems that can lead to handling errors, photolithographic alignment errors, and line/layer defects.

However, as indicated previously, it is also possible to perform activity 110 (FIG. 1) and/or activity 120 (FIG. 1), as described herein, and similar activities, where the substrate assembly of activity 110 comprises a rigid substrate (e.g., carrier substrate 651 (FIG. 10) but not a flexible substrate (e.g., flexible substrate 450 (FIG. 10)). Still, performing activity 110 (FIG. 1) such that the substrate assembly comprises the flexible substrate can provide various advantages, not the least of which can be the afore mentioned ability to fabricate one or more flexible electrical components.

U.S. Pat. No. 8,992,712, which issued Mar. 31, 2015, and U.S. Pat. No. 9,076,822, which issued Jul. 7, 2015, teach similar activities for providing a substrate assembly that can also be implemented in order to perform activity 110. Accordingly, U.S. Pat. Nos. 8,992,712 and 9,076,822 each are incorporated by reference herein in their entirety.

Figure 11:
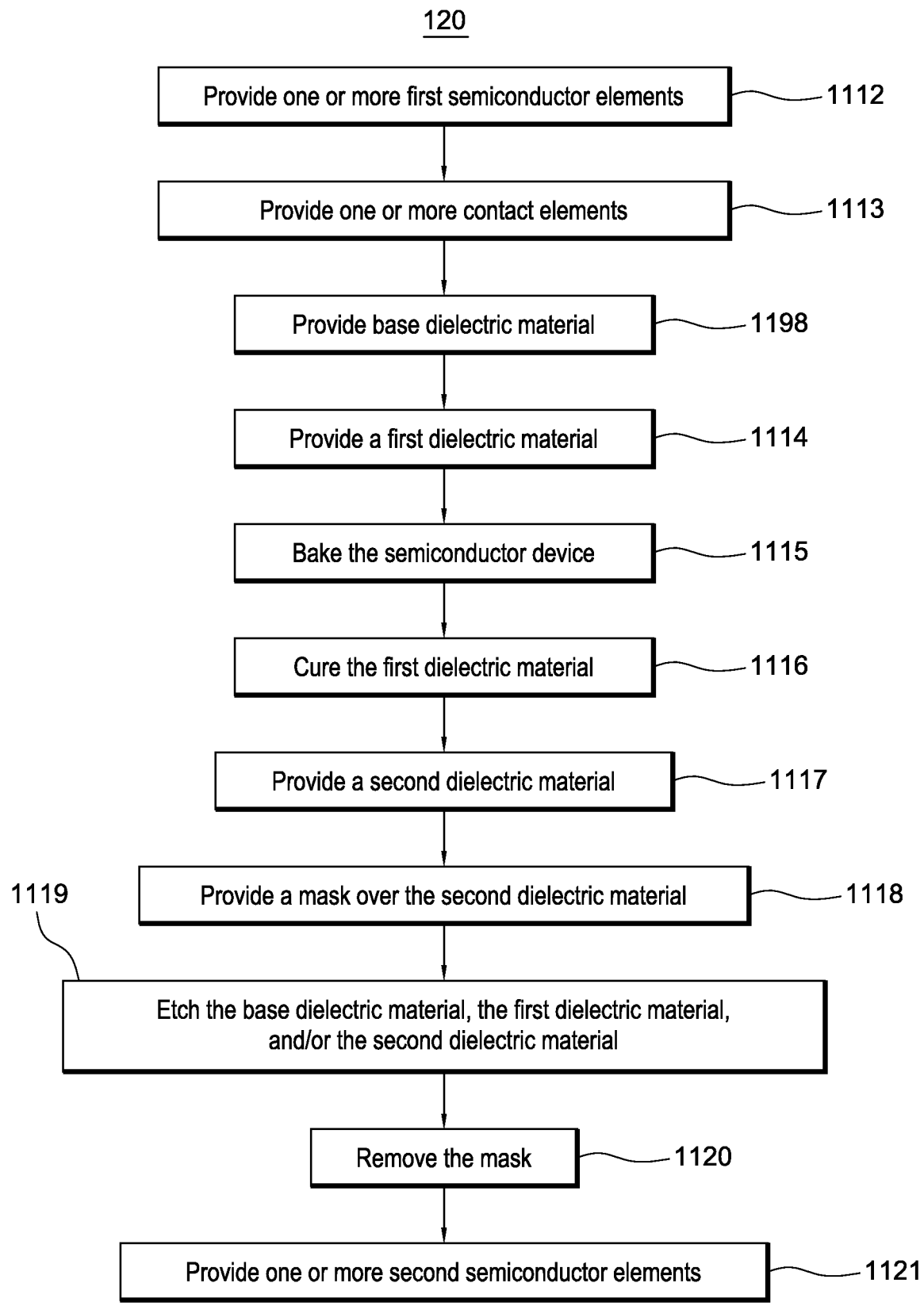
FIG. 11 illustrates an example of an activity of providing semiconductor elements, according to the embodiment of FIG. 1.

Referring back to FIG. 1, method 100 comprises activity 120 of providing semiconductor elements. FIG. 11 is a flow chart illustrating activity 120 of providing semiconductor elements, according to the embodiment of FIG. 1.

Figure 12:
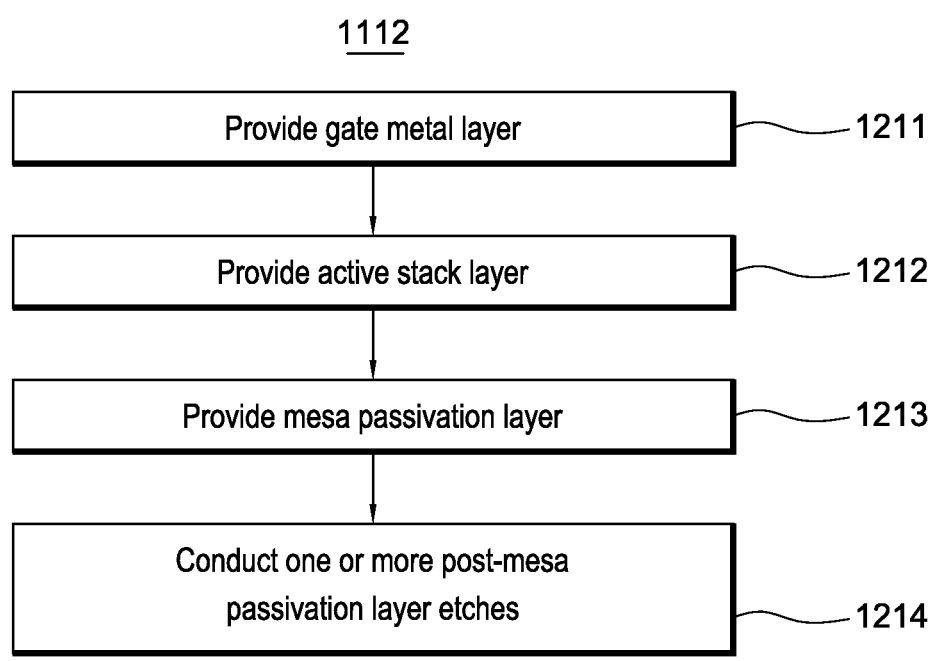
FIG. 12 illustrates an example of an activity of providing one or more first semiconductor elements, according to the embodiment of FIG. 1.

In many embodiments, activity 120 can comprise activity 1112 of providing one or more first semiconductor elements. FIG. 12 is a flow chart illustrating activity 1112 of providing one or more first semiconductor elements, according to the embodiment of FIG. 1.

Figure 13:
FIG. 13 illustrates a cross-sectional view of an example of a device build area of an example of a semiconductor device after providing a gate metal layer, according to the embodiment of FIG. 1.
Figure 14:
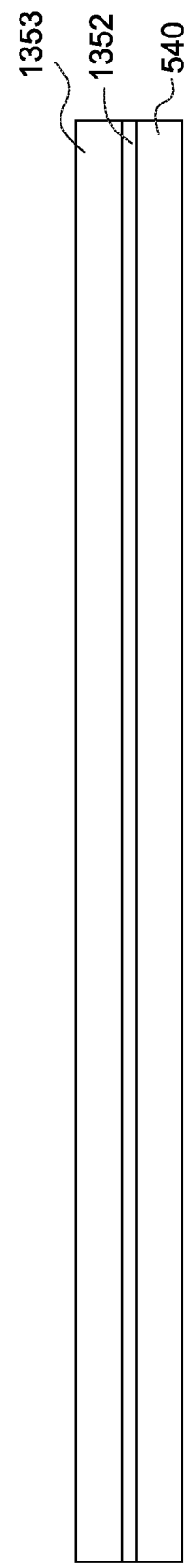
FIG. 14 illustrates a cross-sectional view of an example of a gate contact build area of an example of the semiconductor device of FIG. 13 after providing the gate metal layer, according to the embodiment of FIG. 1.
Figure 29:
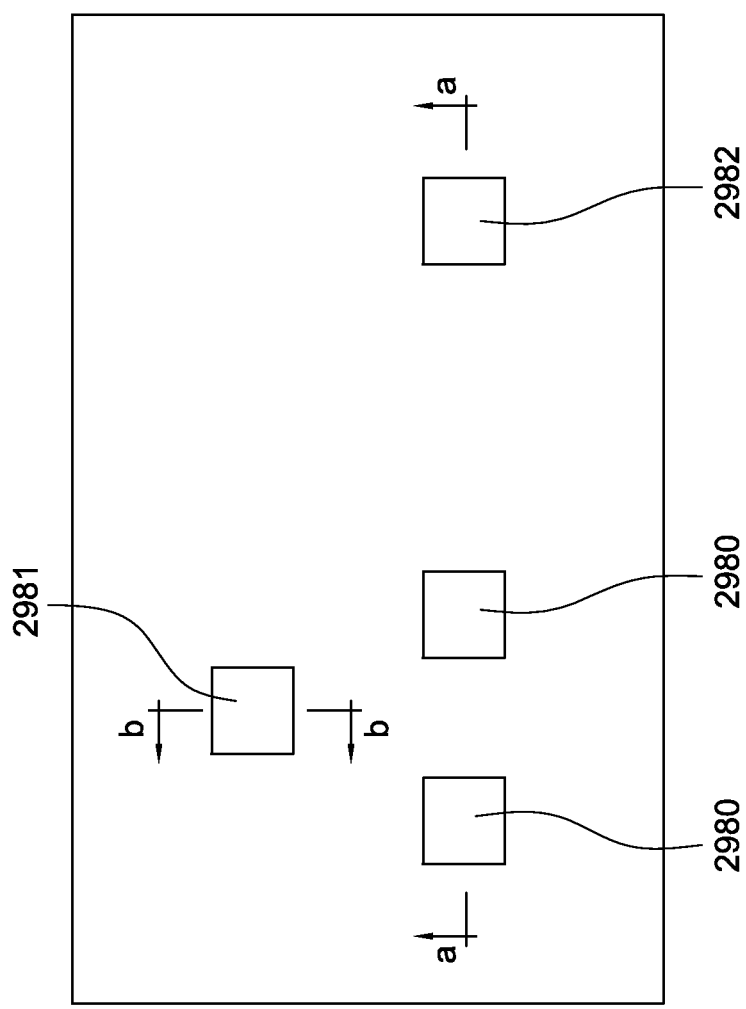
FIG. 29 illustrates a top view of portions of the semiconductor device represented in FIGS. 13 and 14, according to the embodiment of FIG. 1.

In some embodiments, activity 1112 can comprise activity 1211 of providing a gate metal layer. In some embodiments, the substrate assembly of activity 110 (FIG. 1) can be cleaned by a quick-dump-rinse (QDR) activity with a suitable detergent followed by a spin-rinse-dry (SRD) activity prior to performing activity 1211. An exemplary detergent can comprise Alconox Detergent 8, manufactured by Alconox, Inc. of White Plains, N.Y., (e.g., 40 mL) mixed with one liter of water. The cleaning can be performed in a megasonic cleaning tank. FIG. 13 illustrates a cross-sectional view of a device build area of an example of semiconductor device 1350 after providing a gate metal layer, according to the embodiment of FIG. 1. As can be seen in FIG. 29, the cross-sectional view of the device build area is the cross-sectional view of a portion of semiconductor device 1350 taken at the "a" lines. The device build cross sectional view comprises a cross-sectional view of contact areas 2980 and via area 2982. In addition, FIG. 14 illustrates a cross-sectional view of a gate contact build area of an example of semiconductor device 1350 after providing a gate metal layer, according to the embodiment of FIG. 1. As can be seen in FIG. 29, the cross-sectional view of the gate contact build area is the cross-sectional view of a portion of semiconductor device 1350 taken at the "b" lines. The gate contact build cross sectional view comprises a cross-sectional view of gate contact area 2981. FIG. 29 is merely exemplary and is not limited to the embodiments presented herein.

Referring to FIGS. 13 and 14, for example, passivation layer 1352 can be provided over substrate assembly 540. In many examples, passivation layer 1352 can be deposited onto semiconductor device 1350 over substrate assembly 540 by way of plasma-enhanced chemical vapor deposition (PECVD). In these or other examples, passivation layer 1352 can be deposited at a temperature less than or equal to approximately 200° C. When substrate assembly 540 comprises a flexible substrate (e.g., flexible substrate 450 (FIG. 10)), passivation layer 1352 can be provided over flexible substrate 450 (FIG. 10) of substrate assembly 540. In some embodiments, flexible substrate 450 can be baked prior to the deposition of passivation layer 1352.

Passivation layer 1352 can comprise a dielectric material. The dielectric material can comprise silicon dioxide and/or silicon nitride. Further, passivation layer 1352 can be greater than or equal to approximately 200 nanometers thick and less than or equal to approximately 400 nanometers thick. For example, passivation layer 1352 can be approximately 300 nanometers thick. In some embodiments, passivation layer 1352 can protect one or more other layers of semiconductor device 1350 (e.g., patterned active layer 1555 (FIGS. 15, 17, 19, 21, 24-26, & 32) from atmospheric contamination.

In addition, patterned metal gate 1353 can be provided over passivation layer 1352. Patterned metal gate 1353 can comprise molybdenum, tantalum, aluminum, neodymium, chromium, niobium, titanium, silicon, and/or tungsten. Further, patterned metal gate 1353 can be greater than or equal to approximately 100 nanometers thick and less than or equal to approximately 200 nanometers thick. In specific examples, an approximately 150 nanometer layer of molybdenum can be deposited over passivation layer 1352 and then pattern etched to form patterned metal gate 1353. In these or other examples, patterned metal gate 1353 can be deposited over passivation layer 1352 by sputtering.

In some examples, patterned metal gate 1353 can be deposited using a KDF 744, manufactured by KDF Electronic, Inc., of Rockleigh, N.J. Patterned metal gate 1353 can be deposited such that the sidewalls of patterned metal gate 1353 slope downwardly and/or outwardly toward passivation layer 1353 at an angle of less than or equal to approximately 45 degrees with respect to the horizontal. In the same or different examples, patterned metal gate 1353 can be etched using a reactive ion etcher, such as, for example, an AMAT 8330, manufactured by Applied Material, Inc. of Santa Clara, Calif. Passivation layer 1352 can act as a moisture barrier and an etch stop for patterned metal gate 1353. The etchant can comprise any suitable dry etchant (e.g., a chlorine and oxygen dry etchant) or any suitable wet etchant, such as, for example, a mixture of phosphoric acid, acetic acid, and/or water.

Figure 15:
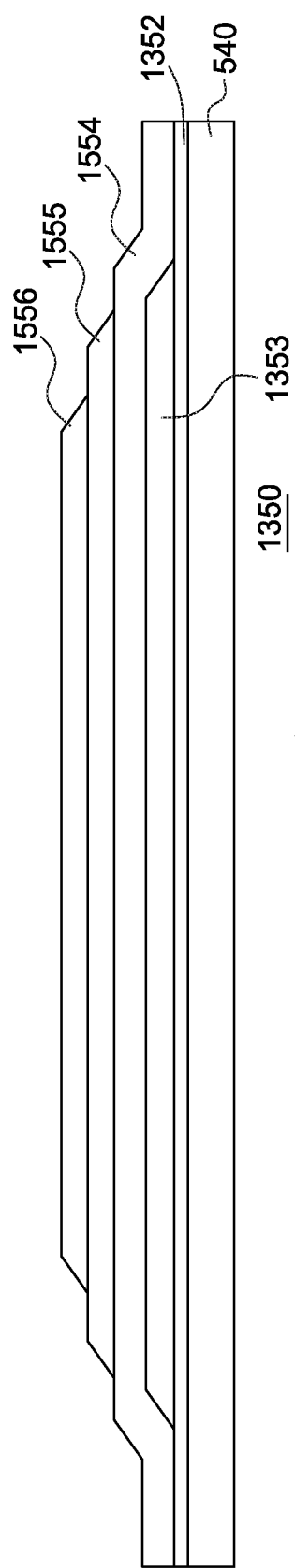
FIG. 15 illustrates a cross-sectional view of an example of the device build area of the semiconductor device of FIG. 13 after providing an active stack layer, according to the embodiment of FIG. 1.
Figure 16:
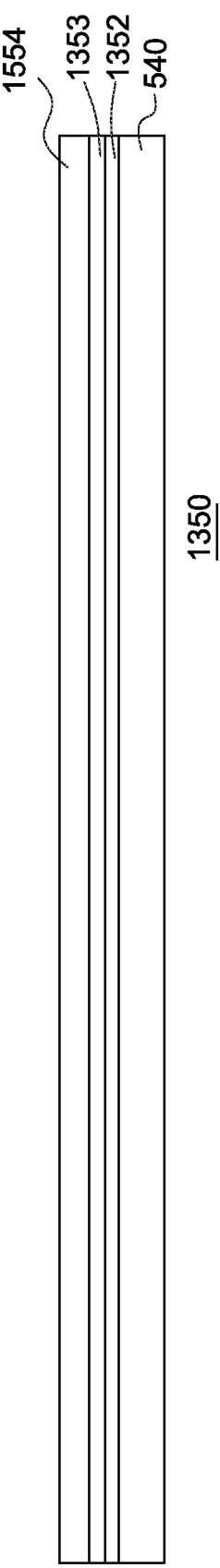
FIG. 16 illustrates a cross-sectional view of an example of the gate contact build area of the semiconductor device of FIG. 14 after providing the active stack layer, according to the embodiment of FIG. 1.

Referring again to FIG. 12, activity 1112 can comprise activity 1212 of providing an active stack. In some embodiments, the substrate assembly of activity 110 (FIG. 1) and the gate metal layer of activity 1211 can be cleaned by a QDR activity with a suitable detergent followed by a SRD activity prior to performing activity 1212. An exemplary detergent can comprise Alconox Detergent 8, manufactured by Alconox, Inc. of White Plains, N.Y., (e.g., 40 mL) mixed with one liter of water. The cleaning can be performed in a megasonic cleaning tank. FIGS. 15 and 16 illustrate an example of semiconductor device 1350 after providing an active stack, according to the embodiment of FIG. 1.

Referring to FIGS. 15 and 16, for example, gate dielectric 1554 can be formed over patterned metal gate layer 1353 and passivation layer 1352. Referring to FIG. 15, for example, in the device build area of semiconductor device 1350, patterned active layer 1555 can be provided over gate dielectric 1554, and patterned intermetal dielectric (IMD) layer 1556 can be provided over patterned active layer 1555. In some embodiments, the substrate assembly of activity 110 (FIG. 1) and the gate metal layer of activity 1211 can be cleaned with a solution of ammonium hydroxide and water in ratio of one part to ten parts, respectively. In some examples, patterned active layer 1555 can be referred to as a transistor active layer.

In some examples, as shown in FIGS. 15 and 16, gate dielectric 1554 can be deposited onto semiconductor device 1350 over metal gate layer 1353 and/or passivation layer 1352 by way of PECVD. Gate dielectric 1554 can comprise one or more gate dielectric materials. Exemplary gate dielectric material(s) can comprise one or more oxides (e.g., silicon dioxide), one or more nitrides (e.g., silicon nitride), one or more silicon oxynitrides, one or more hafnium oxynitrides, one or more aluminum oxynitrides, one or more barium oxynitrides, and/or one or more strontium oxynitrides. Further exemplary gate dielectric material(s) can comprise one or more organic polymer materials. In some embodiments, gate dielectric 1154 can be buffered with silicon nitride and/or one or more other dielectric materials on the side of gate dielectric 1154 closest to patterned metal gate 1353. Accordingly, in certain examples, gate dielectric 1554 can be deposited onto semiconductor device 1350 by way of PECVD using silane ($SiH_4$) and nitrous oxide ($N_2O$) precursor gases. The ratio of silane to nitrous oxide can be 100 to 1 parts by volume to minimize the hydrogen content in gate dielectric 1554. When gate dielectric 1554 comprises silicon nitride, the silicon nitride can be hydrogenated. The index of refraction of gate dielectric 1554 can be tuned to greater than or equal to 1.8 and less than or equal to 1.85 (e.g., at 633 nanometers). Gate dielectric 1554 can be greater than or equal to approximately 100 nanometers thick and less than or equal to approximately 300 nanometers thick, such as, for example, approximately 200 nanometers thick.

With reference to FIG. 15, as an example, patterned active layer 1555 can be deposited over gate dielectric 1554 by way of PECVD and/or by way of sputtering. In some embodiments, patterned active layer 1555 can comprise amorphous silicon (a-Si) and/or hydrogenated amorphous silicon (a-Si:

H). In these examples, in certain examples, patterned active layer 1555 can be deposited onto semiconductor device 1350 by way of PECVD using silane ($SiH_4$) and hydrogen ($H_2$) precursor gases. The index of refraction of patterned active layer 1555 can be tuned to greater than or equal to 3.65 and less than or equal to 3.75 (e.g., at 633 nanometers), such as, for example, to provide a particular silicon and hydrogen composition. In other embodiments, patterned active layer 1555 can comprise one or more metal oxides. For example, patterned active layer 1555 can comprise indium, indium oxide, zinc, zinc oxide, gallium, gallium oxide, tin, tin oxide, hafnium, hafnium oxide, zirconium, zirconium oxide, aluminum, aluminum oxide, silicon, silicon oxide, copper, copper oxide, cobalt, and/or cobalt oxide, in equal or unequal proportions to one another. Further, patterned active layer 1555 can comprise one or more organic polymer materials. In the same or different examples, patterned active layer 1555 can be greater than or equal to approximately 50 nanometers thick and less than or equal to approximately 80 nanometers thick. In some embodiments, patterned active layer 1555 can comprise a single active layer or multiple constituent active layers.

Figure 31:
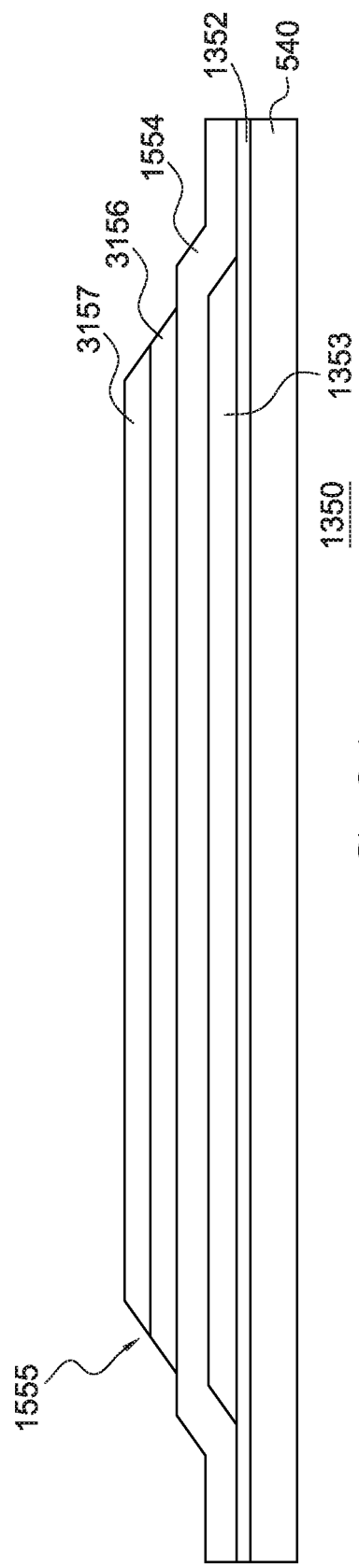
FIG. 31 illustrates a patterned active layer when the patterned active layer comprises multiple constituent active layers, according the embodiment of FIG. 1.

Turning ahead in the drawings, FIG. 31 illustrates patterned active layer 1555 when patterned active layer 1555 comprises multiple constituent active layers, such as, for example, first constituent active layer 3156 and second constituent active layer 3157, according the embodiment of FIG. 1. First constituent active layer 3156 and/or second constituent active layer 3157 can be patterned. Patterned active layer 1555 is shown after patterned active layer 1555 is deposited over gate dielectric 1554 but prior to deposition of patterned IMD layer 1556. Accordingly, first constituent active layer 3156 can be over gate dielectric 1554, and/or second constituent active layer 3157 can be over first constituent active layer 3156. Further, although not shown at FIG. 31, in some embodiments, patterned IMD layer 1556 (FIG. 15) can be over and/or on second constituent active layer 3157.

With respect to composition, first constituent active layer 3156 can comprise one or more first metal oxides and a first conductivity and/or resistivity. Further, second constituent active layer 3157 can comprise one or more second metal oxides and a second conductivity and/or resistivity. Implementing patterned active layer 1555 to comprise both first constituent active layer 3156 and second constituent active layer 3157 can help to ensure that semiconductor device 1350 can be turned off, which may not happen if patterned active layer 1555 comprises first constituent active layer 3156 only.

For example, the first metal oxide(s) can comprise one or more of indium, indium oxide, zinc, zinc oxide, gallium, gallium oxide, tin, tin oxide, hafnium, hafnium oxide, zirconium, zirconium oxide, aluminum, aluminum oxide, silicon, silicon oxide, copper, copper oxide, cobalt, and/or cobalt oxide, in equal or unequal proportions to one another. More specifically, the first metal oxide(s) can comprise approximately sixty percent zinc oxide and approximately forty percent indium oxide. In other examples, the first metal oxide(s) can comprise indium oxide, gallium oxide, and zinc oxide in equal proportions to each other. Meanwhile, the second metal oxide(s) can be similar to, identical to, or different from the first metal oxide(s). For example, where the second metal oxide(s) comprise the first metal oxide(s), the second metal oxide(s) can comprise (i) the same or different constituent compounds/elements of the first metal oxide(s) and/or (ii) the same or different relative proportions of the constituent compounds/elements of the first metal oxide(s). In some examples, the first metal oxide(s) can comprise approximately sixty percent zinc oxide and approximately forty percent indium oxide; meanwhile, the second metal oxide(s) can comprise indium oxide, gallium oxide, and zinc oxide in equal proportions to each other; or vice versa. In other examples, both the first and second metal oxide(s) can comprise zinc oxide and indium oxide with the second metal oxide having an approximately 60:40 ratio of zinc oxide to indium oxide and with the first metal oxide having an approximately 59:41 ratio of zinc oxide to indium oxide.

With respect to thickness, first constituent active layer 3156 can be greater than or equal to approximately 5 nanometers thick and less than or equal to approximately 40 nanometers thick. In further embodiments, first constituent active layer 3156 can be greater than or equal to approximately 5 nanometers thick and less than or equal to approximately 20 nanometers thick, such as, for example, approximately 20 nanometers thick. Meanwhile, second active layer 3157 can be greater than or equal to approximately 10 nanometers thick and less than or equal to approximately 45 nanometers thick, such as, for example, approximately 30 nanometers thick. In some embodiments, a combined thickness of first constituent active layer 3156 and second constituent active layer 3157 does not exceed approximately 50 nanometers.

The first conductivity/resistivity can be greater than the second conductivity/resistivity, or vice versa. For example, the first resistivity of first constituent active layer 3156 can comprise approximately 0.002 Ohm-centimeters. Further, the second conductivity/resistivity of second constituent active layer 3157 can comprise greater than or equal to approximately 10 Ohm-centimeters and less than or equal to approximately 200 Ohm-centimeters. Accordingly, in many examples, the second resistivity greatly exceeds the first resistivity. Correspondingly, the second conductivity can be less than the first conductivity. The greater conductivity of first constituent active layer 3156 versus second constituent active layer 3157 can result from second constituent active layer 3157 comprising a higher oxygen content than first constituent active layer 3156. As the oxygen content of second constituent active layer 3157 increases, so too can the resistivity of second constituent active layer 3157. The differential in the conductivities between first constituent active layer 3156 and second constituent active layer 3157 can greatly affect (e.g., reduce) the rate of change or shift in the threshold voltage of semiconductor device 1350 due to an applied gate voltage when compared to a similar semiconductor device that has a single active layer. A stable threshold voltage can permit semiconductor device 1350 to provide a repeatable signal. The manner of implementing second constituent active layer 3157 to comprise greater oxygen content than first constituent active layer 3156 is described in further detail below.

In many examples, implementing patterned active layer 1555 as multiple constituent active layers (e.g., first constituent active layer 3156 and/or second constituent active layer 3157) comprising metal oxides and/or different conductivities can provide improved mobility, on/off current ratio, and threshold voltage stability over implementing patterned active layer 1555 as (i) a single active layer, whether or not comprising amorphous silicon, and/or (ii) multiple constituent active layers comprising amorphous silicon and/or similar or identical conductivities. As a result, one or more electronic devices of semiconductor device 1350 can be fabricated smaller and/or with higher device resolution.

Referring now back to FIG. 15, as an example, patterned IMD layer 1556 can be deposited over patterned active layer 1555 by way of PECVD. Patterned IMD layer 1556 can comprise silicon nitride and/or silicon dioxide. In some examples, patterned IMD layer 1556 can be buffered with silicon nitride or other dielectrics on the side farthest from patterned active layer 1555. In other examples, when patterned active layer 1555 comprises a-Si and/or a-Si:H, patterned IMD layer 1556 can comprise hydrogenated silicon nitride. Further, patterned IMD layer 1556 can be greater than or equal to approximately 50 nanometers thick and less than or equal to approximately 200 nanometers thick. For example, patterned IMD layer 1556 can be approximately 100 nanometers thick.

In some examples, gate dielectric 1554, patterned active layer 1555, and/or patterned IMD layer 1556 can all be deposited via PECVD using an AMAT P5000, manufactured by Applied Materials, Inc. of Santa Clara, Calif. In the same or different examples, the temperature at which gate dielectric 1554, patterned active layer 1555, and/or patterned IMD layer 1556 are deposited onto semiconductor device 1350 can be greater than approximately 180° C. For example, the temperature at which gate dielectric 1554, patterned active layer 1555, and/or patterned IMD layer 1556 are deposited onto semiconductor device 1350 can be greater than or equal to approximately 180° C. and less than or equal to approximately 250° C. As an example, the temperature at which gate dielectric 1554, patterned active layer 1555, and patterned IMD layer 1556 are deposited onto semiconductor device 1350 can be from approximately 188° C. to approximately 193° C. Furthermore, the deposition of gate dielectric 1554, patterned active layer 1555, and patterned IMD layer 1556 onto semiconductor device 1350 can be done at approximately vacuum.

In other examples, such as, for example, when patterned active layer 1555 comprises multiple constituent active layers (e.g., first constituent active layer 3156 (FIG. 31) and/or second constituent active layer 3157 (FIG. 31)), the multiple constituent active layers can be deposited via sputtering (as opposed to PECVD). In these examples, sputtering the first constituent active layer 3156 (FIG. 31) can comprise sputtering the first metal oxide(s) of first constituent active layer 3156 with a first feed gas comprising (i) argon and/or nitrogen and (ii) being approximately devoid of oxygen. Further, sputtering the second constituent active layer 3157 (FIG. 31) (e.g., over and/or on first constituent active layer 3156 (FIG. 31) can comprise sputtering the second metal oxide(s) of second constituent active layer 3157 with a second feed gas comprising (i) argon and/or nitrogen and (ii) oxygen. For example, the second feed gas can be greater than or equal to approximately 2 percent oxygen by volume and less than or equal to approximately 10 percent oxygen by volume. The threshold voltage shift of the semiconductor device(s) comprising patterned active layer 1555 can be reduced as a function of increasing the oxygen content of the second feed gas toward 10 percent oxygen by volume. In many examples, this improved voltage shift can be achieved with little or no measurable effect on other electrical properties (e.g., mobility, on/off current ratio, etc.) of the semiconductor device(s). Accordingly, the threshold voltage shift of the semiconductor device(s) comprising patterned active layer 1555 can be greater than or equal to −1 Volt and less than or equal to 1 Volt for a ±20 Volt direct current bias stress applied for 10,000 seconds.

In some examples, the second feed gas can comprise the first feed gas, such as, for example, when oxygen is combined with the first feed gas to form the second feed gas. Accordingly, in these or other examples, second constituent active layer 3157 can be deposited directly after first constituent active layer 3156 is deposited, such as, for example, where depositing first constituent active layer 3156 transitions directly into depositing second constituent active layer 3157 by selectively adding oxygen to the first feed gas when desirable. In this example, the chamber in which first and second constituent active layers 3156 and 3157 are deposited does not need to break vacuum between layers, and a single etch mask can be used to pattern both layers.

In many examples, the temperature at which first constituent active layer 3156 (FIG. 31) and/or second constituent active layer 3157 (FIG. 31) are deposited onto semiconductor device 1350 can be greater than or equal to approximately 25° C. and less than or equal to approximately 39° C. Further, the deposition of first constituent active layer 3156 (FIG. 31) and/or second constituent active layer 3157 (FIG. 31) onto semiconductor device 1350 can be done at a pressure of greater than or equal to approximately 10 milliTorr and less than or equal to approximately 20 milliTorr, such as, for example, at a pressure of approximately 16 milliTorr.

After gate dielectric 1554, patterned active layer 1555, and patterned IMD layer 1556 are deposited onto semiconductor device 1350, the resulting layers can be pattern etched. Prior to etching gate dielectric 1554, patterned active layer 1555, and patterned IMD layer 1556, the substrate assembly of activity 110 (FIG. 1), the gate metal layer of activity 1211, and the active stack of activity 1212 can be cleaned by a QDR activity with a suitable detergent followed by a SRD activity prior to performing activity 1212. An exemplary detergent can comprise Alconox Detergent 8, manufactured by Alconox, Inc. of White Plains, N.Y., (e.g., 40 mL) mixed with one liter of water. The cleaning can be performed in a megasonic cleaning tank. In many examples, gate dielectric 1554 can provide an etch stop for the patterned etches of patterned active layer 1555 and/or patterned IMD layer 1556.

In some examples, patterned IMD layer 1556 can be etched using a 10:1 buffered oxide etch (BOE), such as, for example, when patterned IMD layer 1556 comprises silicon nitride. In other examples, patterned IMD layer 1556 can be etched using a dry etchant, such as, for example, when patterned IMD layer 1556 comprises silicon dioxide. For example, the dry etchant can comprise oxygen, hydrogen chloride, and methane. Further, the oxygen, hydrogen chloride, and methane can comprise ten, one hundred, and twenty parts per volume, respectively. Meanwhile, gate dielectric 1554 and patterned active layer 1555 can be etched in similar or identical manner to and/or as part of the etching of ITO layer 2667 (FIG. 26), as described below. For example, gate dielectric 1554 and patterned active layer 1555 can be etched using a reactive ion etcher, such as, for example, an AMAT 8330. In some examples, patterned IMD layer 1556 and patterned active layer 1555 can be etched so that patterned active layer 1555 is exposed, i.e., patterned active layer 1555 is not completely covered by patterned IMD layer 1556. Where patterned active layer 1555 comprises multiple constituent active layers (e.g., first constituent active layer 3156 (FIG. 31) and second constituent active layer 3157 (FIG. 31)), each of the multiple constituent active layers can be etched (i) immediately sequentially and/or (ii) separately, such as, for example, (a) the etch can be performed after each layer of the multiple constituent active layers is deposited and before the next constituent active layer is deposited or (b) the etch can be performed for each layer of the multiple constituent active layers after all of the multiple constituent active layers are deposited so that they are etched in the reverse order of deposition.

In many examples, the active stack of activity 1212 can comprise a layer-to-layer registration error of less than or equal to approximately 1 pixel per million. Further, the active stack of activity 1212 can comprise a change in wafer bow of between approximately ±5 microns.

Figure 17:
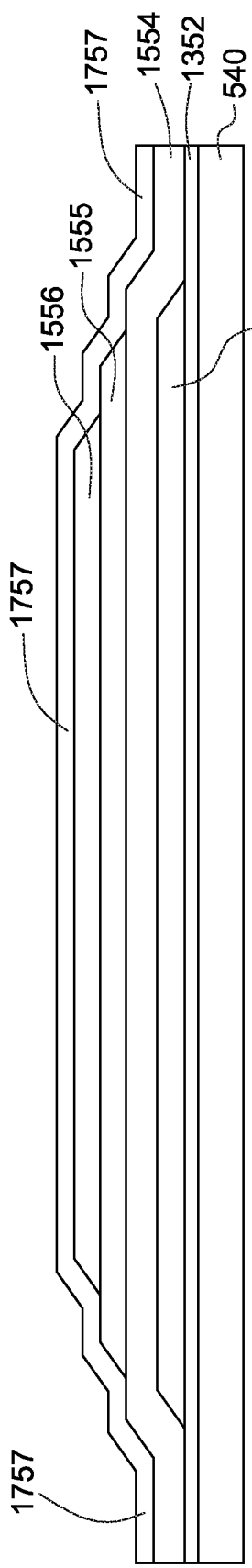
FIG. 17 illustrates a cross-sectional view of an example of the device build area of the semiconductor device of FIG. 13 after providing a mesa passivation layer, according to the embodiment of FIG. 1.
Figure 18:
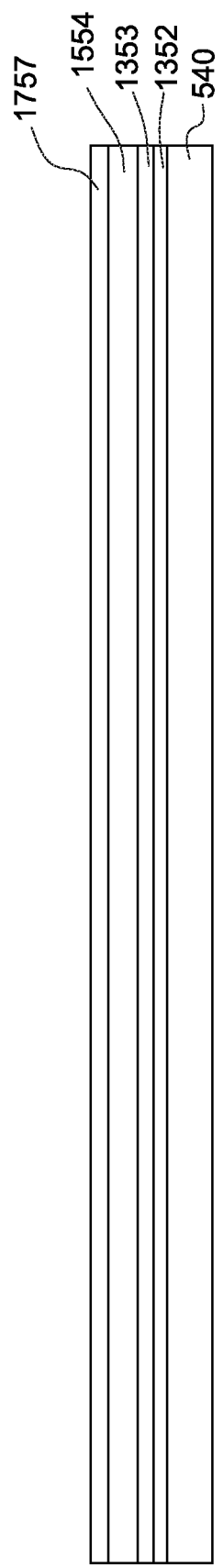
FIG. 18 illustrates a cross-sectional view of an example of the gate contact build area of the semiconductor device of FIG. 14 after providing the mesa passivation layer, according to the embodiment of FIG. 1.

Referring again to FIG. 12, activity 1112 can comprise activity 1213 of providing a mesa passivation layer. Prior to performing activity 1213, the substrate assembly of activity 110 (FIG. 1), the gate metal layer of activity 1211, and the active stack of activity 1212 can be cleaned by a QDR activity with a suitable detergent followed by a SRD activity. An exemplary detergent can comprise Alconox Detergent 8, manufactured by Alconox, Inc. of White Plains, N.Y., (e.g., 40 mL) mixed with one liter of water. The cleaning can be performed in a megasonic cleaning tank. Additionally or alternatively, the substrate assembly of activity 110 (FIG. 1), the gate metal layer of activity 1211, and the active stack of activity 1212 can be cleaned with a solution of ammonium hydroxide and water in ratio of one part to ten parts, respectively. FIGS. 17 and 18 illustrate an example of semiconductor device 1350 after providing a mesa passivation layer, according to the embodiment of FIG. 1.

With reference to FIG. 17, as an example, in the device build area of semiconductor device 1350, mesa passivation layer 1757 is deposited onto semiconductor device 1350 over gate dielectric 1554, patterned active layer 1555, and patterned IMD layer 1556. Mesa passivation layer 1757 can comprise silicon nitride and/or silicon dioxide. In many embodiments, mesa passivation layer 1757 can be similar or identical to patterned IMD layer 1556. Further, mesa passivation layer 1757 can be greater than or equal to approximately 50 nanometers thick and less than or equal to approximately 300 nanometers thick, such as, for example, approximately 100 nanometers thick. Mesa passivation layer 1757 can be deposited over patterned active layer 1555 to passivate and/or encapsulate the surface of patterned active layer 1555, thereby preventing contamination of the surface of patterned active layer 1555 and lowering leakage currents along the surface of patterned active layer 1555. Mesa passivation layer 1757 can also protect the sidewalls of patterned active layer 1555 during subsequent etches. With reference to FIG. 18, as an example, in the gate contact build area of semiconductor device 1350, mesa passivation layer 1757 can be deposited over gate dielectric 1554.

Mesa passivation layer 1757 can be deposited onto semiconductor device 1350 by way of PECVD. In the same or different examples, mesa passivation layer 1757 can be deposited via PECVD using an AMAT P5000.

Figure 19:
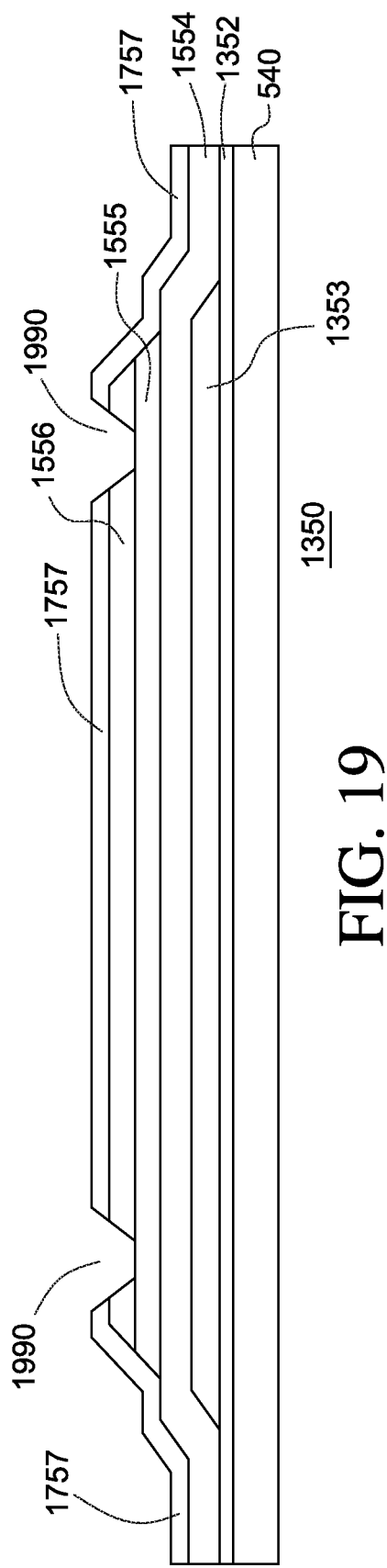
FIG. 19 illustrates a cross-sectional view of an example of the device build area of the semiconductor device of FIG. 13 after conducting one or more post-mesa passivation layer etches, according to the embodiment of FIG. 1.
Figure 20:
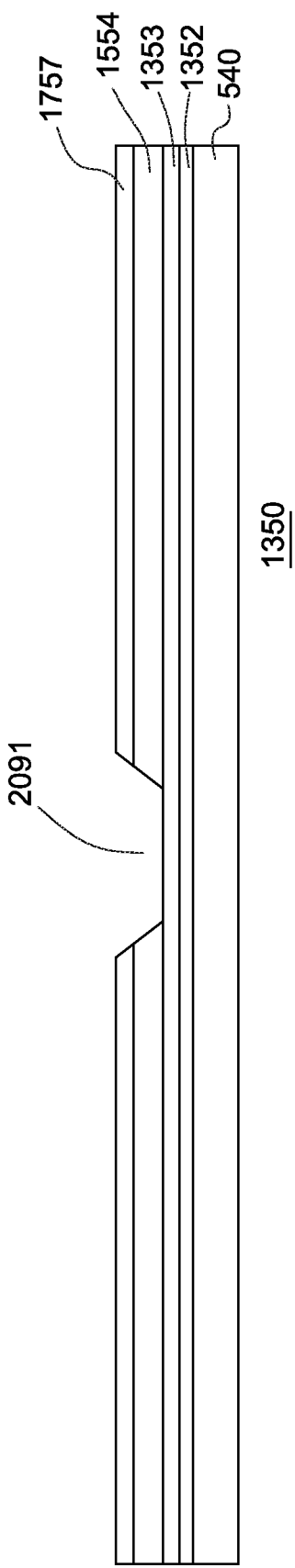
FIG. 20 illustrates a cross-sectional view of an example of the gate contact build area of the semiconductor device of FIG. 14 after conducting one or more post-mesa passivation layer etches, according to the embodiment of FIG. 1.

Referring again to FIG. 12, activity 1112 can comprise activity 1214 of conducting one or more post-mesa passivation layer etches. FIGS. 19 and 20 illustrate cross-sectional views of semiconductor device 1350 after one or more post-mesa passivation layer etches have been conducted. For example, FIG. 20 illustrates semiconductor device 1350 after a contact gate etch has taken place in the gate contact build region of semiconductor device 1350. In the same or different examples, FIG. 19 illustrates semiconductor device 1350 after a contact device etch has taken place in the device build region of semiconductor device 1350.

The contact gate etch of the gate contact build region of semiconductor device 1350 can etch away silicon nitride and/or silicon dioxide. For example, the contact gate etch can etch away mesa passivation layer 1757 and gate dielectric 1554. In many examples, metal gate layer 1353 underneath gate dielectric 1554 functions as an etch stop for the etching activity. The contact gate etch of the contact gate build region can be performed in a Tegal 903, manufactured by Tegal Corporation of Petaluma, Calif. After the contact gate etch, gate contact 2091 is formed on semiconductor device 1350. Gate contact 2091 is associated with gate contact area 2981 of FIG. 29.

The contact device etch of the device build region of semiconductor device 1350 can etch away silicon nitride and/or silicon dioxide. For example, the contact device etch can etch away mesa passivation layer 1757 and patterned IMD layer 1556. In some examples, the etchant used for the contact device etch can comprise a 10:1 BOE and/or a dry etchant, such as, for example, fluoroform ($CHF_3$) and oxygen ($O_2$). Patterned active layer 1555 under silicon nitride layer 1556 can act as an etch stop for the etching activity. After the contact device etch, contacts 1990 (FIG. 19) can be formed on semiconductor device 1350 as a result. Contacts 1990 (FIG. 19) are associated with device contact areas 2980 (FIG. 29). In this embodiment, the contact device etch and the contact gate etch can be separate etches using separate etch masks.

In many embodiments, after activity 1214, activity 1112 of FIG. 12 can be completed.

Figure 21:
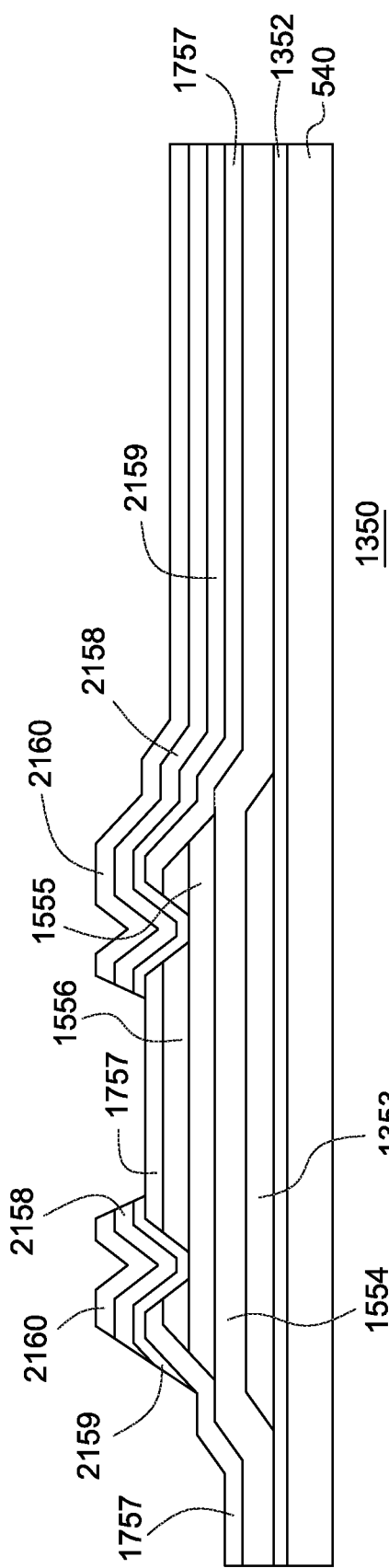
FIG. 21 illustrates a cross-sectional view of an example of the device build area of the semiconductor device of FIG. 13 after providing one or more contact elements, according to the embodiment of FIG. 1.
Figure 22:
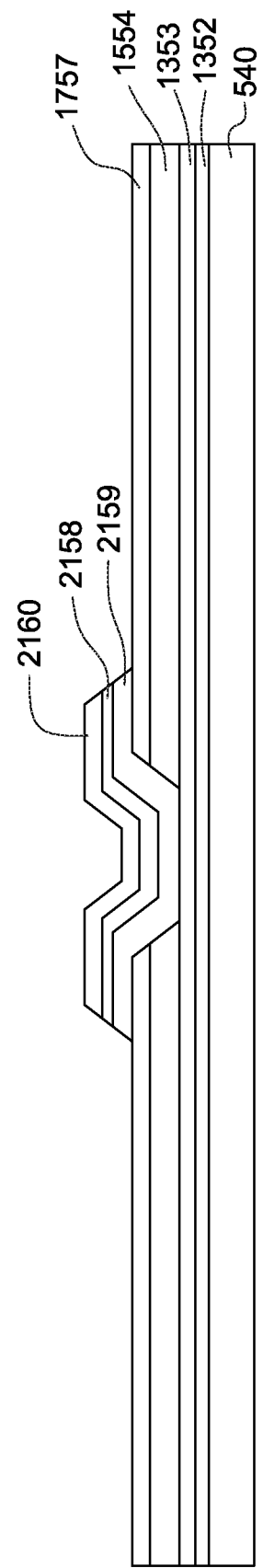
FIG. 22 illustrates a cross-sectional view of an example of the gate contact build area of the semiconductor device of FIG. 14 after providing one or more contact elements, according to the embodiment of FIG. 1.

Referring again to FIG. 11, activity 120 can comprise activity 1113 of providing one or more contact elements. FIG. 21 illustrates a cross-sectional view of a device build region of an example of semiconductor device 1350 after activity 1113 has been completed, according to the embodiment of FIG. 1. In addition, FIG. 22 illustrates a cross-sectional view of a gate contact build region of an example of semiconductor device 1350 after activity 1113 has been completed, according to the embodiment of FIG. 1.

In the example illustrated in FIG. 21, N+ a-Si layer 2159 can be provided over portions of mesa passivation layer 1757, patterned active layer 1555, and patterned IMD layer 1556. As illustrated in FIG. 21, diffusion barrier 2158 can be provided over N+ a-Si layer 2159, and metal layer 2160 can be provided over diffusion barrier 2158. Similarly, in the example of FIG. 22, N+ a-Si layer 2159 can be provided over portions of mesa passivation layer 1757, gate dielectric 1554, and gate metal layer 1353. Also shown in FIG. 22, diffusion barrier 2158 can be provided over N+ a-Si layer 2159, and metal layer 2160 can be provided over diffusion barrier 2158. In various embodiments, diffusion barrier 2158 and N+ a-Si layer 2159 can be omitted.

N+ a-Si layer 2159 may be provided by way of PECVD. As an example, N+ a-Si layer 2159 can be approximately 50 nanometers thick. In the same or different examples, N+ a-Si layer 2159 can be deposited via PECVD using an AMAT P5000.

As an example, diffusion barrier 2158 can comprise n-doped silicon. In these examples or other examples, diffusion barrier 2158 can comprise p-doped silicon. The phosphorous doped silicon can be configured to bridge the contact between metal layer 2160 and N+ a-Si layer 2159. In the same or different examples, metal layer 2160 can comprise silicon, phosphorous, boron, aluminum, neodymium, tantalum, chromium, niobium, tin, indium, zinc, molybdenum, titanium, zirconium, and/or hafnium. Further, metal layer 2160 can be doped with silicon and/or neodymium. In these or other examples, metal layer 2160 can be capped with molybdenum and/or tantalum. Capping metal layer 2160 can provide corrosion resistance for metal layer 2160. However, in other examples, metal layer 2160 can be devoid of tantalum.

Diffusion barrier 2158 can help prevent movement of atoms from metal layer 2160, such as, for example, aluminum atoms, from diffusing into N+ a-Si layer 2159, and subsequently patterned active layer 1555. Diffusion barrier 2158 and metal layer 2160 can be deposited over N+ a-Si layer 2159 by way of sputtering. In some examples, diffusion barrier 2158 and metal layer 2160 can be deposited using a KDF 744.

After, N+ a-Si layer 2159, diffusion barrier 2158, and metal layer 2160 have been deposited onto semiconductor device 1350, the three layers can be pattern etched. As an example, the three layers can be etched using a reactive ion etcher, such as, for example, an AMAT 8330. In some examples, N+ a-Si layer 2159, diffusion barrier 2158, and metal layer 2160 can be etched using a single etchant recipe for all three of the layers. As an example, N+ a-Si layer 2159, diffusion barrier 2158, and metal layer 2160 can be etched using boron trichloride ($BCl_3$) with a flow rate of approximately 140 sccm (standard cubic centimeters per minute) and chlorine gas ($Cl_2$) with a flow rate of approximately 10 sccm at a pressure of approximately 20 mTorr for 1 minute and 45 seconds. Next, the $Cl_2$ can be increased to 30 sccm, while the pressure can be dropped to 10 mTorr for 15 minutes. Next, the $BCl_3$ rate can be decreased to 30 sccm, and the pressure can be increased to 15 mTorr. Finally, the $BCl_3$ and the $Cl_2$ flow rates can be brought to zero, and oxygen ($O_2$) can be brought in at 50 sccm with a pressure of 50 mTorr for 60 minutes.

In many embodiments, activity 120 can comprise activity 1198 of providing a base dielectrical material. The base dielectric material can provide a uniform surface (e.g., a wetting layer) for the spin-on dielectric material (e.g., dielectric layer 2461 (FIG. 24)). In some examples, the base dielectric can comprise silicon oxide and/or silicon nitride. In many examples, the base dielectric can be provided using an activity similar or identical to the activity used to provide the second ILD dielectric material (i.e., activity 1117), as described below. In other embodiments, activity 1198 can be omitted. In some of these embodiments, activity 1198 can be replaced with an activity of providing a spin or spray on adhesion promoter.

In many embodiments, activity 120 can comprise activity 1114 of providing a first ILD dielectric material. The first ILD dielectric material can be provided over the contact element(s) of activity 1113. In some examples, the first ILD dielectric material can comprise an organic siloxane-based dielectric material, an organosiloxane dielectric material, and/or a siloxane-based dielectric material. In various embodiments, the first ILD dielectric material can be organic. Using an organic siloxane-based dielectric material can allow for thicker films and more flexible films than with a non-organic siloxane-based dielectric material. In some examples, the first ILD dielectric material can be used as an interlayer dielectric. In the other examples, the first ILD dielectric material can be used as an intralayer dielectric.

Table 1 illustrates properties of an example of a dielectric material that can be used as the first ILD dielectric material in activity 1114, according to the embodiment of FIG. 1.

TABLE 1

| Properties | Dielectric Material |
| --- | --- |
| Cure temperature | ~400° C. (when deposited over low temperature polysilicon) |
| | ~350° C. (when deposited over amorphous silicon (a-Si)) |
| | <200° C. (when deposited over a flexible substrate) |
| Film Thickness | 1.5 μm to 3.5 μm |
| Transmittance | >95% |

TABLE 1-continued

| Properties | Dielectric Material |
| --- | --- |
| Planarization | >95% |
| Resistance to plasma induced damage | Fluorine-based plasma (e.g., Sulfur hexafluorine ($SF_6$), carbon tetra fluorine ($CF_4$), trifluoromethane ($CHF_3$), $O_2$ plasma used for removing photoresist, and ashing |
| Adhesion | Aluminum (Al), chromium (Cr), indium tin oxide (ITO), silicon nitride (SiN), organic layers |
| Outgassing | Low (less than typical CVD chamber pressures) |
| Moisture uptake | Low moisture uptake |
| Dispense tool | Spin or slot die coaters, screen printers, spray coating |

As used in Table 1, film thickness can refer to the desired thickness of the dielectric material that displays the other properties in the table. Transmittance can refer to the percentage of light that is transmitted through the dielectric material. Planarization can refer to the degree of planarization (DOP) of the dielectric material. Resistance to plasma induced damage can indicate the plasmas that will not damage this film. Adhesion can mean the dielectric material can be coupled to at least these other materials. Outgassing can refer to outgassing pressure of the dielectric material or the rate at which the dielectric material outgases. Moisture uptake can refer to the rate at which moisture is absorbed by the dielectric material. Dispense tools can refer to equipment that can be used to apply the dielectric material.

Table 2 illustrates properties of a second example of a dielectric material that can be used as the first ILD dielectric material in activity 1114, according to the embodiment of FIG. 1.

TABLE 2

| Properties | Dielectric Material |
| --- | --- |
| Film Thickness | 1 μm to 4 μm |
| Cure temperature | ~180° C. |
| Etch Chemistry | Standard plasma etch chemistries |
| Etch Rate | >0.25 μm per minute |
| Feature Size | <5 μm |
| Dielectric Constant (k) | <4.0 |
| Breakdown Voltage | >5 megavolts per centimeter (MV/cm) |
| Heat Resistance | ≥250° C. |
| Adhesion | Al, ITO, molybdenum (Mo), photoresist |
| Moisture Uptake | <0.2 wt % over 2 hours |
| Planarization | >95% |
| Outgassing | No |
| Transparency | >95% |

As used in Table 2, etch chemistries can refer to etch chemistries that can be used to etch the dielectric material. Etch rate can be the minimum etch rate of the dielectric material when using the etch chemistries. Feature size can refer to the smallest size of an element or feature formed with the dielectric material. Breakdown voltage can be the voltage per length at which the dielectric material begins acting as a conductor. Heat resistance can be the lowest temperature that the material can withstand before becoming unstable.

In further embodiments, the first ILD dielectric material can comprise fluoropolymer, such as, for example, Asahi Al-X504 fluoropolymer manufactured by the Asahi Glass Co., Ltd. of Tokyo, Japan. The Asahi Al-X504 fluoropolymer can comprise similar or identical properties to those listed above in Table 1 and/or Table 2.

Figure 23:
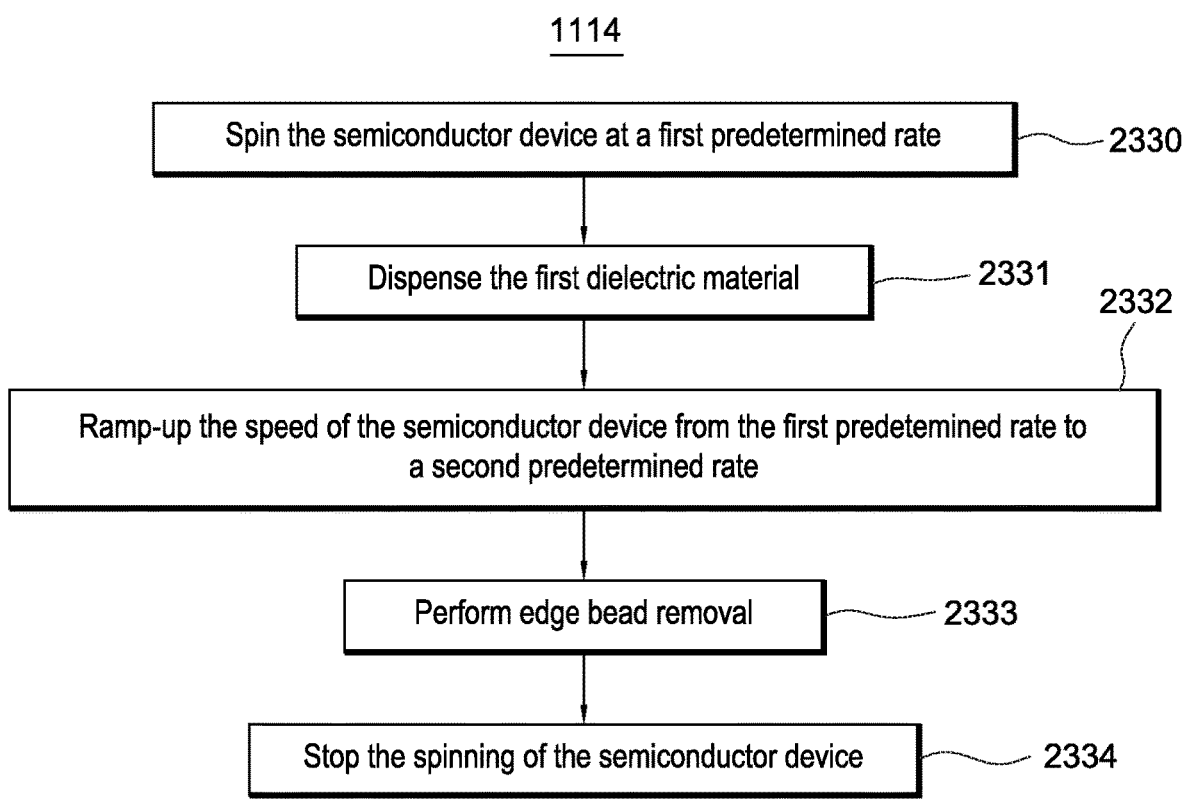
FIG. 23 illustrates an example of an activity of providing a first dielectric material, according to the embodiment of FIG. 1.

Turning ahead in the drawings, FIG. 23 illustrates an example of activity 1114 of providing a first ILD dielectric material. In various embodiments, the first ILD dielectric material can be a spin-on-dielectric. Accordingly, in these examples, the first ILD dielectric material can be applied to the semiconductor device by spin-coating the first ILD dielectric material over one or more of the contact element(s) described above with respect to activity 1113 (FIG. 11) (e.g., N+ a-Si layer 2159 (FIGS. 21 & 22), diffusion barrier 2158 (FIGS. 21 & 22), and/or metal layer 2160 (FIGS. 21 & 22)), the mesa passivation layer described above with respect to activity 1213 (FIG. 12) (e.g., mesa passivation layer 1757 (FIG. 17)), and/or the base dielectrical material described above with respect to activity 1198 (FIG. 11) (e.g., base dielectric material 2499 (FIG. 24)). In various embodiments, the application of the first ILD dielectric material can be performed in a Rite Track 8600 available from Rite Track, Inc., of West Chester, Ohio.

In many embodiments, activity 1114 can comprise activity 2330 of spinning the semiconductor device at a first predetermined rate. In some examples, the first predetermined spin rate can comprise greater than or equal to approximately 500 rpm and less than or equal to approximately 2000 rpm. In same or different embodiment, the first predetermined rate can comprise approximately 1000 rpm.

In many embodiments, activity 1114 can comprise activity 2331 of dispensing the first ILD dielectric material. In some examples, the first ILD dielectric material can be dispensed over the semiconductor device while the semiconductor device is spinning at the first predetermined rate. In some examples, the first ILD dielectric material can be dispensed using a syringe. For example, if the semiconductor device is a six inch diameter wafer, approximately 4 mL (milliliters) can be dispensed over the semiconductor device. In some examples, the pressure in the tip of the syringe during dispensing can be approximately 15 kPa. In the same or different embodiment, after the syringe dispenses the first ILD dielectric material, the syringe can comprise suck back pressure of approximately 1 kPa. The suck back pressure of the syringe can prevent dripping additional amounts of the first ILD dielectric material from the syringe after the dispensing activity is complete. For a 6-in wafer, the dispensing activity can take approximately 3 seconds. The semiconductor device can be spun at the first predetermined rate until activity 2331 is complete.

In various embodiments, a dynamic dispensing activity can be used. That is, the semiconductor device can be spinning while the first ILD dielectric material is dispensed. In some examples, the first ILD dielectric material can be dispensed at the center of the semiconductor device. In other examples, at the beginning of the dispensing activity, the syringe can be located over the center of the semiconductor device and can be moved from the center of the semiconductor device to the edge of the semiconductor device at a constant rate of approximately thirty to approximately sixty millimeters per second while the semiconductor device is spinning. In other embodiments, a static dispensing activity can be used. That is, the semiconductor device is not spun during the dispensing activity.

In many embodiments, activity 1114 can comprise activity 2332 of ramping-up the speed of the semiconductor device from the first predetermined rate to a second predetermined rate. In some examples, the second predetermined spin rate can be greater than or equal to approximately 2000 rpm and less than or equal to approximately 4000 rpm. In the same or different embodiment, the second predetermined rate can comprise approximately 2600 rpm. Spinning the semiconductor device at the second predetermined rate of approximately 2600 rpm for approximately thirty seconds can distribute the first ILD dielectric material with a thickness of approximately two μm over the surface of the semiconductor device. Different thicknesses of the first ILD dielectric material can be achieved by using different second predetermined rates.

Figure 30:
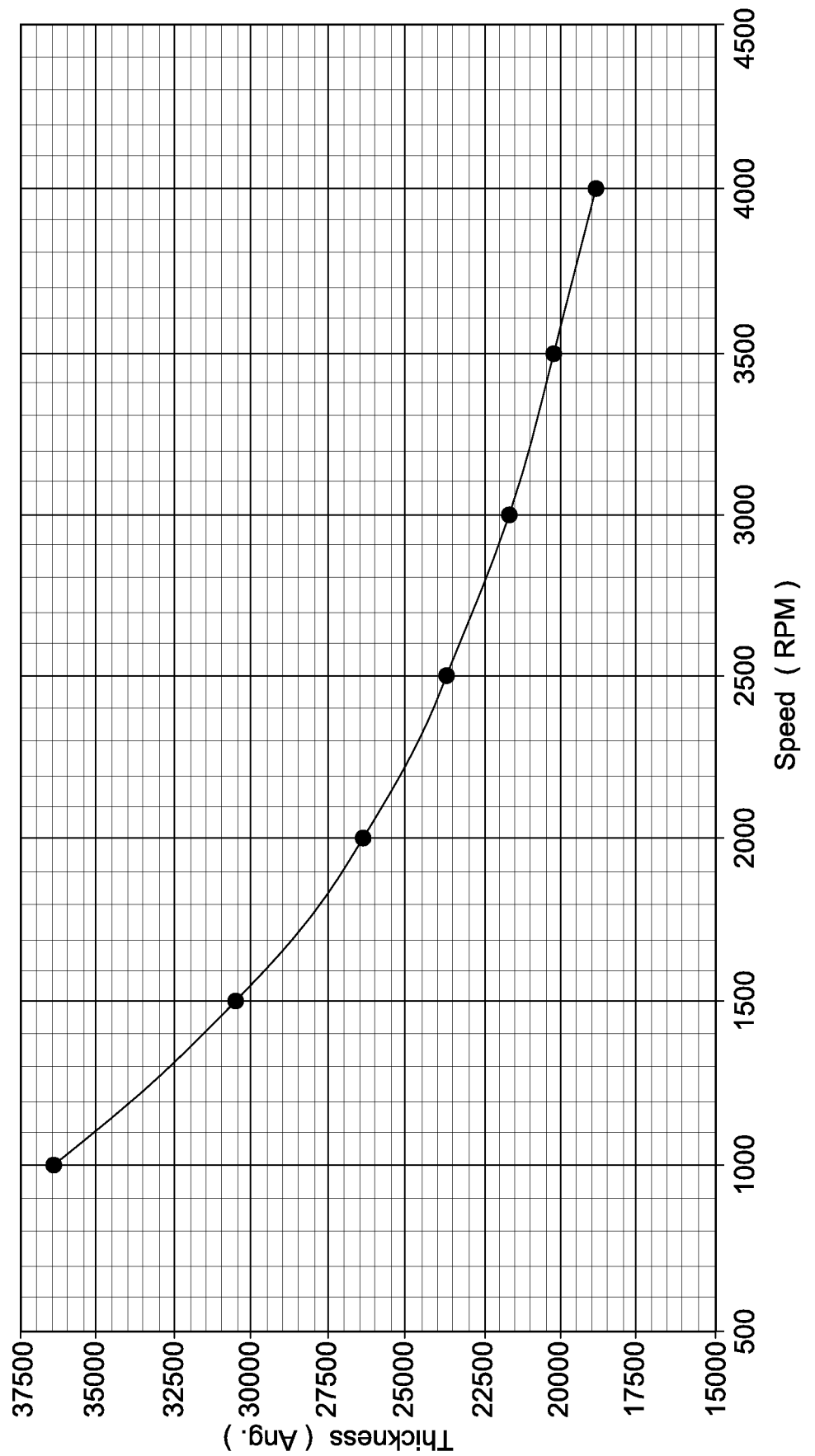
FIG. 30 illustrates a graph of thickness of a dielectric material versus spin rate of a substrate.

Turning ahead briefly in the drawings, FIG. 30 is an illustration of thickness of the first ILD dielectric material versus the spin rate (i.e., speed) of the semiconductor material.

Referring again to FIG. 23, activity 1114 can further comprise activity 2333 of performing edge bead removal. In some examples, during activities 2331 and 2332, the first ILD dielectric material can flow outward due to the centrifugal force toward the edge of the substrate and creating a ridge (i.e., the edge bead) on the top side edge of the semiconductor device. The edge bead, when dried, could flake off and increase defects of the semiconductor device and/or damage the manufacturing equipment. Accordingly, the edge bead is removed in activity 2333. In some examples, the equipment used in activities 2331 and 2332 can comprise an edge bead removal device. In some examples, a solvent is sprayed on the edge bead to remove the first ILD dielectric material around the edge of the substrate. In some examples, while the semiconductor device is spun at a third predetermined rate, a solvent can be sprayed over, for example, approximately five to approximately six millimeters inside the edge of the substrate. In some examples, removing the first ILD dielectric material from the edges of the substrate can also help to ensure that when a second ILD dielectric material is provided over the first ILD dielectric material (activity 1117 of FIG. 11), the edges of the first ILD dielectric material are capped by a second ILD dielectric material.

In some examples, cyclohexanone, propylene glycol monomethyl ether acetate (PGMEA), or other edge bead removing solvents can be used. In some examples, the semiconductor device is rotated at a third predetermined rate of approximately 1000 rpm during the edge bead removal activity. In some examples, the semiconductor device can be spun at the third predetermined rate for approximately thirty seconds, and solvent can be sprayed on the bead edge during this time.

In many embodiments, activity 1114 can comprise activity 2334 of stopping the spinning of the semiconductor device. In some embodiments, after the spinning of the semiconductor device is stopped, activity 1114 can be complete.

Referring back to FIG. 11, activity 120 can comprise activity 1115 of baking the semiconductor device. In some examples, baking the semiconductor device comprises baking the first ILD dielectric material of activity 1114, the contact element(s) of activity 1113, the first semiconductor element(s) of activity 1112, and the substrate assembly of activity 110 (FIG. 1). One of the purposes of the bake can be to cause evaporation of the solvents from the edge bead activity. Baking the semiconductor device can also increase planarization, decrease film defects, and cross-link the first ILD dielectric material.

In various embodiments, the baking of the semiconductor device can be performed using a one or two bake sequence. The baking activity can be performed at atmospheric pressure using one or more hot plates. Activity 1115 can be performed, for example, in a Rite Track 8800.

The first bake can be a bake for approximately sixty seconds at approximately 160° C. In an alternative example, the first bake can be an approximately sixty second bake at approximately 150° C. After the first bake is complete, in some examples, the semiconductor device can be allowed to cool for approximately thirty seconds before the second bake. The semiconductor device can be allowed to cool at room temperature (and not using a chill plate). The semiconductor device can be allowed to cool, in these examples, because the handling system uses polytetrafluoroethylene (e.g., Teflon® material from E. I. du Pont de Nemours and Company of Wilmington, Del.) coated chucks to handle the semiconductor device. Placing a hot semiconductor device on the polytetrafluoroethylene coated chuck can damage the chuck. If other equipment is used, the cooling activity can possibly be omitted.

After letting the semiconductor device cool, the semiconductor device can be baked for a second time on a hot plate. In some embodiments, the second bake can be for approximately sixty seconds at a temperature greater than approximately 160° C. because 160° C. is the boiling point of PGMEA. For example, if the first bake was at the 160° C., the second bake can be for approximately sixty seconds at approximately 170° C. If the first bake was at the 150° C., the second bake can be for approximately sixty seconds at approximately 200° C. After the second bake is complete, the semiconductor device can be cooled again for thirty seconds. In other embodiments, other sequences of bakes can be performed.

In other examples, the bake can be a single bake for approximately 1 to approximately 10 minutes at a temperature of greater than or equal to approximately 150° C. and less than or equal to approximately 200° C.

After the baking is complete, the next activity in activity 120 (FIG. 1) can comprise activity 1116 of curing the first ILD dielectric material. Curing of the first ILD dielectric material can improve the cross-linking of the first ILD dielectric material. In some examples, the curing can be performed in a convection oven in a nitrogen atmosphere at atmospheric pressure (i.e., approximately one atmosphere).

In various examples, the semiconductor device can be placed in the oven. Afterwards, the temperature in the oven can be ramped-up to approximately 200° C., and the semiconductor device can be baked for approximately one hour at approximately 200° C. The temperature can be ramped-up at a rate of approximately 1-2° C. per minute to minimize outgassing of the first ILD dielectric material of activity 1114. After the bake is complete, the temperature can be slowly ramped down (e.g., 1-2° C. per minute) to room temperature.

In another embodiment, a baking activity with five separate bakes can be used. The first bake can be a bake at approximately 60° C. for approximately ten minutes. The ramp-up time to approximately 60° C. from room temperature is approximately ten minutes. After baking at approximately 60° C., the temperature is ramped-up over approximately thirty-two minutes to approximately 160° C. The semiconductor device is baked for approximately thirty-five minutes at approximately 160° C.

The temperature of the convection oven then can be increased to approximately 180° C. over approximately ten minutes after the 160° C. bake. The semiconductor device can be baked for approximately twenty minutes at approximately 180° C.

After baking at 180° C., the temperature can be ramped-up over approximately fifty minutes to approximately 200° C. The semiconductor device can be baked for approximately sixty minutes at approximately 200° C. Finally, in this bake activity, the temperature in the oven can be ramped-down to approximately 60° C. over approximately seventy minutes. The semiconductor device can be baked for approximately ten minutes at approximately 60° C. After baking is complete, the semiconductor device can be allowed to cool to approximately room temperature before proceeding with activity 120 of FIG. 11. The baking of the semiconductor device can help anneal the one or more contact elements.

In still other examples, the semiconductor device can be placed in a nitrogen oven with various ramp rates reaching an eventual soak at approximately 200° C. for approximately one hour.

In many embodiments, activity 120 can comprise activity 1117 of providing a second ILD dielectric material. In some examples, providing the second ILD dielectric material can comprise depositing the second ILD dielectric material over the first ILD dielectric material (e.g., first dielectric material 2461 (FIG. 24)). In some examples, the second dielectric material can comprise silicon nitride. In the same or different examples, the second ILD dielectric material can comprise silicon oxynitride ($SiO_xN_y$), silicon oxide, and/or silicon dioxide ($SiO_2$). In some examples, the second ILD dielectric material can be deposited over the first ILD dielectric material by way of low temperature PECVD. In some examples, as part of providing the second ILD dielectric material, the first ILD dielectric material can be capped by the second ILD dielectric material. In some examples, the edges of the first ILD dielectric material can be capped by the second ILD dielectric material so the first ILD dielectric material is not exposed to any subsequent oxygen ($O_2$) plasma ashings. Oxygen plasma ashings can degrade the first ILD dielectric material in some examples.

The second ILD dielectric material can be deposited with a thickness of greater than or equal to approximately 100 nanometers to less than or equal to approximately 300 nanometers. The second ILD dielectric material can be deposited to protect the first ILD dielectric material from later etches.

In many embodiments, activity 120 can comprise activity 1118 of providing a mask over the second ILD dielectric material. The mask applied in activity 1118 can be an etch mask for an etching activity of activity 1119 of FIG. 11.

In some examples, activity 1118 can comprise applying a patterned photoresist over the first ILD dielectric material (e.g., first ILD dielectric material 2461 (FIG. 24)) or patterning a mask over the first ILD dielectric material (e.g., first dielectric material 2461 (FIG. 24)). Similarly, activity 1118 can comprise providing a patterned mask over the first ILD dielectric material (e.g., first dielectric material 2461 (FIG. 24)).

In some examples, the mask covers one or more portions of the first ILD dielectric material and the second ILD dielectric material that are not to be etched. The mask can be provided with a thickness such that the mask is not etched through during the etching activity of activity 1119 of FIG. 11. In some examples, the mask can comprise a thickness of greater than or equal to approximately 250 nanometers and less than or equal to approximately 500 nanometers, such as, for example, 350 nanometers.

In some examples, the mask comprises photoresist. In some examples, the photoresist can be AZ Electronic Materials MiR 900 Photoresist, manufactured by AZ Materials of Luxembourg, Luxembourg. In some examples, the photoresist is coated over the second ILD dielectric material using the Rite Track 8800. For example, the semiconductor device can be vapor primed and spin-coated with the mask (e.g., the photoresist). After coating the semiconductor device, the semiconductor device can be baked at approximately 105° C. for approximately sixty seconds.

Next, the semiconductor device can be aligned to the correct position with a template and exposed to UV (ultraviolet) light to transfer the mask image from the template to the mask. After exposing the mask, the semiconductor device can be baked for approximately ninety seconds at approximately 110° C. The mask can be then developed using an approximately ninety second puddle with standard development chemicals to remove the portions of the photoresist that were not exposed to the UV light.

After the development is completed, the last portion of providing the mask over the second ILD dielectric material can comprise performing a photoresist reflow activity on the mask. Photoresist reflow is the activity of heating the mask after the photoresist has been developed to cause the photoresist to become at least semi-liquid and flow.

In some examples, the semiconductor device can be baked at approximately 140° C. for approximately sixty seconds. This photoresist reflow activity will decrease the sharpness of the edges of the mask, and thus, when etched in activity 1119 of FIG. 11, the vias in the first dielectric and the second dielectric can comprise sloped sides. In some examples, the sloped sizes can be at an angle of approximately thirty degrees from horizontal.

In many embodiments, activity 120 can comprise activity 1119 of etching the base dielectric material, the first ILD dielectric material, and/or the second ILD dielectric material. The base dielectric material, the first ILD dielectric material, and/or the second ILD dielectric material can be etched to create vias in the base dielectric material, the first ILD dielectric material, and/or the second ILD dielectric material.

In some examples, the base dielectric material, the first ILD dielectric material, and/or the second ILD dielectric material can be etched in the same activity using the same etch mask. In other examples, the first ILD dielectric material can be etched in a first activity, and the second ILD dielectric material can be etched in a second activity, and the base dielectric can be etched in a third activity, in any applicable and/or suitable order.

In these other examples, a mask can be applied to the base dielectric material; the base dielectric material can be etched; and the mask can be removed before the first ILD dielectric material is provided in activity 1114 of FIG. 11. Subsequently, a mask can be applied to the first ILD dielectric material; the first ILD dielectric material can be etched; and the mask can be removed before the second ILD dielectric material is provided in activity 1118 of FIG. 11. Then, a mask can be applied to the second ILD dielectric material, and the second ILD dielectric material can be etched. In another example, the second ILD dielectric material can be etched using the mask of activity 1118; the mask can be removed; and the patterned second ILD dielectric material can be used as the mask for patterning the first ILD dielectric material.

In many embodiments, the base dielectric material, the first ILD dielectric material, and/or the second ILD dielectric material are plasma etched. In the same or different embodiments, the base dielectric material, the first ILD dielectric material, and/or the second ILD dielectric material can be reactive ion etched (RIE). In some examples, the base dielectric material, the first ILD dielectric material, and/or the second ILD dielectric material can be etched with a fluorine-based etchant. In some examples, the etchant can be trifluoromethane ($CHF_3$), sulfur hexafluoride ($SF_6$), and/or any other suitable fluorine-based etchant(s).

In some examples, where there is no base dielectric material (i.e., activity 1198 is omitted), the first material can comprise the organosiloxane dielectric material described previously, and the second material can comprise silicon nitride. In these examples, the first ILD dielectric material and the second ILD dielectric material can be RIE etched with sulfur hexafluoride ($SF_6$) for approximately four minutes. If sulfur hexafluoride is used as the etchant, the etching can be performed in a plasma chamber with a 1:2 ratio of sulfur hexafluoride to oxygen ($O_2$).

The etch rate of the sulfur hexafluoride for the first ILD dielectric material and the second ILD dielectric material are approximately the same (i.e., approximately 500 nanometers per minute). The etch rate of the second ILD dielectric material, however, can be marginally greater than the first ILD dielectric material. In some example, the pressure in the plasma chamber during etching can be greater than or equal to approximately 50 mTorr and less than or equal to approximately 400 mTorr. The RIE etch can be performed in a Tegal 901, manufactured by Tegal Corporation of Petaluma, Calif.

The second ILD dielectric material can be etched before the first ILD dielectric material; the first ILD dielectric material can be etched before the base dielectric material. In many examples, the metal layer underneath the base dielectric material functions as an etch stop for the etching activity. If sulfur hexafluoride is used as the etchant, the metal layer can comprise aluminum. In this embodiment, the metal layer of can be devoid of molybdenum and/or tantalum because sulfur hexafluoride etches these two metals. In a different embodiment, the metal layer can comprise molybdenum and/or tantalum if the etch for the overlying second dielectric layer is a timed etch.

Figure 24:
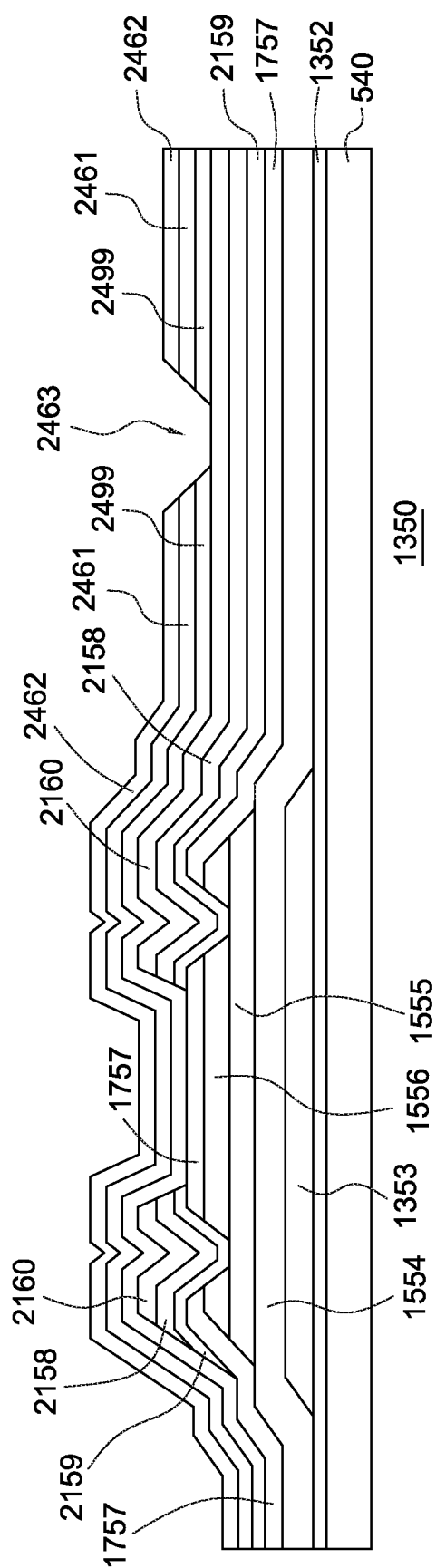
FIG. 24 illustrates a cross-sectional view of an example of the device build area of the semiconductor device of FIG. 13 after etching a base dielectric material, a first dielectric material, and a second dielectric material, according to the embodiment of FIG. 1.

A buffered oxide etch (BOE) and chlorine based etchants is not be used in some examples because such etchants do not etch the first ILD dielectric material when it comprises an organosiloxane dielectric material. FIG. 24 illustrates a cross-sectional view of the device build area of an example of semiconductor device 1350 after etching etch base dielectric material 2499, first dielectric material 2461, and second dielectric material 2462, according to the embodiment of FIG. 1. After activity 1119 in FIG. 11, semiconductor device 1350 can comprise vias 2463, as shown in FIG. 24. Vias 2463 can be associated with via area 2982 (FIG. 29). The mask over second dielectric layer 2462 is not shown in FIG. 24

In many embodiments, activity 120 can comprise activity 1120 of removing the mask. In some examples, the mask can be removed by ashing the mask (e.g., the photoresist) at a temperature below 110° C. If the mask is ashed at a temperature above 110° C., cracking can occur in the first ILD dielectric material. Accordingly, in some examples, ashing of the mask can be performed at a temperature greater than or equal to approximately 70° C. and less than or equal to approximately 90° C. In the same or different example, the ashing of the mask can be performed at a temperature greater than or equal to approximately 77° C. and less than or equal to approximately 84° C.

The ashing can be performed at a pressure of no greater than approximately 300 mTorr. Oxygen ($O_2$) can flow through in the chamber during the ashing activity at a rate of approximately 50 sccm. In various examples, the ashing activity can be performed in a Tegal 901. After ashing the mask, the semiconductor device can be rinsed with deionized water and spin dried. In some examples, the rinsing can be performed in a quick dump rinser, and the drying can be performed in a spin rinse dryer.

In other examples, a wet strip can be used to remove the photoresist. In some embodiments, an N-methyl pyrolidinone (NMP) based stripper can be used.

In some embodiments, activity 1198 and/or activity 1117 can be omitted.

In many examples, further details regarding the techniques described with respect to activity 1198 (FIG. 11) and activities 1114-1121 (FIG. 11) are provided in United States Patent Application Publication No. 20110227203, which published on Sep. 22, 2011, and U.S. Pat. No. 8,383,520, which issued on Feb. 26, 2013. Accordingly, United States Patent Application Publication No. 20110227203 and U.S. Pat. No. 8,383,520 each are incorporated herein by reference in their entirety.

In many embodiments, activity 120 can comprise activity 1121 of providing one or more second semiconductor elements. At least part of performing activity 1121 can comprise providing a photodiode. The photodiode can comprise a passive pixel PIN diode sensor. Accordingly, exemplary second semiconductor element(s) can comprise a second metal layer, an indium tin oxide (ITO) layer, and a silicon nitride layer. Further exemplary second semiconductor element(s) can comprise an N-type layer, an intrinsic (I) layer, and a P-type layer.

Figure 25:
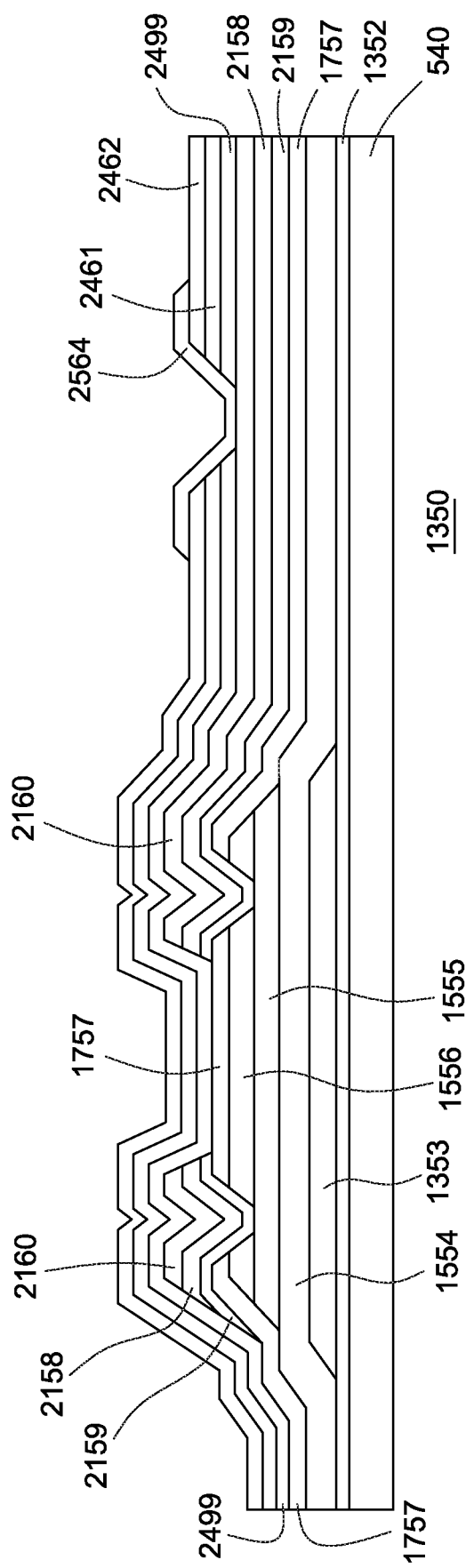
FIG. 25 illustrates a cross-sectional view of an example of the device build area of the example of the semiconductor device of FIG. 13 after providing an N-type layer, according to the embodiment of FIG. 1.

As an example, FIG. 25 illustrates a cross-sectional view of the device build area of an example of semiconductor device 1350 after providing N-type layer 2564, according to the embodiment of FIG. 1. N-type layer 2564 can be deposited over second dielectric material 2462 and at least partially in vias 2463 (FIG. 24), including, for example, second dielectric material 2462 (FIG. 24), first dielectric material 2461 (FIG. 24), base dielectric material 2499 (FIG. 24), and/or metal layer 2160 (FIG. 21). In some examples, N-type layer 2564 can be deposited by sputtering using a KDF 744. N-type layer 2564 can define the pixel of the photodiode described above with respect to activity 1121 (FIG. 11).

N-type layer 2564 can comprise aluminum, silicon, neodymium, tantalum, molybdenum, chromium, titanium, and/or tungsten, which can be deposited using a KDF 744. N-type layer 2564 can be capped with phosphorous doped silicon or any other suitable N-doped material. N-type layer 2564 can be configured and/or structured (i) to provide stable, ohmic contact with diffusion barrier 2158 (FIG. 21) and/or (ii) to provide a selectivity of approximately 10:1 or greater for subsequent etchings. Further, N-type layer 2564 can be greater than or equal to approximately 50 nanometers thick and less than or equal to approximately 200 nanometers thick, such as, for example, approximately 150 nanometers thick.

N-type layer 2564 can be pattern etched, such as, for example, with a dry etchant. For example, the dry etchant can comprise chlorine and boron trichloride. N-type layer 2564 can be etched using an AMAT 8330.

Figure 26:
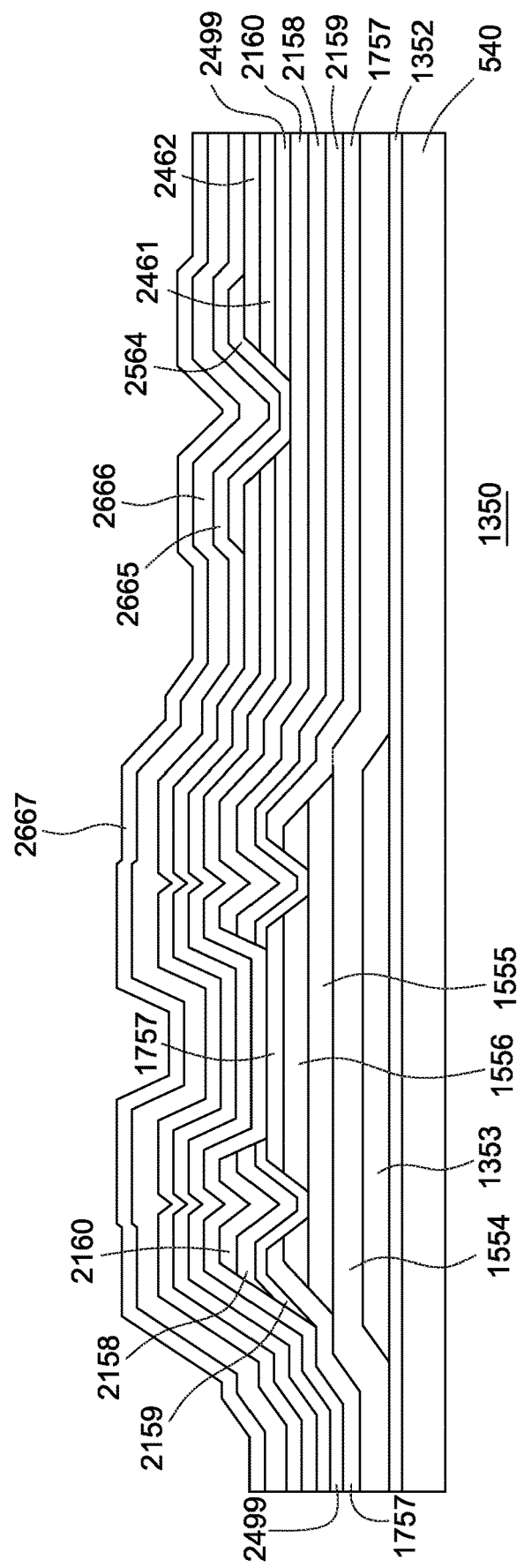
FIG. 26 illustrates a cross-sectional view of an example of the device build area of the example of the semiconductor device of FIG. 13 after providing an intrinsic layer, a P-type layer, and an ITO layer, according to the embodiment of FIG. 1.

As an example, FIG. 26 illustrates a cross-sectional view of the device build area of an example of semiconductor device 1350 after providing I layer 2665, P-type layer 2666, and ITO layer 2667, according to the embodiment of FIG. 1. I layer 2665 can be deposited over N-type layer 2564; P-type layer 2666 can be deposited over I layer 2665; and ITO layer 2667 can be deposited over P-type layer 2666.

I layer 2665 can be deposited onto semiconductor device 1350 by way of PECVD, such as, for example, (i) using an AMAT P5000 and/or AKT 1600, both being manufactured by Applied Materials, Inc. of Santa Clara, Calif., and/or (ii) using silane ($SiH_4$) and hydrogen ($H_2$) precursor gases. I layer 2665 can be configured such that film stress in I layer 2665 is minimized to prevent semiconductor 1350 from bowing after performing activity 130 (FIG. 1), as described below. The ratio of hydrogen and silane precursor gases can be adjusted to control and/or tune the film stress in I layer 2665. Decreasing the ratio of hydrogen to silane increases (i.e., makes more positive) the film stress. Further, reducing the power, increasing the pressure, and/or increasing the susceptor spacing can increase the film stress. In many examples, the film stress in I layer 2665 can be controlled and/or tuned such that the film stress is greater than or equal to approximately −150 MPa (MegaPascals) and less than or equal to approximately −50 MPa.

I layer 2665 can be deposited using an electrode (e.g., a 470 by 370 millimeter electrode) with an electrical power of 75 Watts±50 percent. In these or other examples, the power density can comprise approximately 43.1 milliWatts per square centimeter. The susceptor spacing for the deposition can be approximately 24.43 millimeters±50 percent. The susceptor spacing can affect the deposition rate, film characteristics, uniformity, stress, etc. of I layer 2665. Further, I layer 2665 can be deposited onto semiconductor device 1350 at a pressure of approximately 2.5 Torr±50 percent and/or at a temperature of approximately 200° C., such as, for example, for a time of approximately 3600 seconds±50 percent. The silane and hydrogen precursor gases can be provided at flow rates of 100 sccm±50 percent (standard cubic centimeters per minute) and 1800 sccm±50 percent, respectively. Where these values are bounded within a range of ±50 percent, the value can be chosen based on the lateral dimensions of the substrate assembly. That is, the lateral dimensions of the substrate assembly can impact the film stress in the I layer such that these parameters can be tuned and/or adjusted to accommodate the particular substrate assembly.

I layer 2665 can comprise intrinsically doped silicon and/or undoped amorphous silicon (a-Si). Further, I layer 2665 can be greater than or equal to approximately 100 nanometers thick and less than or equal to approximately 150 nanometers thick, such as, for example, approximately 120 nanometers thick. In other embodiments, I layer 2665 can be approximately 1200 nanometers thick.

P-type layer 2666 can be deposited onto semiconductor 1350 by way of PECVD, such as, for example, using an AMAT P5000 and/or using silane ($SiH_4$), hydrogen ($H_2$), and diborane ($B_2H_6$) precursor gases. In some examples, P-type layer 2666 can be deposited in the same chamber (e.g., the same AMAT P5000) as I layer 2665.

P-type layer 2666 can comprise boron doped silicon. P-type layer 2666 can be configured to permit electrical contact between I layer 2665 and ITO layer 2667 while also maintaining reasonable light transmissivity through P-type layer 2666. Accordingly, P-type layer 2666 can be greater than or equal to approximately 5 nanometers and less than or equal to approximately 20 nanometers.

ITO layer 2667 can be deposited over P-type layer 2666. In some examples, ITO layer 2565 can be deposited by sputtering using a KDF 744.

ITO layer 2667 can comprise indium tin oxide and can be greater than or equal to approximately 25 nanometers thick and less than or equal to approximately 50 nanometers thick. At this thickness, ITO layer 2667 can comprise a sheet resistance of approximately 160 Ohms/square. In general, the thickness of ITO layer 2667 can be balanced to maximize the light transmissivity of ITO layer 2667 and to minimize the sheet resistance.

In some examples, I layer 2665, P-type layer 2666, and ITO layer 2667 can be pattern etched. As an example, I layer 2665, P-type layer 2666, and ITO layer 2667 can be etched using an AMAT 8330. Etching I layer 2665 can undercut ITO layer 2667 leaving an overhang after the etch. In some examples, ITO layer 2667 can be etched with buffered hydrofluoric (HF) acid to remove the overhang. In these examples, ITO layer 2667 can be etched with buffered hydrofluoric acid while the photoresist for the patterned etch remains in place. Subsequently, the photoresist for the patterned etch can be removed.

Figure 32:
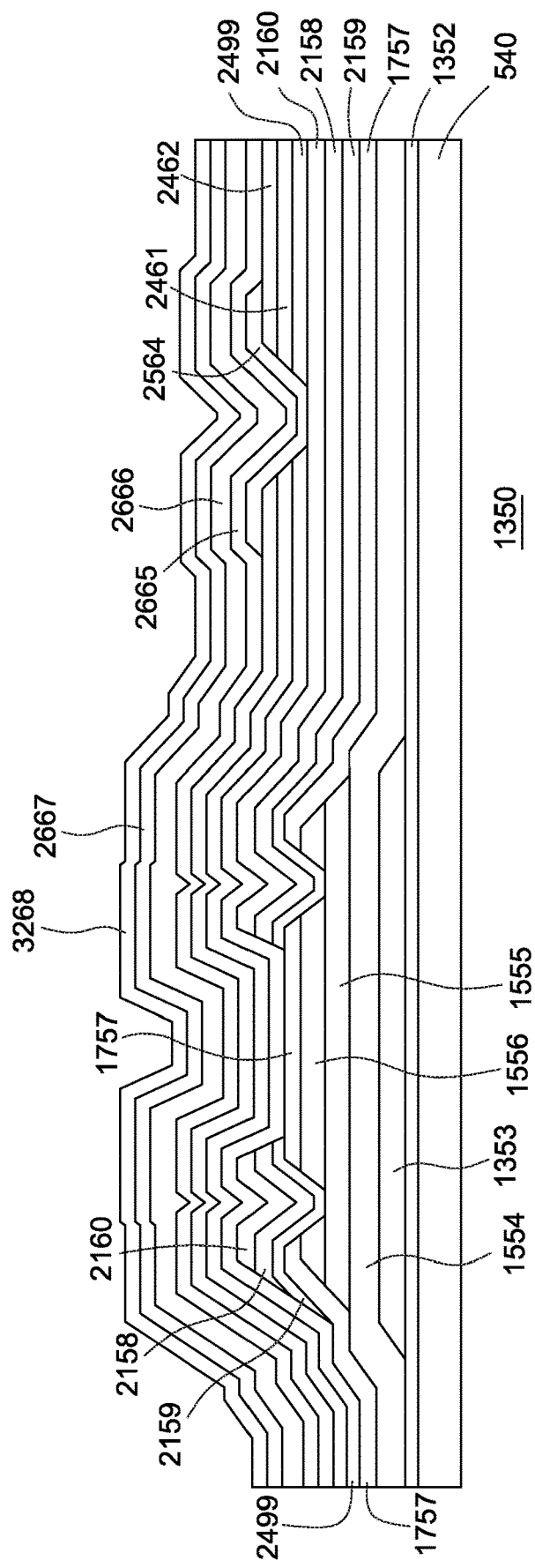
FIG. 32 illustrates a cross-sectional view of an example of the device build area of the example of the semiconductor device of FIG. 13 after providing a silicon nitride layer, according the embodiment of FIG. 1.

FIG. 32 illustrates a cross-sectional view of the device build area of an example of semiconductor device 1350 after providing silicon nitride layer 3268, according to the embodiment of FIG. 1. Silicon nitride layer 3268 can be deposited over ITO layer 2667 and can be approximately 100 nanometers thick. In some examples, silicon nitride layer 3268 can be deposited via PECVD using an AMAT P5000. In the same or other examples, silicon nitride layer 3268 can be etched using a Tegal 901, with ITO layer 2667 being the stop layer. In some embodiments, silicon nitride layer 3268 can be omitted.

A second metal layer can be deposited over ITO layer 2667 and/or silicon nitride layer 3268. The second metal layer can be similar or identical to metal layer 2160 (FIGS. 21, 22, 24-26, & 32). In many embodiments, the second metal layer can be coupled (e.g., electrically coupled) to metal layer 2160 (FIGS. 21, 22, 24-26, & 32).

After activity 1121, activity 120 can be complete.

Turning back to FIG. 1, method 100 can comprise activity 130 of removing the flexible substrate, including the semiconductor elements coupled to the flexible substrate, from the carrier substrate. Activity 130 can be performed when the substrate assembly comprises a flexible substrate. When the substrate assembly comprises a rigid substrate but not a flexible substrate, activity 130 can be omitted. In some examples, the flexible substrate can be removed from the carrier substrate by peeling the flexible substrate from the carrier substrate by hand. A razor blade can be inserted at the interface between the carrier substrate and the flexible substrate and moved toward the center of the flexible substrate to facilitate peeling the flexible substrate from the carrier substrate.

Other suitable techniques for removing the flexible substrate from the carrier substrate are described in U.S. Pat. No. 8,120,662, which issued on Feb. 21, 2012, United States Patent Application Publication No. 20100297829, which published on Nov. 25, 2010, U.S. Pat. No. 8,992,712, which issued Mar. 31, 2015, and U.S. Pat. No. 9,076,822, which issued Jul. 7, 2015. U.S. Pat. No. 8,120,662, United States Patent Application Publication No. 20100297829, U.S. Pat. Nos. 8,992,712, and 9,076,822 each are incorporated herein by reference in their entirety.

Figure 27:
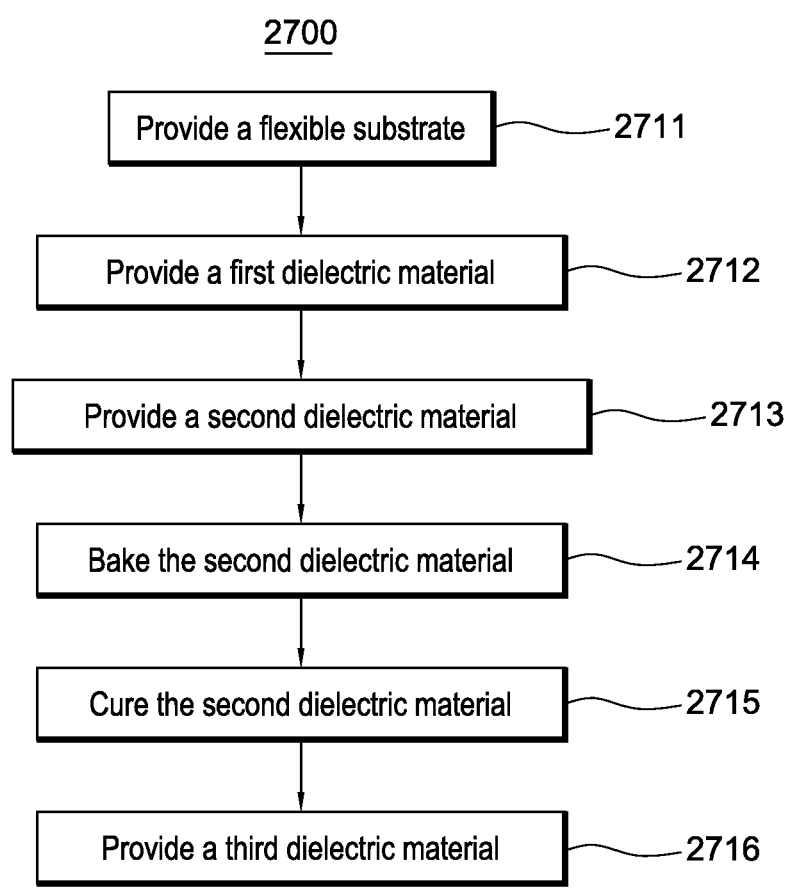
FIG. 27 illustrates an example of a method of planarizing a flexible substrate, according to another embodiment.

Turning to another embodiment, FIG. 27 illustrates an example of method 2700 of planarizing a flexible substrate. In the same or different embodiments, method 2700 can be considered a method of etching an organosiloxane dielectric material. Method 2700 can also be considered a method of etching an organic siloxane-based dielectric or a method of etching a siloxane-based dielectric material. Method 2700 is merely exemplary and is not limited to the embodiments presented herein. Method 2700 can be employed in many different embodiments or examples not specifically depicted or described herein.

Referring to FIG. 27, method 2700 can comprise activity 2711 of providing a flexible substrate. Activity 2711 can be similar or identical to activity 211 of FIG. 2. The flexible substrate can be similar or identical to flexible substrate 450 of FIG. 4. In yet other embodiments, activity 2711 can be similar or identical to activity 110 of FIG. 1, and the flexible substrate can be similar or identical to flexible substrate 450, which can be a portion of substrate assembly 540.

Method 2700 can continue with activity 2712 of providing a first flexible substrate dielectric material. In some examples, the first flexible substrate dielectric material can be similar or identical to second dielectric material 2462 of FIG. 24. Further, activity 2712 can be similar or identical to activity 1117 of FIG. 11.

The next activity in method 2700 can comprise activity 2713 of providing a second flexible substrate dielectric material. The second flexible substrate dielectric material can be similar or identical to first dielectric material 2461 of FIG. 24. Activity 2713 can be similar or identical to activity 1114 of FIG. 11.

Method 2700 can continue with activity 2714 of baking the second flexible substrate dielectric material. In some examples, activity 2714 can be similar or identical to activity 1115 of FIG. 11.

Subsequently, method 2700 can comprise activity 2715 of curing the second dielectric material. In some examples, activity 2715 can be similar or identical to activity 1116 of FIG. 11.

In other examples, a different baking activity with five separate bakes in a convection oven can be used. The first bake can be a bake at approximately 40° C. for approximately ten minutes. The ramp-up time from room temperature to approximately 40° C. can be approximately two minutes. After baking at 40° C., the temperature can be ramped-up over approximately thirty-two minutes to approximately 160° C. Then, the flexible substrate is baked for approximately thirty-five minutes at approximately 160° C.

The temperature of the convection oven is then increased to approximately 180° C. over approximately ten minutes after the 160° C. bake. The flexible substrate is baked for approximately twenty minutes at approximately 180° C.

After baking at 180° C., the temperature is ramped-up over approximately fifty minutes to approximately 230° C. Alternatively, the temperature is ramped-up at approximately 2° C. per minute to approximately 230° C. The flexible substrate is baked for approximately fifteen hours at approximately 230° C.

Finally, in this bake activity, the temperature in the oven is ramped-down to approximately 60° C. over approximately eighty-five minutes. The flexible substrate is baked for approximately ten minutes at approximately 60° C. After baking is complete, the flexible substrate is allowed to cool to approximately room temperature before proceeding with method 2700 of FIG. 27.

Method 2700 can continue with activity 2716 of providing a third flexible substrate dielectric material. In some examples, the third flexible substrate dielectric material can be greater than or equal to approximately 200 nanometers thick and less than or equal to approximately 400 nanometers, such as, for example, 300 nanometers thick. The third flexible substrate dielectric material can comprise silicon nitride. After depositing the third flexible substrate dielectric material, the flexible substrate can be in-situ baked for approximately five minutes at approximately 180° C. In some examples, the third flexible substrate dielectric material can be similar or identical to passivation layer 1352 (FIG. 13).

Figure 28:
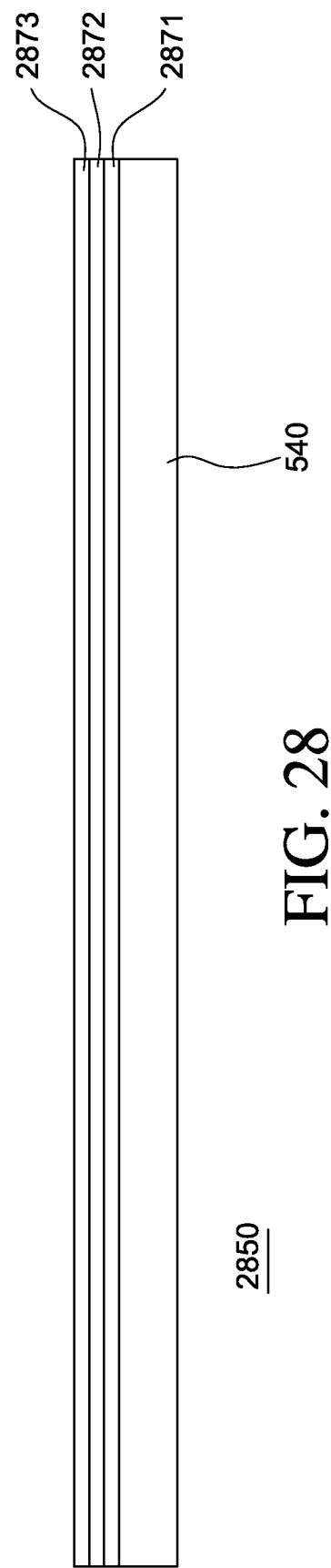
FIG. 28 illustrates a cross-sectional view of an example of a semiconductor device according to the method of FIG. 27, according to the embodiment of FIG. 27.

FIG. 28 illustrates an example of semiconductor device 2850 after providing the third flexible substrate dielectric material, according to the second embodiment. In these examples, first dielectric material 2871 can be provided over flexible substrate assembly 540. Second dielectric material 2872 can be provided over first dielectric material 2871, and third dielectric material 2873 can be provided over second dielectric material 2872.

After providing the third flexible substrate dielectric layer, method 2700 can be complete. The resulting semiconductor device (e.g., semiconductor device 2850 (FIG. 28)) can be used as the flexible substrate provided in activity 110 (FIG. 1). However, in some embodiments, the flexible substrate provided in activity 110 can be provided without performing method 2700.

In various examples, the semiconductor device of method 100 of FIG. 1 (e.g., semiconductor device 1350 (FIGS. 13-22, 24-26, 29, & 32)) can comprise an average effective saturation mobility of 19.7 cm$^2$/V-s, an average drive current of approximately 57.5 microAmps/(Width/Length), an average threshold voltage shift of 0.55 volts under positive and negative gate bias direct current (DC) stress for 10,000 seconds, an average subthreshold slope of 0.22 volts/decade, and a reverse bias leakage current of approximately 1 femtoAmp/micrometer. Further, in some examples, the semiconductor device of method 100 of FIG. 1 (e.g., semiconductor device 1350 (FIGS. 13-22, 24-26, 29, & 32)) can comprise a leakage current of less than or equal to approximately 10 picoAmps/mm$^2$. In many examples, the average threshold voltage shift of ±1 volts under positive and negative gate bias direct current (DC) stress for 10,000 seconds. Further, the semiconductor device of method 100 of FIG. 1 (e.g., semiconductor device 1350 (FIGS. 13-22, 24-26, 29, & 32)) can be manufactured at temperatures at or below approximately 200 degrees Celsius.

In implementation, the semiconductor device of method 100 of FIG. 1 (e.g., semiconductor device 1350 (FIGS. 13-22, 24-26, 29, & 32)) can be implemented as part of one or more electronic devices. Accordingly, the electronic device(s) can comprise the semiconductor device of method 100 of FIG. 1 (e.g., semiconductor device 1350 (FIGS. 13-22, 24-26, 29, & 32)). For example, the semiconductor device of method 100 of FIG. 1 (e.g., semiconductor device 1350 (FIGS. 13-22, 24-26, 29, & 32)) can comprise one or more transistors (e.g., thin film transistors) and as applicable, one or more emitters and/or detectors corresponding to the transistor(s). These transistor(s) and emitters and/or detectors can define pixels. In turn, the electronic device(s) can be configured to operate as a display and/or an imaging system, depending on whether the semiconductor device of method 100 of FIG. 1 (e.g., semiconductor device 1350 (FIGS. 13-22, 24-26, 29, & 32)) comprises emitters and/or detectors. In applicable examples, the display can comprise any of a liquid crystal display, an electrophoretic display, or an organic light emitting diode (OLED) display. Meanwhile, FIG. 33 illustrates an exemplary imaging system 3300 implementing the semiconductor device of method 100 of FIG. 1 (e.g., semiconductor device 1350 (FIGS. 13-22, 24-26, 29, & 32)), according to an embodiment.

Figure 33:
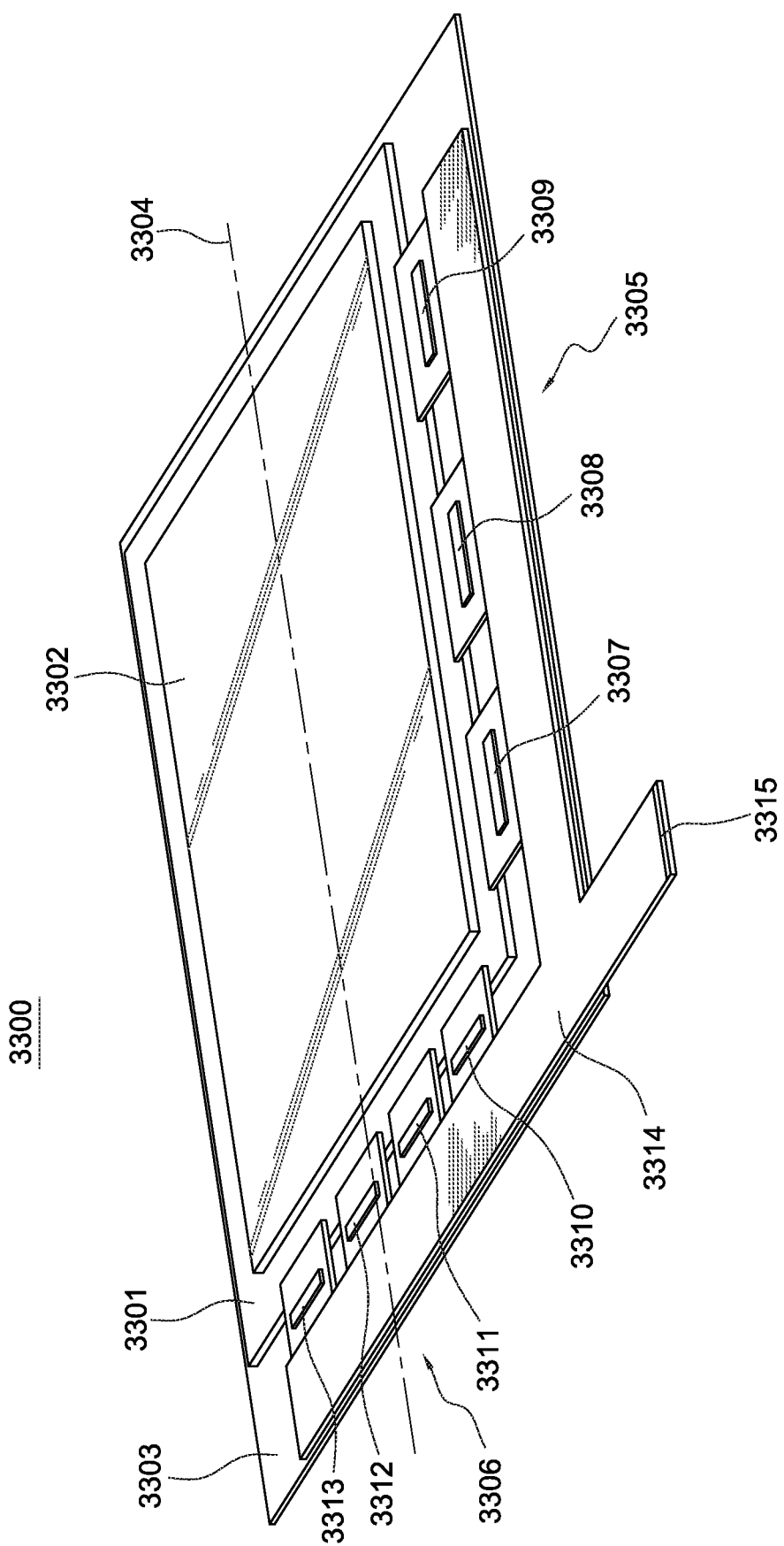
FIG. 33 illustrates an exemplary imaging system implementing the semiconductor device of FIGS. 1, 26, 29, & 32, according to an embodiment.

Referring to FIG. 33, imaging system 3300 is merely exemplary and is not limited to the embodiments presented herein. Imaging system 3300 can be employed in many different embodiments or examples not specifically depicted or described herein. In many examples, imaging system 3300 can comprise a digital x-ray imaging system.

Imaging system 3300 comprises active matrix pixel array 3301 and flexible scintillator layer 3302. Further, imaging system 3300 can comprise flexible base plate 3303. Meanwhile, imaging system 3300 can also comprise one or more gate driver chips 3305, one or more data line chips 3306, printed circuit board 3314, and output 3315.

For example, gate driver chip(s) 3305 can comprise gate driver chip 3307, gate driver chip 3308, and gate driver chip 3309. Further, data line chip(s) 3306 can comprise data line chip 3310, data line chip 3311, data line chip 3312, and data line chip 3313. However, although FIG. 33 illustrates gate driver chip(s) 3305 as comprising three gate driver chips and data line chip(s) 3306 as comprising four data line chips, imaging system 3300 can comprise any suitable quantity of gate driver chips and/or data line chips, such as, for example, as suitable to accommodate the quantity of pixels of active matrix pixel array 3301, as described below, and/or the corresponding gate driver line(s) and/or data line(s).

Flexible base plate 3303 can be under active matrix pixel array 3301, such as, for example, to reinforce and/or support active matrix pixel array 3301. Further, flexible scintillator layer 3302 can be over active matrix pixel array 3301. For example, flexible scintillator layer 3302 can be pressed tightly against active matrix pixel array 3301, such as, for example, at a side of active matrix pixel array 3301 opposite the flexible substrate.

For purposes of illustration, imaging system active matrix pixel array 3301 and/or flexible scintillator layer 3302 can comprise central axis 3304. Central axis 3304 can refer to an imaginary axis running parallel with and being equidistant to the opposing and longest sides of active matrix pixel array 3301. Where active matrix pixel array 3301 comprises multiple opposing and longest sides of equal length, such as, for example, when active matrix pixel array 3301 comprises a square array, any one set of opposing sides can be chosen by which to apply central axis 3304. In many embodiments, active matrix pixel array 3301, flexible scintillator layer 3302, and/or flexible base plate 3303 can be configured to be able to flex up to approximately 45 degrees with respect to central axis 3304. Thus, active matrix pixel array 3301, flexible scintillator layer 3302, and/or flexible base plate 3303 can comprise materials configured to permit this degree of deflection about central axis 3304.

Accordingly, the flexible substrate of active matrix pixel array 3301 can be similar or identical to flexible substrate 450 (FIG. 4). Meanwhile, in many examples, flexible scintillator layer 3302 can comprise gadolinium oxysulfide and/or cesium iodide. In other examples, flexible scintillator layer 3302 can comprise any suitable flexible material configured to luminesce when exposed to ionizing radiation. Further, flexible base plate 3303 can comprise plastic, aluminum, carbon fiber, and/or fiberglass.

Meanwhile, active matrix pixel array 3301 can be similar or identical to the semiconductor device of method 100 (FIG. 1) (e.g., semiconductor device 1350 (FIGS. 13-22, 24-26, 29, & 32)). Accordingly, active matrix pixel array 3301 can comprise multiple pixels configured and/or arranged in an active matrix array over a flexible substrate (e.g., flexible substrate 450 (FIG. 4)). In many examples, the multiple pixels can be configured and/or arranged in a regular grid. In other examples, the multiple pixels can be configured and/or arranged in another format (e.g., an irregular grid).

Each pixel of the multiple pixels can comprise a transistor (e.g., a thin film transistor) over the flexible substrate and a photodiode (e.g., a passive pixel PIN photodiode) over, on, and/or coupled to the transistor. In many examples, the transistor can comprise a passivation layer (e.g., passivation layer 1352 (FIGS. 26 & 32)), a gate metal layer over the passivation layer (e.g., gate metal layer 1353 (FIGS. 26 & 32)), a gate dielectric layer over the gate metal layer (e.g., gate dielectric layer 1554 (FIGS. 26 & 32)), a patterned active layer over the date dielectric layer (e.g., patterned active layer 1555 (FIGS. 26 & 32)), a patterned IMD layer over the patterned active layer (e.g., patterned IMD layer 1556 (FIGS. 26 & 32)), a mesa passivation layer over the patterned IMD layer (e.g., mesa passivation layer 1757 (FIGS. 26 & 32)), and one or more contact elements over the mesa passivation layer (e.g., N+ a-Si layer 2159 (FIGS. 26 & 32), diffusion barrier 2158 (FIGS. 26 & 32), and/or metal layer 2160 (FIGS. 26 & 32)). Meanwhile, the photodiode can comprise one or more semiconductor elements. For example, the semiconductor element(s) can comprise an N-type layer over the transistor (e.g., N-type layer 2564 (FIGS. 26 & 32)), an I layer over the N-type layer (e.g., I layer 2665 (FIGS. 26 & 32)), and a P-type layer over the I layer (e.g., P-type layer 2666 (FIGS. 26 & 32)). In some embodiments, the semiconductor elements can further comprise an ITO layer over the P-type layer (e.g., ITO layer 2667 (FIGS. 26 & 32)). Further still, the semiconductor elements can comprise a silicon nitride layer over the ITO layer (e.g., silicon nitride layer 2868 (FIGS. 26 & 32)).

A quantity of the multiple pixels can be a function of a resolution of active matrix pixel array 3301, and vice versa. Accordingly, the quantity of the multiple pixels can comprise any suitable number of pixels.

Figure 34:
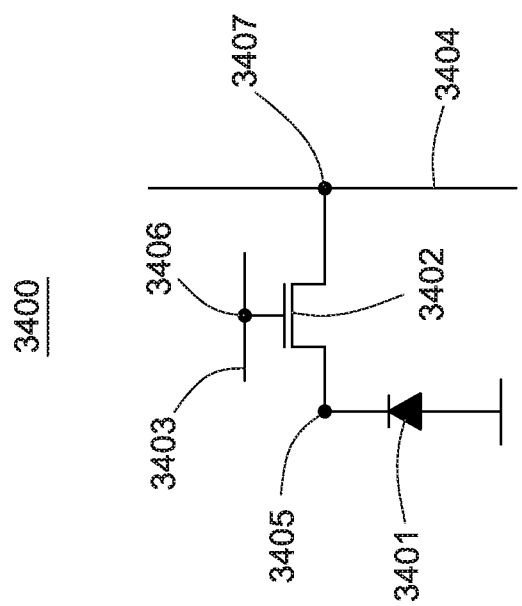
FIG. 34 illustrates an exemplary circuit diagram modeling a pixel, according to the embodiment of FIG. 33.

Meanwhile, each pixel of the multiple pixels can be coupled to one gate driver line of multiple gate driver lines and can be coupled one data line of multiple data lines. In many examples, each pixel for a given row of active matrix pixel array 3301 can be coupled to the same gate driver line of the multiple gate driver lines and different data lines of the multiple data lines. Conversely, each pixel for a given column of active matrix pixel array 3301 can be coupled to the same data line of the multiple data lines and different gate driver lines of the multiple gate driver liners. FIG. 34 illustrates an exemplary circuit diagram modeling pixel 3400, according to the embodiment of FIG. 33. Pixel 3400 can be similar or identical to any one of the multiple pixels of active matrix pixel array 3301 of imaging system 3300 (FIG. 33).

Referring to FIG. 34, pixel 3400 can comprise thin film transistor 3402, photodiode 3401, gate driver line 3403, and data line 3404. Each of thin film transistor 3402, photodiode 3401, gate driver line 3403, and data line 3404 can be similar or identical to the transistor, photodiode, gate driver line, and data line of any pixel of the multiple pixels as described above with respect to imaging system 3300 (FIG. 33). Photodiode 3401 can be coupled to thin film transistor 3402, such as, for example, at node 3405. Meanwhile, thin film transistor 3402 can be coupled to gate driver line 3403, such as, for example, at node 3406, and can be coupled to data line 3404, such as, for example, at node 3407.

Returning now to FIG. 33, the multiple gate driver lines can be tape automated bonded at their ends opposite of where the multiple gate driver lines are coupled with the multiple pixels to gate driver chip(s) 3305, and the multiple data lines can be taped automated bonded at their ends opposite where the multiple data lines are coupled with the multiple pixels to data line chip(s) 3306. Gate driver chip(s) 3305 and data line chip(s) 3306 can be configured as chips on flex. The multiple gate driver lines can be distributed evenly between gate driver chip(s) 3305, and the multiple data lines can be distributed evenly between data line chip(s) 3306, but the distribution need not be even if deemed suitable. Meanwhile, gate driver chip(s) 3305 and data line chip(s) 3306 can be tape automated bonded to printed circuit board 3314, which can be coupled to output 3315. Print circuit board 3314 can comprise any suitable flexible material or rigid material, as applicable. Output 3315 can comprise a zero insertion force connector.

Although not illustrated at FIG. 33, active matrix pixel array 3301, flexible scintillator layer 3302, flexible base plate 3303, gate driver chip(s) 3305, data line chip(s) 3306, printed circuit board 3314, and output 3315 can be encased in a housing. In some embodiments, imaging system 3300 can comprise the housing. The housing can be configured to block active matrix pixel array 3301 from substantially all light outside of the housing. Thus, the housing can be mostly or completely opaque. In many examples, the housing can also be flexible. In these examples, the housing can be configured to be at least as flexible as active matrix pixel array 3301, flexible scintillator layer 3302, and/or flexible base plate 3303.

Output connector 3315 can be coupled to one or more analog-to-digital converters, which can also be enclosed within the housing and/or mounted at another printed circuit board. Meanwhile, the analog-to-digital converter(s) can be coupled (e.g., via any suitable cable) to a frame grabber board external to the housing. The frame grabber board can comprise any suitable and/or conventional frame grabber board configured to receive data from an imaging system (e.g., a digital x-ray imaging system). The frame grabber board can be part of a computer system, and the computer system can be configured to display imaging data provided by active matrix pixel array 3301, such as, for example, at an electronic display. In some examples, imaging system 3300 can comprise the frame grabber board, the computer system, and/or the electronic display. In further examples, the computer system can comprise the frame grabber board and/or the electronic display.

In operation, imaging system 3300 can operate similarly to a conventional imaging system. That is, electromagnetic radiation can be emitted at an object between the emitter and active matrix pixel array 3301. When the electromagnetic radiation arrives at flexible scintillator layer 3302, flexible scintillator layer 3302 can luminesce to varying extents across its surface, providing photons to active matrix pixel array 3301. In turn, the multiple pixels of active matrix pixel array 3301 can detect the photons as the various rows and/or columns of pixels are activated by the corresponding gate driver lines. Meanwhile, the multiple pixels can then output the resulting imaging data to the data lines, on to the analog-to-digital converters until arriving at the frame grabber board. Accordingly, the imaging data can be provided to the computer system and/or to another remote computer system for analysis. In many examples, the computer system and/or the remote computer system can be similar or identical to computer system 4100 (FIG. 41), as described below.

Because active matrix pixel array 3301 comprises a flexible substrate, imaging system 3300 can be more durable and more lightweight than conventional imaging systems implementing rigid (e.g., glass) substrates. Further, imaging system 3300 can also be more portable than conventional imaging systems, permitting real-time interactive remote diagnostic imaging. Further still, imaging system 3300 can be sufficiently durable to preclude a need for post-fabrication ruggedization, thereby reducing a manufacturing cost and bulk volume of imaging system 3300 and further reducing the weight of imaging system 3300, factors which in turn can increase the portability of imaging system 3300.

Portable digital imaging functionality can be advantageous to permit digital imaging data to be transmitted to a location remote from imaging system 3300 for analysis and feedback (e.g., in real-time), such as, for example, by a physician (e.g., a radiologist), an engineer (e.g., a structural engineering), a government agency (e.g., police, military, etc.), or any other suitable expert in a field relating to an object being imaged by imaging system 3300. For example, imaging system 3300 could be implemented to remotely analyze injuries of civilians and/or military personnel, to remotely analyze damage to an oil pipeline and/or an aircraft body, and/or to remotely analyze hidden explosives and/or contraband. Further, when or after performing the analysis, the remote expert can enhance and/or augment digital images provided by imaging system 3300 by overlaying, fusing, and/or superimposing computer-based images, graphics, text, video, and/or audio instructions within the digital image files and/or auxiliary files corresponding thereto. Then, the digital image files and/or auxiliary files can be transmitted back to the location of imaging system 3300 for local display. In a more detailed example, imaging system 3300 could be used by a combat medic to image an injured soldier and send the imaging data to a remote (e.g., overseas) location where a distant physician could analyze the imaging data and relay back detailed medical diagnostic and treatment information to the combat medic.

Meanwhile, because active matrix pixel array 3301 can be similar or identical to the semiconductor device of method 100 of FIG. 1 (e.g., semiconductor device 1350 (FIGS. 13-22, 24-26, 29, & 32)), imaging system 3300 also can benefit from the electrical properties of the semiconductor device of method 100 of FIG. 1 (e.g., semiconductor device 1350 (FIGS. 13-22, 24-26, 29, & 32)). For example, the thin film transistors of active matrix pixel array 3301 can comprise a threshold voltage shift of greater than or equal to −1 volt and less than or equal to 1 volt for a ±20 volt direct current bias stress applied for 10,000 seconds, and/or the photodiode can comprise a leakage current of less than or equal to approximately 10 picoAmps/mm$^2$. Advantageously, this approximately constant operational threshold voltage and/or sub-10 picoAmps/mm$^2$ leakage current can permit active matrix pixel array 3301 to operate reliably enough and/or with sufficient image quality to obtain approval for use in medical imaging by the United States Food and Drug Administration.

Existing flexible imaging systems cannot achieve this degree of constancy of the operational threshold voltage. As a result, existing flexible imaging systems are not suitable for medical imaging and can experience threshold voltage shifts approaching or even exceeding 20 volts for a ±20 volt direct current bias stress applied for 10,000 seconds. Such voltage shifts in existing flexible imaging systems prevent thin film transistors in existing flexible imaging systems from even turning on when applying a gate pulse, thereby making the existing imaging systems non-functional. Meanwhile, existing flexible imaging systems also cannot maintain a sub-10 picoAmps/mm$^2$ leakage current provided by the photodiodes of active matrix pixel array 3301 and/or imaging system 3300.

Furthermore, because imaging system 3300 can be inherently more durable than a conventional imaging system as a result of the flexible substrate, in some examples, imaging system 3300 can survive being dropped and/or can survive impacts without being damaged. Further, because imaging system 3300 can be flexible and/or can comprise a thin form factor, in some examples, there can be locations accessible to imaging system 3300 that are not accessible to a conventional imaging system. For example, in some embodiments, imaging system 3300 can be slid underneath a car accident victim directly at the site of the accident such that movement of the victim prior to assessing the severity of the victim's injuries can be minimized. Further still, because imaging system 3300 can be flexible imaging system 3300 can conform to a surface of an object for imaging.

Figure 35:
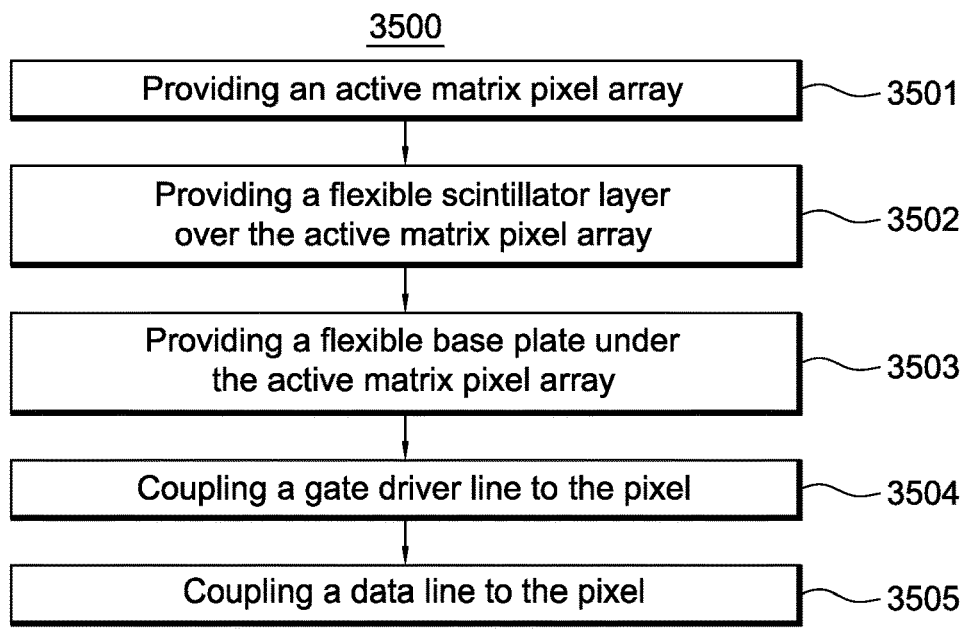
FIG. 35 illustrates a flow chart for an embodiment of a method of manufacturing an imaging system.

FIG. 35 illustrates a flow chart for an embodiment of method 3500 of manufacturing an imaging system. Method 3500 is merely exemplary and is not limited to the embodiments presented herein. Method 3500 can be employed in many different embodiments or examples not specifically depicted or described herein. In some embodiments, the activities of method 3500 can be performed in the order presented. In other embodiments, the activities of method 3500 can be performed in any other suitable order. In still other embodiments, one or more of the activities in method 3500 can be combined or skipped. The imaging system can be similar or identical to imaging system 3300 (FIG. 33).

Figure 36:
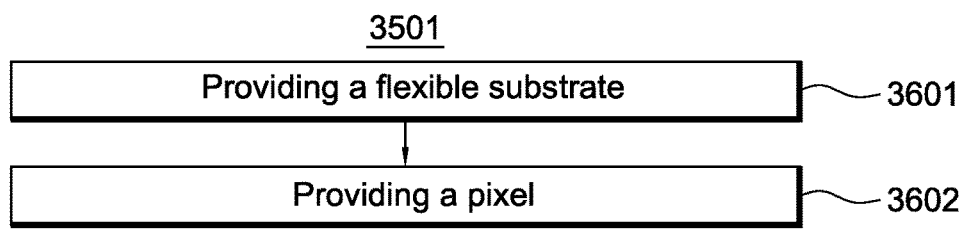
FIG. 36 illustrates an exemplary activity of providing an active matrix pixel array, according to the embodiment of FIG. 35.

Method 3500 can comprise activity 3501 of providing an active matrix pixel array. The active matrix pixel array can be similar or identical to active matrix pixel array 3301 (FIG. 33). FIG. 36 illustrates an exemplary activity 3501, according to the embodiment of FIG. 35.

Activity 3501 can comprise activity 3601 of providing a flexible substrate. The flexible substrate can be similar or identical to flexible substrate 450 (FIG. 4).

Figure 37:
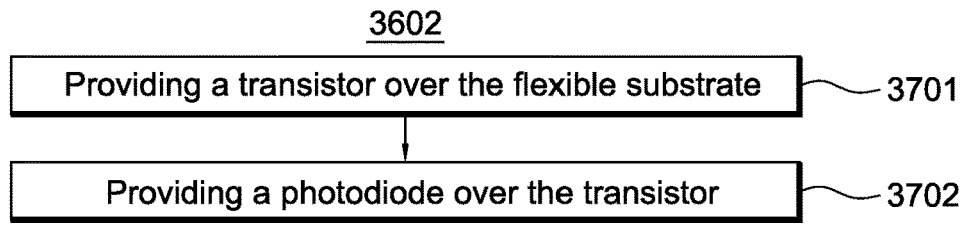
FIG. 37 illustrates an exemplary activity of providing a pixel, according to the embodiment of FIG. 35.

Activity 3501 can comprise activity 3602 of providing a pixel. The pixel can be similar or identical to any pixel of the multiple pixels of active matrix pixel array 3301 (FIG. 33). FIG. 37 illustrates an exemplary activity 3602, according to the embodiment of FIG. 35.

Figure 38:
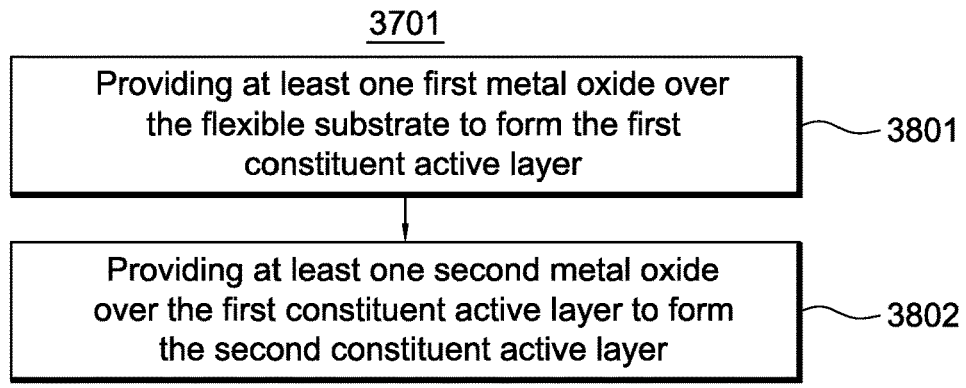
FIG. 38 illustrates an exemplary activity of providing a transistor over the flexible substrate, according to the embodiment of FIG. 35.

Activity 3602 can comprise activity 3701 of providing a transistor over the flexible substrate. The transistor can be similar or identical to any transistor of any pixel of the multiple pixels of active matrix pixel array 3301 (FIG. 33). FIG. 38 illustrates an exemplary activity 3701, according to the embodiment of FIG. 35.

Activity 3701 can comprise activity 3801 of providing at least one first metal oxide over the flexible substrate to form the first constituent active layer. The first constituent active layer can be similar or identical to first constituent active layer 3156 (FIG. 31).

Activity 3701 can comprise activity 3802 of providing at least one second metal oxide over the first constituent active layer to form the second constituent active layer. The second constituent active layer can be similar or identical to second constituent active layer 3157 (FIG. 31). In many examples, activity 3802 can be performed after activity 3801.

Figure 39:
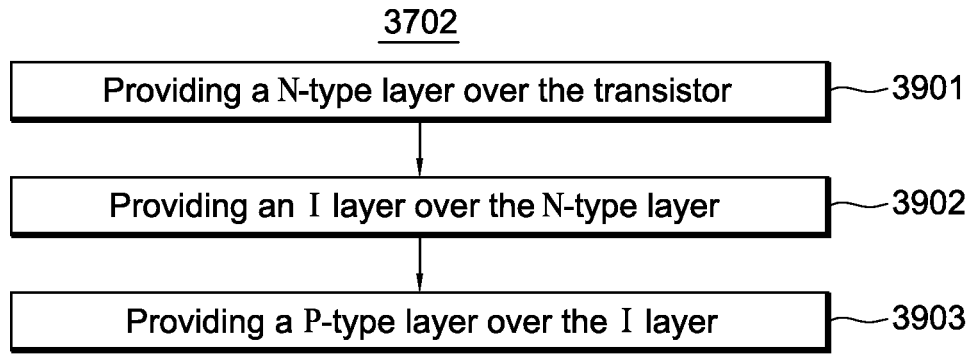
FIG. 39 illustrates an exemplary activity of providing a photodiode over the transistor, according to the embodiment of FIG. 35.

Returning now back to FIG. 37, activity 3602 can comprise activity 3702 of providing a photodiode over the transistor. The photodiode can be similar or identical to any photodiode of any pixel of the multiple pixels of active matrix pixel array 3301 (FIG. 33). In many examples, activity 3702 can be performed after activity 3701. FIG. 39 illustrates an exemplary activity 3702, according to the embodiment of FIG. 35.

Activity 3702 can comprise activity 3901 of providing an N-type layer over the transistor. In many examples, activity 3901 can comprise providing at least one of aluminum, silicon, neodymium, tantalum, molybdenum, chromium, titanium, and/or tungsten over the transistor. The N-type layer can be similar or identical to N-type layer 2564 (FIG. 25).

Activity 3702 can comprise activity 3902 of providing an I layer over the N-type layer. In many examples, activity 3902 can comprise providing intrinsically doped silicon over the N-type layer. In many examples, activity 3902 can be performed after activity 3901. The I layer can be similar or identical to I layer 2665 (FIG. 26).

Activity 3702 can comprise activity 3903 of providing a P-type layer over the I layer. Activity 3903 can comprise providing boron doped silicon over the I layer. In many examples, activity 3902 can be performed after activity 3902. The P layer can be similar or identical to P-type layer 2666 (FIG. 26).

Returning now to FIG. 35, method 3500 can comprise activity 3502 of providing a flexible scintillator layer over the active matrix pixel array. The flexible scintillator layer can be similar or identical to flexible scintillator layer 3302 (FIG. 33).

Further, method 3500 can comprise activity 3503 of providing a flexible base plate under the active matrix pixel array. The flexible base plate can be similar or identical to flexible base plate 3303 (FIG. 33). In some embodiments, activity 3503 can be performed prior to, after, and/or simultaneously with activity 3502.

Method 3500 can comprise activity 3504 of coupling a gate driver line to the pixel. In many examples, activity 3504 can be performed simultaneously with and/or as part of activity 3501.

Method 3500 can comprise activity 3505 of coupling a data line to the pixel. In many examples, activity 3505 can be performed simultaneously with and/or as part of activity 3501. Further, activity 3504 and activity 3505 can be performed approximately simultaneously with each other.

Figure 40:
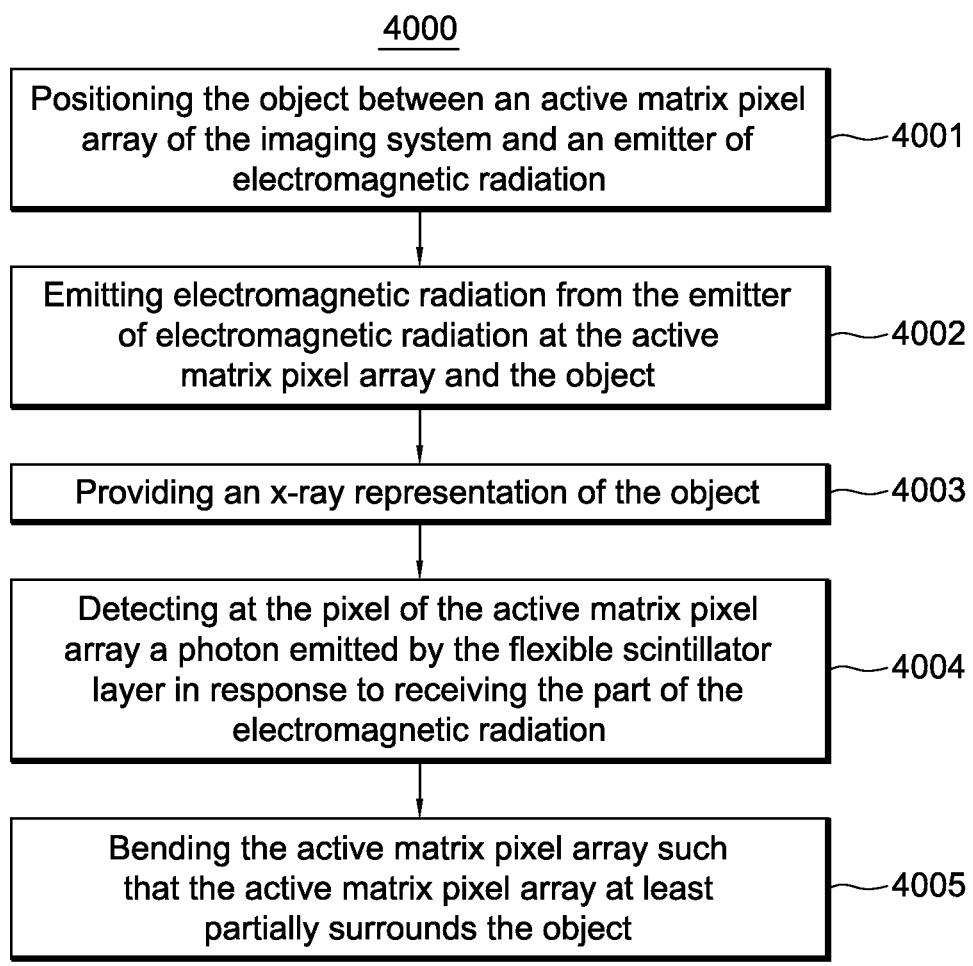
FIG. 40 illustrates a flow chart for an embodiment of a method of imaging an object with an imaging system.
Figure 41:
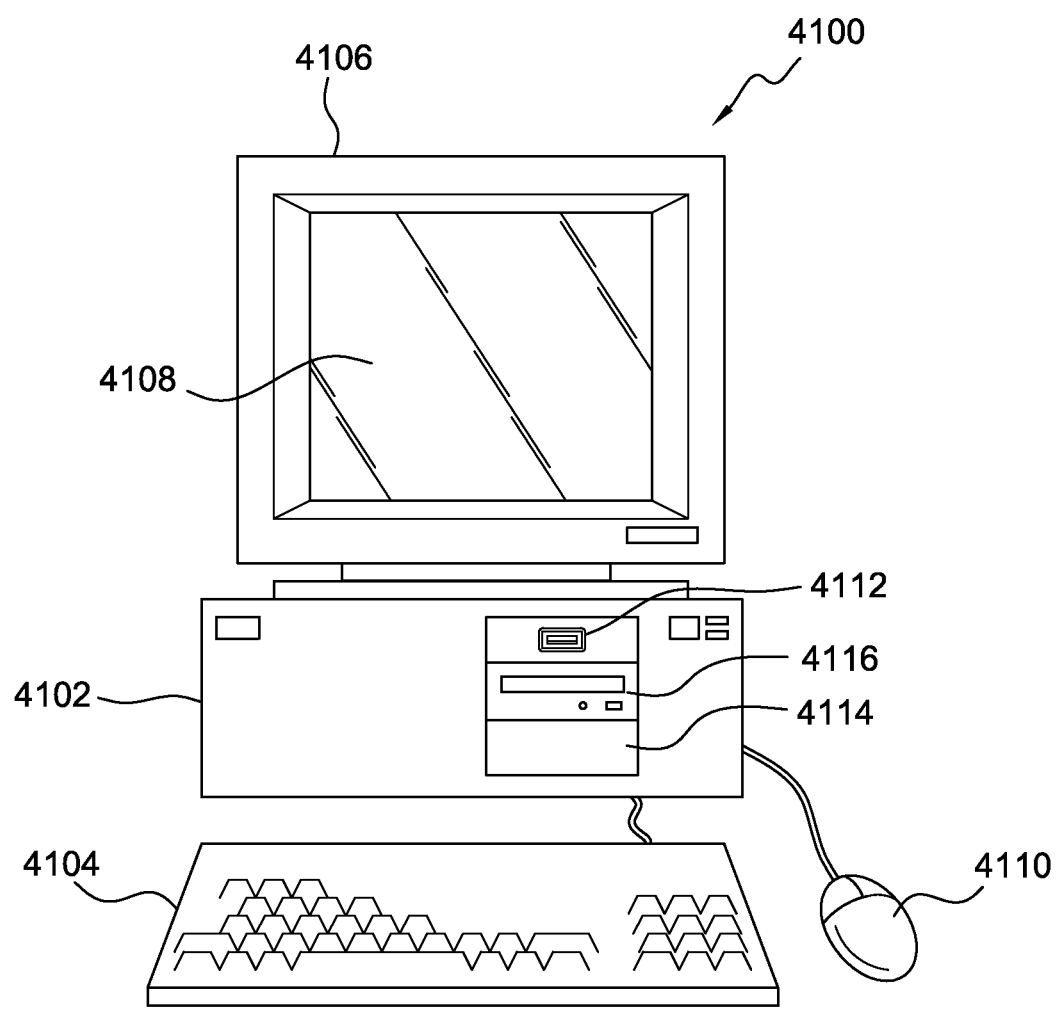
FIG. 41 illustrates a computer system that is suitable for implementing part of the functionality of the imaging system of FIG. 33 and/or the methods of FIGS. 35 and/or 40.

FIG. 40 illustrates a flow chart for an embodiment of method 4000 of imaging an object with an imaging system. Method 4000 is merely exemplary and is not limited to the embodiments presented herein. Method 4000 can be employed in many different embodiments or examples not specifically depicted or described herein. In some embodiments, the activities of method 4000 can be performed in the order presented. In other embodiments, the activities of method 4000 can be performed in any other suitable order. In still other embodiments, one or more of the activities in method 4000 can be combined or skipped. The imaging system can be similar or identical to imaging system 3300 (FIG. 33). The object can be any suitable object. In some examples, at least part of method 4000 can be implemented via execution of computer instructions configured to run at one or more processors and configured to be stored at one or more memory storage devices of a computer system. The computer system can be similar or identical to computer system 4100 (FIG. 41).

Method 4000 can comprise activity 4001 of positioning the object between an active matrix pixel array of the imaging system and an emitter of electromagnetic radiation. The active matrix pixel array can be similar or identical to active matrix pixel array 3301 (FIG. 33). The emitter can comprise any suitable emitter of electromagnetic radiation for an imaging system, such as, for example, a digital x-ray imaging system.

Method 4000 can comprise activity 4002 of emitting electromagnetic radiation from the emitter of electromagnetic radiation at the active matrix pixel array and the object. In some examples, activity 4002 can comprise receiving part of the electromagnetic radiation at a flexible scintillator layer positioned between the active matrix pixel array and the object. The flexible scintillator layer can be similar or identical to flexible scintillator layer 3302 (FIG. 33).

Method 4000 can comprise activity 4003 of providing an x-ray representation of the object. In some examples, activity 4003 can comprise generating the x-ray representation of the object based on a photon detected at a pixel of the active matrix pixel array. The pixel can be similar or identical to any pixel of the multiple pixels of active matrix pixel array 3301 (FIG. 33).

Method 4000 can comprise activity 4004 of detecting at the pixel of the active matrix pixel array a photon emitted by the flexible scintillator layer in response to receiving the part of the electromagnetic radiation.

Method 4000 can comprise activity 4005 of bending the active matrix pixel array such that the active matrix pixel array at least partially surrounds the object.

Turning to the drawings, FIG. 41 illustrates an exemplary embodiment of a computer system 4100, all of which or a portion of which can be suitable for (i) implementing part or all of one or more embodiments of the techniques, methods, and/or systems described herein, and/or (ii) implementing and/or operating part or all of one or more embodiments of the memory storage device(s) described herein. For example, in some embodiments, all or a portion of computer system 4100 can be suitable for implementing part of the functionality of imaging system 3300 (FIG. 33) as well as method 4000 (FIG. 40) and/or any of the various activities of method 4000 (FIG. 40).

In many embodiments, computer system 4100 can comprise a chassis 4102, a keyboard 4104, a computer monitor 4106, and/or a mouse 4110. Further, chassis 4102 can contain one or more circuit boards (not shown), and/or computer monitor 4106 can comprise a screen 4108. In some embodiments, chassis 4102 can contain a Universal Serial Bus (USB) port 4112, a hard drive 4114, and/or an optical disc drive 4116. Meanwhile, for example, optical disc drive 4116 can comprise a Compact Disc Read-Only Memory (CD-ROM) drive, a Digital Video Disc (DVD) drive, or a Blu-ray drive. Still, in other embodiments, a different or separate one of chassis 4102 (and its internal components) can be suitable for implementing part or all of one or more embodiments of the techniques, methods, and/or systems described herein. Further, one or more elements of computer system 4100 (e.g., keyboard 4104, computer monitor 4106, and/or mouse 4110, etc.) can also be appropriate for implementing part or all of one or more embodiments of the techniques, methods, and/or systems described herein.

Figure 42:
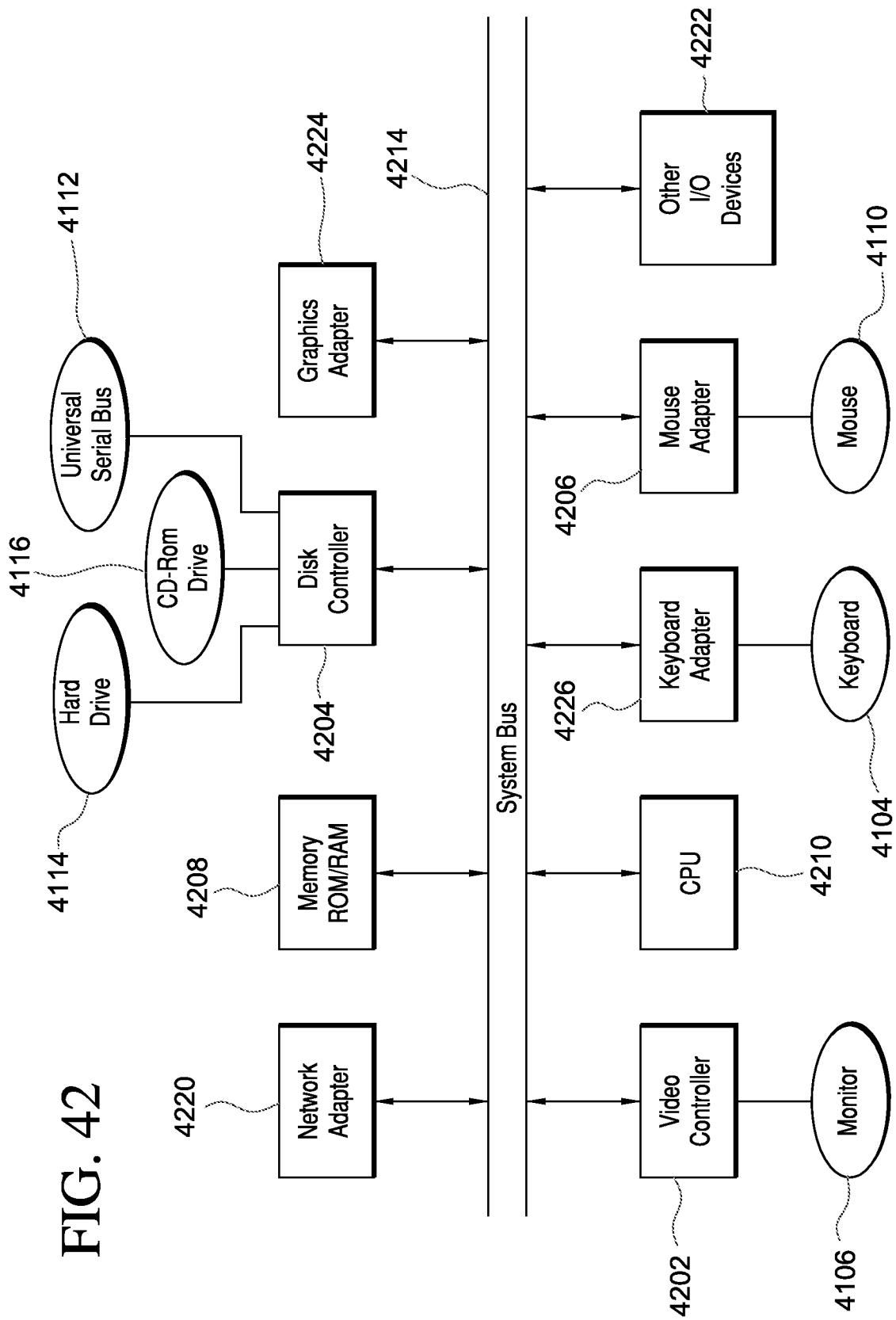
FIG. 42 illustrates a representative block diagram of an example of the elements included in the circuit boards inside chassis of the computer system of FIG. 41.

Turning ahead in the drawings, FIG. 42 illustrates a representative block diagram of exemplary elements included on the circuit boards inside chassis 4102 (FIG. 41). For example, a central processing unit (CPU) 4210 can be coupled to a system bus 4214. In various embodiments, the architecture of CPU 4210 can be compliant with any of a variety of commercially distributed architecture families.

Meanwhile, system bus 4214 can be coupled to a memory storage unit 4208. Memory storage unit 4208 can comprise (i) non-volatile memory, such as, for example, read only memory (ROM) and/or (ii) volatile memory, such as, for example, random access memory (RAM). The non-volatile memory can comprise removable and/or non-removable non-volatile memory. In some embodiments, RAM can include dynamic RAM (DRAM), static RAM (SRAM), etc. Further, ROM can include mask-programmed ROM, programmable ROM (PROM), one-time programmable ROM (OTP), erasable programmable read-only memory (EPROM), electrically erasable programmable ROM (EEPROM) (e.g., electrically alterable ROM (EAROM) and/or flash memory), etc. In these or other embodiments, memory storage unit 4208 can comprise (i) non-transitory memory and/or (ii) transitory memory.

The memory storage devices(s) of the various embodiments disclosed herein can comprise memory storage unit 4208, an external memory storage drives (not shown), such as, for example, a USB-equipped electronic memory storage drive coupled to USB port 4112 (FIGS. 41 & 42), hard drive 4114 (FIGS. 41 & 42), optical disc drive 4116, a floppy disk drive (not shown), etc. As used herein, the terms non-volatile or non-transitory memory storage devices(s) refer to the portions of the memory storage device(s) that are non-volatile or non-transitory memory.

In various examples, portions of the memory storage device(s) of the various embodiments disclosed herein (e.g., portions of the non-volatile memory storage devices(s)) can be encoded with a boot code sequence suitable for restoring computer system 4100 (FIG. 41) to a functional state after a system reset. In addition, portions of the memory storage device(s) of the various embodiments disclosed herein (e.g., portions of the non-volatile memory storage device(s)) can comprise microcode such as a Basic Input-Output System (BIOS) or Unified Extensible Firmware Interface (UEFI) operable with computer system 4100 (FIG. 41). In the same or different examples, portions of the memory storage device(s) of the various embodiments disclosed herein (e.g., portions of the non-volatile memory storage device(s)) can comprise an operating system, which can be a software program that manages the hardware and software resources of a computer and/or a computer network. Meanwhile, the operating system can perform basic tasks such as, for example, controlling and allocating memory, prioritizing the processing of instructions, controlling input and output devices, facilitating networking, and managing files. Exemplary operating systems can comprise (i) Microsoft® Windows® operating system (OS) by Microsoft Corp. of Redmond, Wash., United States of America, (ii) Mac® OS by Apple Inc. of Cupertino, Calif., United States of America, (iii) UNIX® OS, and (iv) Linux® OS. Further exemplary operating systems can comprise (i) iOS™ by Apple Inc. of Cupertino, Calif., United States of America, (ii) the Blackberry® OS by Research In Motion (RIM) of Waterloo, Ontario, Canada, (iii) the Android™ OS developed by the Open Handset Alliance, or (iv) the Windows Mobile™ OS by Microsoft Corp. of Redmond, Wash., United States of America. Further, as used herein, the term "computer network" can refer to a collection of computers and devices interconnected by communications channels that facilitate communications among users and allow users to share resources (e.g., an internet connection, an Ethernet connection, etc.). The computers and devices can be interconnected according to any conventional network topology (e.g., bus, star, tree, linear, ring, mesh, etc.).

As used herein, "processor" and/or "processing device" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the processor(s) of the various embodiments disclosed herein can comprise CPU 4210.

In the depicted embodiment of FIG. 42, various I/O devices such as a disk controller 4204, a graphics adapter 4224, a video controller 4202, a keyboard adapter 4226, a mouse adapter 4206, a network adapter 4220, and other I/O devices 4222 can be coupled to system bus 4214. Keyboard adapter 4226 and mouse adapter 4206 can be coupled to keyboard 4104 (FIGS. 41 & 42) and mouse 4110 (FIGS. 41 & 42), respectively, of computer system 4100 (FIG. 41). While graphics adapter 4224 and video controller 4202 are illustrated as distinct units in FIG. 42, in other embodiments, video controller 4202 can be integrated into graphics adapter 4224, or vice versa. Video controller 4202 is suitable to operate computer monitor 4106 (FIGS. 41 & 42) to display images on screen 4108 (FIG. 41) of computer system 4100 (FIG. 41). Disk controller 4204 can control hard drive 4114 (FIGS. 41 & 42), USB port 4112 (FIGS. 41 & 42), and optical disc drive 4116 (FIGS. 41 & 42). In other embodiments, distinct units can be used to control each of these devices separately.

Network adapter 4220 can be suitable to connect computer system 4100 (FIG. 41) to a computer network by wired communication (e.g., a wired network adapter) and/or wireless communication (e.g., a wireless network adapter). In some embodiments, network adapter 4220 can be plugged or coupled to an expansion port (not shown) in computer system 4100 (FIG. 41). In other embodiments, network adapter 4220 can be built into computer system 4100 (FIG. 41). For example, network adapter 4220 can be built into computer system 4100 (FIG. 41) by being integrated into the motherboard chipset (not shown), or implemented via one or more dedicated communication chips (not shown), connected through a PCI (peripheral component interconnector) or a PCI express bus of computer system 4100 (FIG. 41) or USB port 4112 (FIG. 41).

Returning now to FIG. 41, although many other components of computer system 4100 are not shown, such components and their interconnection are well known to those of ordinary skill in the art. Accordingly, further details concerning the construction and composition of computer system 4100 and the circuit boards inside chassis 4102 are not discussed herein.

Meanwhile, when computer system 4100 is running, program instructions (e.g., computer instructions) stored on one or more of the memory storage device(s) of the various embodiments disclosed herein can be executed by CPU 4210 (FIG. 42). At least a portion of the program instructions, stored on these devices, can be suitable for carrying out at least part of the techniques and methods described herein. In various embodiments, computer 4100 can be reprogrammed with one or more modules, applications, and/or databases to convert computer system 4100 from a general purpose computer to a special purpose computer. For purposes of illustration, programs and other executable program components are shown herein as discrete systems, although it is understood that such programs and program components may reside at various times in memory storage device(s) of computing device 4100, and can be executed by CPU 4210 (FIG. 42). Alternatively, or in addition to, the techniques, methods, and/or systems described herein described herein can be implemented in hardware, or a combination of hardware, software, and/or firmware. For example, one or more application specific integrated circuits (ASICs) can be programmed to carry out one or more of the techniques, methods, and/or systems described herein. For example, one or more of the programs and/or executable program components described herein can be implemented in one or more ASICs.

Further, although computer system 4100 is illustrated as a desktop computer in FIG. 41, in many examples, computer system 4100 can have a different form factor while still having functional elements similar to those described for computer system 4100. In some embodiments, computer system 4100 may comprise a single computer, a single server, or a cluster or collection of computers or servers, or a cloud of computers or servers. Typically, a cluster or collection of servers can be used when the demand on computer system 4100 exceeds the reasonable capability of a single server or computer. In certain embodiments, computer system 4100 may comprise a portable computer, such as a laptop computer. In certain other embodiments, computer system 4100 may comprise a mobile device, such as a smart phone. In certain additional embodiments, computer system 4100 may comprise an embedded system.

Figure 43:
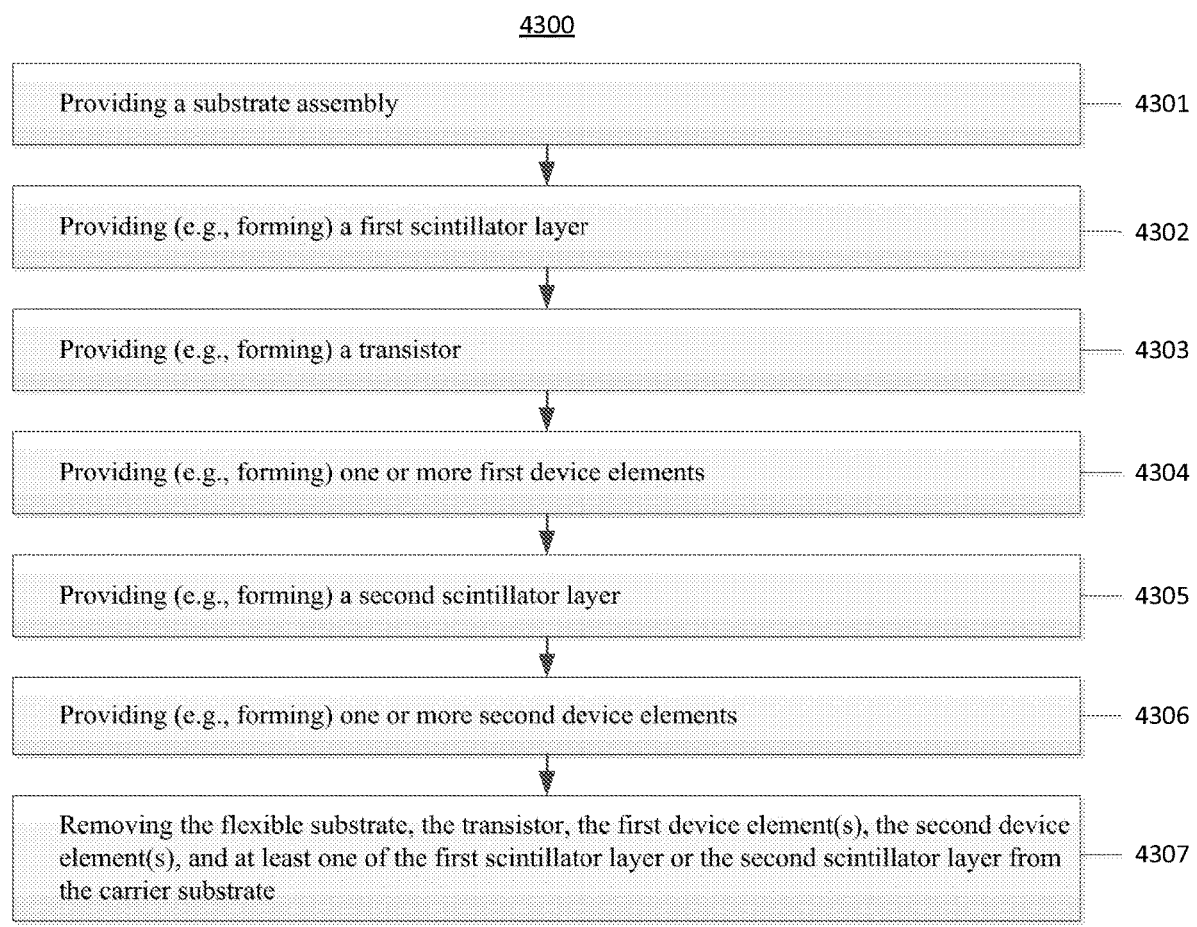
FIG. 43 illustrates a flow chart for a method, according to an embodiment.

Turning ahead again in the drawings, FIG. 43 illustrates a flow chart for a method 4300, according to an embodiment. Method 4300 is merely exemplary and is not limited to the embodiments presented herein. Method 4300 can be employed in many different embodiments or examples not specifically depicted or described herein. In some embodiments, the activities of method 4300 can be performed in the order presented. In other embodiments, the activities of method 4300 can be performed in any suitable order. In still other embodiments, one or more of the activities of method 4300 can be combined or skipped.

In many embodiments, method 4300 can be similar to method 100 (FIG. 1). In these or other embodiments, method 4300 can comprise a method of manufacturing an electronic device having one or more processed and/or integrated scintillator layers (e.g., a first scintillator layer and/or a second scintillator layer), which can present various advantages that are discussed in greater detail below.

In various embodiments, the electronic device can be similar or identical to electronic device 5000 (FIG. 50), as described below. Further, the electronic device can be similar or identical to one of the electronic device(s) comprising the semiconductor device of method 100 of FIG. 1 (e.g., semiconductor device 1350 of FIGS. 13-22, 24-26, 29, & 32) as described above with respect to method 100 (FIG. 1). Accordingly, the electronic device can comprise a semiconductor device, and the semiconductor device can be similar or identical to semiconductor device 1350 (FIGS. 13-22, 24-26, 29, & 32).

Figure 44:
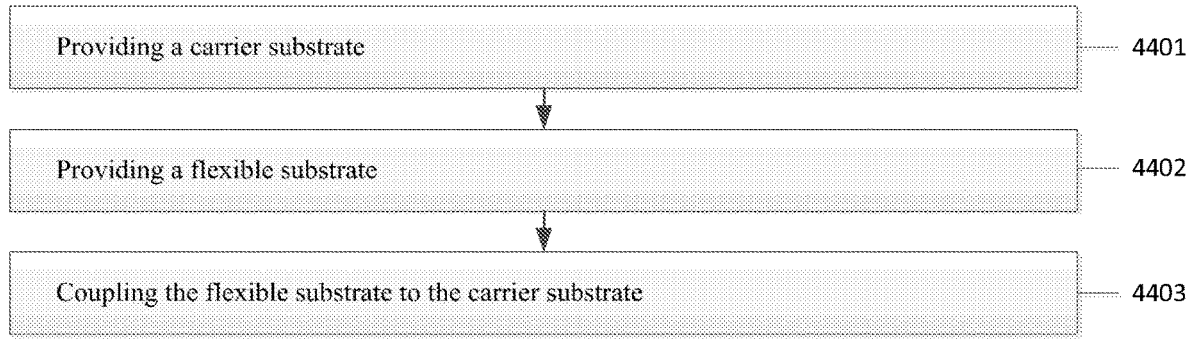
FIG. 44 illustrates an exemplary activity of providing a substrate assembly, according to the embodiment of FIG. 43.

In many embodiments, method 4300 can comprise activity 4301 of providing a substrate assembly. In these or other embodiments, activity 4301 can be similar or identical to activity 110 (FIG. 1). Further, the substrate assembly can be similar or identical to substrate assembly 540 (FIGS. 5, 6, 8-10, 13-22, 24-26, & 32). FIG. 44 illustrates an exemplary activity 4301, according to the embodiment of FIG. 43.

In some embodiments, activity 4301 can comprise activity 4401 of providing a carrier substrate. In these or other embodiments, activity 4401 can be similar or identical to activity 213 (FIG. 2). Further, the carrier substrate can be similar or identical to carrier substrate 651 (FIGS. 6 & 8-10).

In some embodiments, activity 4301 can comprise activity 4402 of providing a flexible substrate. In these or other embodiments, activity 4402 can be similar or identical to activity 211 (FIG. 2). Further, the flexible substrate can be similar or identical to flexible substrate 450 (FIGS. 5, 6, & 8-10). In some embodiments, activity 4402 can be omitted.

In various embodiments, the substrate assembly and/or the flexible substrate can be transparent to radiation (e.g., x-ray radiation), such as, for example, when method 4300 comprises activity 4302, as described below. Implementing the substrate assembly and/or the flexible substrate to be transparent to radiation (e.g., x-ray radiation) can permit the first scintillator layer of activity 4302 to receive radiation, permitting the first scintillator layer to emit photons that can be detected by one or more of the first device element(s) (e.g., a photodetector) of activity 4304, as described below.

In some embodiments, method 4301 can comprise activity 4403 of coupling the flexible substrate to the carrier substrate. In these or other embodiments, performing activity 4403 can be similar or identical to coupling the flexible substrate to the carrier substrate as described above with respect to method 100 (FIG. 1) and/or activity 110 (FIG. 1).

For example, activity 4403 can be similar or identical to activity 217 (FIG. 2). In some embodiments, activity 4403 can be omitted, such as, for example, when activity 4402 is omitted.

Figure 45:
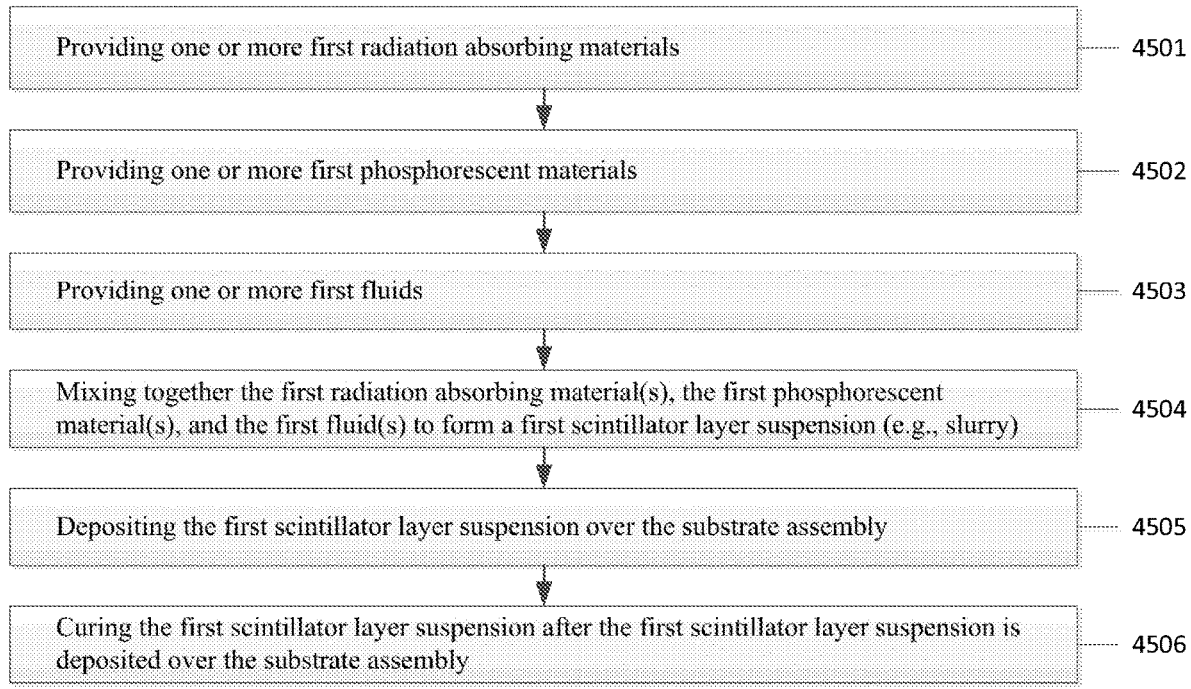
FIG. 45 illustrates an exemplary activity of providing (e.g., forming) a first scintillator layer, according to the embodiment of FIG. 43.

Referring again to FIG. 43, in many embodiments, method 4300 can comprise activity 4302 of providing (e.g., forming) a first scintillator layer. In some embodiments, the first scintillator layer can be similar to flexible scintillator layer 3302 (FIG. 33). In various embodiments, activity 4302 can comprise an activity of providing the first scintillator layer over (e.g., on) the substrate assembly. For example, in some embodiments, the first scintillator layer can directly contact the substrate assembly, the flexible substrate, or the carrier substrate. In other embodiments, activity 4302 can be omitted. FIG. 45 illustrates an exemplary activity 4302, according to the embodiment of FIG. 43.

In some embodiments, activity 4302 can comprise activity 4501 of providing one or more first radiation absorbing materials. The first radiation absorbing material(s) can be configured to absorb radiation (e.g., x-ray radiation).

Although, in some embodiments, the first radiation absorbing material(s) can comprise any material or materials configured to absorb radiation (e.g., x-ray radiation), in many embodiments, the first radiation absorbing material(s) can comprise one or more high atomic number materials. Exemplary first radiation absorbing material(s) can comprise cesium iodide, one or more cesium oxides, one or more dysprosium oxides, one or more gadolinium oxides, one or more lanthanum oxides, one or more yttrium oxides, one or more cesium oxysulfides, one or more dysprosium oxysulfides, one or more gadolinium oxysulfides, one or more lanthanum oxysulfides, one or more yttrium oxysulfides, one or more cesium orthosilicates, one or more dysprosium orthosilicates, one or more gadolinium orthosilicates, one or more lanthanum orthosilicates, and/or one or more yttrium orthosilicates.

In some embodiments, activity 4302 can comprise activity 4502 of providing one or more first phosphorescent materials. The first phosphorescent material(s) can be configured to luminesce.

Although, in some embodiments, the first phosphorescent material(s) can comprise any material or materials configured to luminesce, in many embodiments, the first phosphorescent material(s) can comprise one or more rare earth elements. Exemplary first phosphorescent material(s) can comprise cerium, europium, fluorine, praseodymium, sodium, terbium, and/or titanium. In some embodiments, the first phosphorescent material(s) can be selected based on the first device material(s) (e.g., the photodetector) implemented in activity 4304 (FIG. 4). That is, the first phosphorescent material(s) can be selected to tune the light output of the first phosphorescent material(s) to the first device material(s) (e.g., the photodetector) implemented in activity 4304 (FIG. 4).

In some embodiments, the first phosphorescent material(s) can be provided in a powder form. In these or other embodiments, the first phosphorescent material(s) can comprise an average particle diameter. The average particle diameter can be less than or equal to approximately 12 microns.

In many embodiments, activity 4302 can comprise activity 4503 of providing one or more first fluids. The first fluid(s) can comprise deionized water, isopropyl alcohol, one or more surfactants, and one or more binding agents. The surfactant(s) and/or the binding agent(s) implemented can depend on the first radiation absorbing material(s) implemented in activity 4501 and/or the first phosphorescent material(s) implemented in activity 4502. In some embodiments, the binding agent(s) can comprise one or more liquid polymers (e.g., liquid polyimide).

In many embodiments, activity 4302 can comprise activity 4504 of mixing together the first radiation absorbing material(s), the first phosphorescent material(s), and the first fluid(s) to form a first scintillator layer suspension (e.g., slurry). Activity 4504 can be performed after activities 4501-4503.

In many embodiments, activity 4302 can comprise activity 4505 of depositing the first scintillator layer suspension over the substrate assembly. In some embodiments, the first scintillator layer suspension can be deposited over the substrate assembly using any suitable fluid coating technique or techniques (e.g., spray coating, spin coating, slot die coating, curtain coating, ink jet printing, screen printing). Activity 4505 can be performed after activity 4504.

In many embodiments, activity 4302 can comprise activity 4506 of curing the first scintillator layer suspension after the first scintillator layer suspension is deposited over the substrate assembly. For example, in some embodiments, activity 4302 can comprise an activity of baking (e.g., dehydrating) the first scintillator layer suspension after the first scintillator layer suspension is deposited over the substrate assembly. The first scintillator layer suspension can be baked at greater than or equal to approximately 50 degrees Celsius and less than or equal to approximately 400 degrees Celsius. Activity 4506 can be performed after activity 4505.

Figure 46:
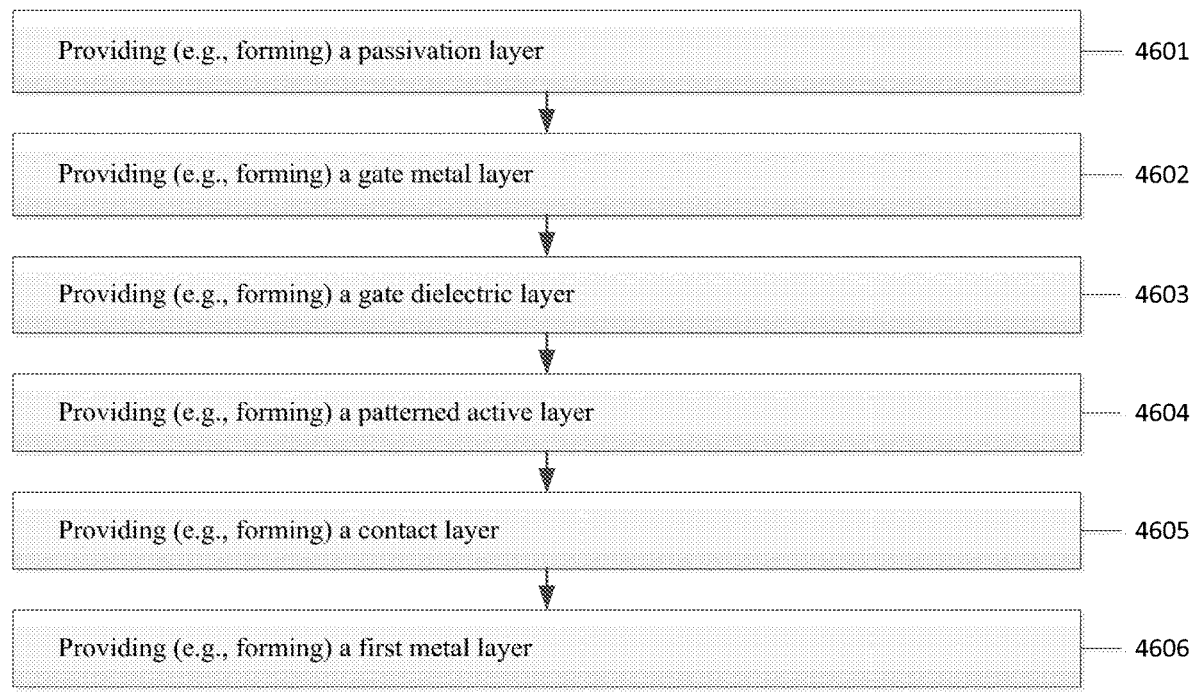
FIG. 46 illustrates an exemplary activity of providing (e.g., forming) a transistor, according to the embodiment of FIG. 43.

Referring again to FIG. 43, in many embodiments, method 4300 can comprise activity 4303 of providing (e.g., forming) a transistor. In some embodiments, activity 4303 can be similar or identical to activity 3701 (FIG. 37). Further, the transistor can be similar or identical to thin film transistor 3402 (FIG. 34). In various embodiments, activity 4303 can comprise an activity of providing the transistor over (e.g., on) the first scintillator layer, such as, for example, when method 4300 comprises activity 4302. For example, in some embodiments, the transistor can directly contact the first scintillator layer. FIG. 46 illustrates an exemplary activity 4303, according to the embodiment of FIG. 43.

For example, in some embodiments, activity 4303 can comprise activity 4601 of providing (e.g., forming) a passivation layer (e.g., over the substrate assembly). In these or other embodiments, performing activity 4601 can be similar or identical to providing the passivation layer as described above with respect to method 100 (FIG. 1). Further, the passivation layer can be similar or identical to passivation layer 1352 (FIGS. 13-22, 24-26, & 32). In some embodiments, activity 4601 can comprise an activity of providing the passivation layer over (e.g., on) the first scintillator layer, such as, for example, when method 4300 (FIG. 43) comprises activity 4302. For example, in various embodiments, the passivation layer can directly contact the first scintillator layer. Accordingly, the first scintillator layer can be coupled to the passivation layer without an adhesive, thereby positioning the first scintillator layer closer to the first device element(s) of activity 4304 (FIG. 43), as described below.

In some embodiments, activity 4303 can comprise activity 4602 of providing (e.g., forming) a gate metal layer (e.g., over the passivation layer). In these or other embodiments, performing activity 4602 can be similar or identical to providing the gate metal layer as described above with respect to method 100 (FIG. 1). Further, the gate metal layer can be similar or identical to gate metal layer 1353 (FIGS. 13-22, 24-26, & 32).

In some embodiments, activity 4303 can comprise activity 4603 of providing (e.g., forming) a gate dielectric layer (e.g., over the gate metal layer). In these or other embodiments, performing activity 4603 can be similar or identical to providing the gate dielectric layer as described above with respect to method 100 (FIG. 1). Further, the gate dielectric layer can be similar or identical to gate dielectric layer 1554 (FIGS. 15-22, 24-26, & 32).

In some embodiments, activity 4303 can comprise activity 4604 of providing (e.g., forming) a patterned active layer (e.g., over the gate dielectric layer). In these or other embodiments, performing activity 4604 can be similar or identical to providing the patterned active layer as described above with respect to method 100 (FIG. 1). Further, the patterned active layer can be similar or identical to patterned active layer 1555 (FIGS. 15, 17, 19, 21, 24-26, & 32).

In some embodiments, activity 4303 can comprise activity 4605 of providing (e.g., forming) a contact layer. In many embodiments, the contact layer can comprise an n-type or p-type contact layer. In these or other embodiments, performing activity 4605 can be similar or identical to providing N+ a-Si layer 2159 (FIGS. 21, 22, 24-26, & 32) as described above with respect to method 100 (FIG. 1) and/or activity 1113 (FIG. 11). Further, in some embodiments, the contact layer can be similar or identical to N+ a-Si layer 2159 (FIGS. 21, 22, 24-26, & 32). In further embodiments, the contact layer can comprise a phosphorous doped amorphous silicon layer.

In some embodiments, activity 4303 can comprise activity 4606 of providing (e.g., forming) a first metal layer (e.g., over the patterned active layer). In these or other embodiments, performing activity 4606 can be similar or identical to providing the metal layer as described above with respect to method 100 (FIG. 1) and/or activity 1113 (FIG. 11). Further, the first metal layer can be similar or identical to metal layer 2160 (FIGS. 21, 22, 24-26, & 32).

Figure 47:
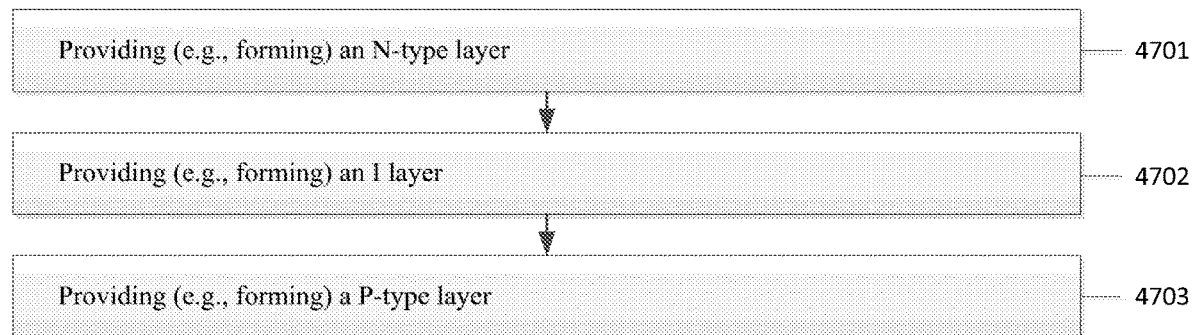
FIG. 47 illustrates an exemplary activity of providing (e.g., forming) one or more first device elements, according to the embodiment of FIG. 43.

In many embodiments, method 4300 can comprise activity 4304 of providing (e.g., forming) one or more first device elements. In these or other embodiments, activity 4304 can be similar or identical to part of activity 1121 (FIG. 11). Further, the first device element(s) can be similar or identical to one or more of the semiconductor element(s) described above with respect to activity 1121 (FIG. 11). For example, the first device element(s) can comprise a photodetector (e.g., a photodiode). FIG. 47 illustrates an exemplary activity 4304, according to the embodiment of FIG. 43.

For example, in some embodiments, activity 4304 can comprise activity 4701 of providing (e.g., forming) an N-type layer. In these or other embodiments, performing activity 4701 of providing the N-type layer can be similar or identical to providing the N-type layer as described above with respect to method 100 (FIG. 1) and/or activity 1121 (FIG. 11); and/or activity 4701 can be similar or identical to activity 3901 (FIG. 39). Further, the N-type layer can be similar or identical to N-type layer 2564 (FIGS. 25, 26, & 32).

In some embodiments, activity 4304 can comprise activity 4702 of providing (e.g., forming) an I layer. In these or other embodiments, performing activity 4201 of providing the I layer can be similar or identical to providing the I layer as described above with respect to method 100 (FIG. 1) and/or activity 1121 (FIG. 11); and/or activity 4702 can be similar or identical to activity 3902 (FIG. 39). Further, the I layer can be similar or identical to I layer 2565 (FIGS. 26 & 32).

In some embodiments, activity 4304 can comprise activity 4703 of providing (e.g., forming) a P-type layer. In these or other embodiments, performing activity 4703 of providing the P-type layer can be similar or identical to providing the P-type layer as described above with respect to method 100 (FIG. 1) and/or activity 1121 (FIG. 11); and/or activity 4703 can be similar or identical to activity 3903 (FIG. 39). Further, the P-type layer can be similar or identical to P-type layer 2566 (FIGS. 26 & 32).

In many embodiments, the N-type layer, the I layer, and the P-type layer can form the photodetector (e.g., photodiode). That is, the photodetector (e.g., photodiode) can comprise the N-type layer, the I layer, and the P-type layer.

Figure 48:
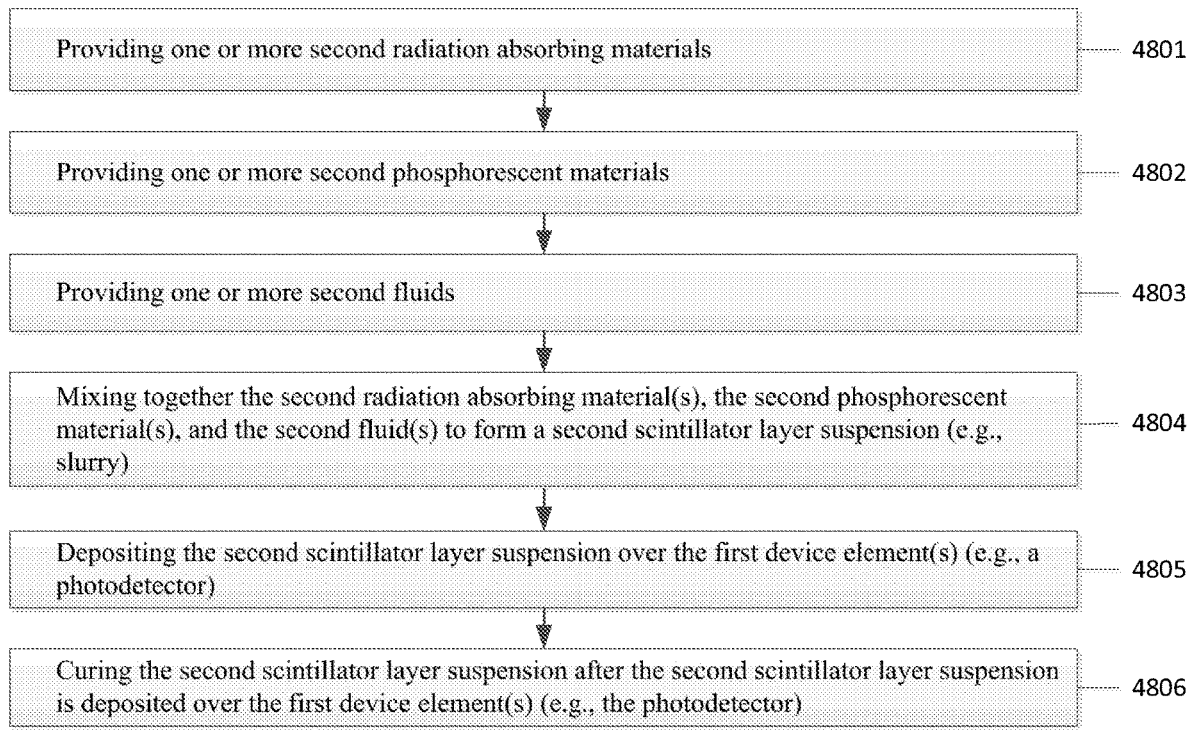
FIG. 48 illustrates an exemplary activity of providing (e.g., forming) a second scintillator layer, according to the embodiment of FIG. 43.

Referring again to FIG. 43, in many embodiments, method 4300 can comprise activity 4305 of providing (e.g., forming) a second scintillator layer. In these or other embodiments, activity 4305 can be similar to activity 4302. Further, the second scintillator layer can be similar or identical to the first scintillator layer, and/or can be similar to flexible scintillator layer 3302 (FIG. 33). In various embodiments, activity 4305 can comprise an activity of providing the second scintillator layer over (e.g., on) one or more of the first device element(s) (e.g., the photodetector). For example, in some embodiments, the second scintillator layer can directly contact one or more of the first device element(s), the P-type layer, or the photodetector. Accordingly, the first scintillator layer can be coupled to one or more of the first device element(s), the P-type layer, or the photodetector without an adhesive, thereby positioning the second scintillator layer closer to the first device element(s) so that photons emitted by the second scintillator layer can be better detected by one or more of the first device element(s) (e.g., a photodetector). In other embodiments, activity 4305 can be omitted. FIG. 48 illustrates an exemplary activity 4305, according to the embodiment of FIG. 43.

In some embodiments, activity 4305 can comprise activity 4801 of providing one or more second radiation absorbing materials. The second radiation absorbing material(s) can be configured to absorb radiation (e.g., x-ray radiation). In many embodiments, one or more of the first radiation absorbing material(s) and one or more of the second radiation absorbing material(s) can be the same as each other or different from each other.

Although, in some embodiments, the second radiation absorbing material(s) can comprise any material or materials configured to absorb radiation (e.g., x-ray radiation), in many embodiments, the second radiation absorbing material(s) can comprise one or more high atomic number materials. Exemplary second radiation absorbing material(s) can comprise cesium iodide, one or more cesium oxides, one or more dysprosium oxides, one or more gadolinium oxides, one or more lanthanum oxides, one or more yttrium oxides, one or more cesium oxysulfides, one or more dysprosium oxysulfides, one or more gadolinium oxysulfides, one or more lanthanum oxysulfides, one or more yttrium oxysulfides, one or more cesium orthosilicates, one or more dysprosium orthosilicates, one or more gadolinium orthosilicates, one or more lanthanum orthosilicates, and/or one or more yttrium orthosilicates.

In some embodiments, activity 4305 can comprise activity 4802 of providing one or more second phosphorescent materials. The second phosphorescent material(s) can be configured to luminesce. In many embodiments, one or more of the first phosphorescent material(s) and one or more of the second phosphorescent material(s) can be the same as each other or different from each other.

Although, in some embodiments, the second phosphorescent material(s) can comprise any material or materials configured to luminesce, in many embodiments, the second phosphorescent material(s) can comprise one or more rare earth elements. Exemplary second phosphorescent material(s) can comprise cerium, europium, fluorine, praseodymium, sodium, terbium, and/or titanium. In some embodiments, the second phosphorescent material(s) can be selected based on the first device material(s) (e.g., the photodetector) implemented in activity 4304 (FIG. 4). That is, the second phosphorescent material(s) can be selected to tune the light output of the second phosphorescent material(s) to the first device material(s) (e.g., the photodetector) implemented in activity 4304 (FIG. 4).

In some embodiments, the second phosphorescent material(s) can be provided in a powder form. In these or other embodiments, the second phosphorescent material(s) can comprise an average particle diameter. The average particle diameter can be less than or equal to approximately 12 microns.

In many embodiments, activity 4302 can comprise activity 4803 of providing one or more second fluids. The second fluid(s) can comprise deionized water, isopropyl alcohol, one or more surfactants, and one or more binding agents. The surfactant(s) and/or the binding agent(s) implemented can depend on the second radiation absorbing material(s) implemented in activity 4801 and/or the first phosphorescent material(s) implemented in activity 4802. In some embodiments, the binding agent(s) can comprise one or more liquid polymers (e.g., liquid polyimide). In many embodiments, one or more of the first fluid(s) and one or more of the second fluid(s) can be the same as each other or different from each other.

In many embodiments, activity 4305 can comprise activity 4804 of mixing together the second radiation absorbing material(s), the second phosphorescent material(s), and the second fluid(s) to form a second scintillator layer suspension (e.g., slurry). Activity 4804 can be performed after activities 4801-4803.

In many embodiments, activity 4305 can comprise activity 4805 of depositing the second scintillator layer suspension over the first device element(s) (e.g., the photodetector). In some embodiments, the second scintillator layer suspension can be deposited over the first device element(s) (e.g., the photodetector) using any suitable fluid coating technique or techniques (e.g., spray coating, spin coating, slot die coating, curtain coating, ink jet printing, screen printing). Activity 4505 can be performed after activity 4504.

In many embodiments, activity 4305 can comprise activity 4506 of curing the second scintillator layer suspension after the second scintillator layer suspension is deposited over the first device element(s) (e.g., the photodetector). For example, in some embodiments, activity 4305 can comprise an activity of baking (e.g., dehydrating) the second scintillator layer suspension after the second scintillator layer suspension is deposited over the first device element(s) (e.g., the photodetector). The second scintillator layer suspension can be baked at greater than or equal to approximately 50 degrees Celsius and less than or equal to approximately 400 degrees Celsius. Activity 4506 can be performed after activity 4505.

Figure 49:
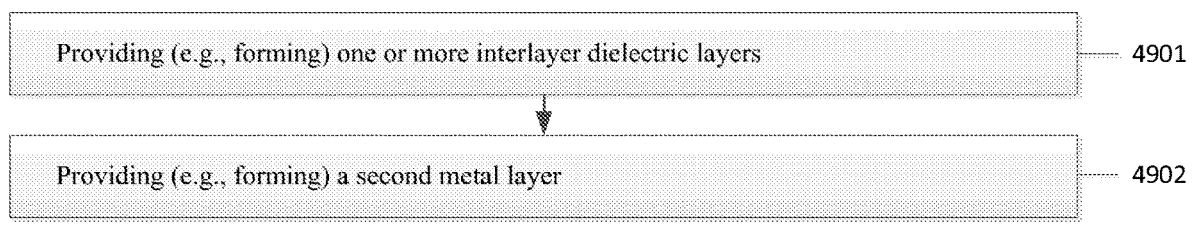
FIG. 49 illustrates an exemplary activity of providing (e.g., forming) one or more second device elements, according to the embodiment of FIG. 43.

Referring back to FIG. 43, in many embodiments, method 4300 can comprise activity 4306 of providing (e.g., forming) one or more second device elements (e.g., over the first device element(s)). In these or other embodiments, the second device element(s) can be provided (e.g., formed) using any suitable semiconductor processing technique or techniques (e.g., photo patterning followed by dry or wet chemical etching, imprinting or embossing, screen or stencil printing, photo patterned lift-off processing, ink jet printing, etc.). In some embodiments, activity 4306 can be similar or identical to part of activity 1121 (FIG. 11). Further, the second device element(s) can be similar or identical to one or more of the semiconductor element(s) described above with respect to activity 1121 (FIG. 11). In various embodiments, activity 4306 can comprise an activity of providing the second device element(s) over (e.g., on) the second scintillator layer, such as, for example, when method 4300 comprises activity 4305. FIG. 49 illustrates an exemplary activity 4306, according to the embodiment of FIG. 43.

For example, in some embodiments, activity 4306 can comprise activity 4901 of providing (e.g., forming) one or more interlayer dielectric layers. In these or other embodiments, performing activity 4306 can be similar or identical to performing one or more of activity 1198 (FIG. 11) and activities 1114-1120 (FIG. 11). Meanwhile, the interlayer dielectric layer(s) can be similar or identical to base dielectric 2499 (FIGS. 24-25 & 32), first dielectric layer 2461 (FIGS. 24-25 & 32) and/or second dielectric layer 2462 (FIGS. 24-25 & 32).

The interlayer dielectric layer(s) can comprise one or more interlayer dielectric layer materials. Exemplary interlayer dielectric layer material(s) can comprise one or more oxides, one or more nitrides, one or more silicon oxynitrides, and/or one or more organic materials. Exemplary organic material(s) can comprise polimide and/or SU-8 epoxy photoresist.

In some embodiments, activity 4306 can comprise activity 4902 of providing (e.g., forming) a second metal layer. In these or other embodiments, performing activity 4902 can be similar or identical to providing the second metal layer as described above with respect to method 100 (FIG. 1) and/or activity 1121 (FIG. 11). Further, the second metal layer can be similar or identical to the second metal layer described above with respect to method 100 (FIG. 1). Further, the second metal layer can be similar or identical to metal layer 2160 (FIGS. 21, 22, 24-26, & 32).

The second metal layer can comprise one or more second metal layer materials. Although, in some embodiments, the second metal layer material(s) can comprise any suitable metal or metals, in many embodiments, the second metal layer material(s) can comprise silicon, phosphorous, boron, aluminum, neodymium, tantalum, chromium, niobium, tin, indium, zinc, molybdenum, titanium, zirconium, and/or hafnium.

Referring again to FIG. 43, in some embodiments, method 4300 can comprise activity 4307 of removing the flexible substrate, the transistor, the first device element(s), the second device element(s), and at least one of the first scintillator layer or the second scintillator layer from the carrier substrate. In these or other embodiments, performing activity 4307 can be similar or identical to removing the flexible substrate, including the semiconductor elements coupled to the flexible substrate, from the carrier substrate as described above with respect to method 100 (FIG. 1). For example, activity 4307 can be similar or identical to activity 130 (FIG. 1).

In some embodiments, an electronic device manufactured using method 4300 can be similar to active matrix pixel array 3301 (FIG. 33) and flexible scintillator layer 3302 (FIG. 33) together. For example, the electronic device can be integrated in an imaging system, and the imaging system can be similar or identical to imaging system 3300 (FIG. 33). However, method 4300 can permit one or more scintillator layers of the electronic device to be processed and/or integrated with a remainder of the electronic device. Meanwhile, the one or more scintillator layers can flex along with the remainder of the electronic device, making the imaging system more flexible than conventional imaging systems.

For example, in some embodiments, method 4300 can permit one or more scintillator layers (e.g., the first scintillator layer of activity 4302 and/or the second scintillator layer of activity 4305) to be processed using conventional semiconductor techniques. Accordingly, the one or more scintillator layers can be fabricated together with one or more other layers of an electronic device manufactured using method 4300.

In these or other embodiments, method 4300 can permit one or more scintillator layers (e.g., the first scintillator layer of activity 4302 and/or the second scintillator layer of activity 4305) to be directly integrated (e.g., monolithically integrated) into an electronic device manufactured using method 4300. That is, the one or more scintillator layers can form a unitary body with part or all of a remainder of the electronic device manufactured using method 4300. For example, in some embodiments, the first scintillator layer of activity 4302 and/or the second scintillator layer of activity 4305 can be monolithically integrated with the substrate assembly of activity 4301, the transistor of activity 4303, the one or more first device elements (e.g., the photodetector) of activity 4304, and/or the one or more second device elements of activity 4306.

In many embodiments, because the one or more scintillator layers can be integrated into the electronic device, scintillator adhesives and thick inflexible backings (e.g., cellulose acetate, polyester, or another polymer) implemented with conventional scintillators (i.e., non-processed and/or non-integrated scintillators) can be eliminated so that an imaging system incorporating an electronic device manufactured by method 4300 can remain as thin, light weight, and/or flexible as possible. Further, because the one or more scintillator layers can be positioned more closely to a photodetector (e.g., photodiode) of an electronic device manufactured by method 4300 as a result of omitting such scintillator adhesives, an imaging system incorporating the electronic device can operate with a higher resolution.

In many embodiments, method 4300 can be implemented with activity 4302 even when part or all of the transistor of activity 4303 is opaque, such as for example, when the first device element(s) of activity 4304 comprise one or more organic materials that may need protection from atmospheric contamination (e.g., contamination by atmospheric gases and/or water), because the transistor can be patterned such that at least part of the photons emitted by the first scintillator layer are able to be received by the first device element(s). For example, in some embodiments, the transistor can block less than or equal to approximately 10 percent of any particular pixel of the first device element(s). In further embodiments, implementing method 4300 with activity 4302 can improve the modulation transfer function (MTF) of an imaging system incorporating an electronic device manufactured by method 100.

In many embodiments, implementing method 4300 with activity 4305 can increase the sensitivity and/or resolution an imaging system incorporating an electronic device manufactured by method 4300 because the second scintillator layer can be positioned in direct contact with one or more of the first device element(s) (e.g., a photodetector). As a result, the first device element(s) can receive more photons emitted by the second scintillator layer, making the imaging system more sensitive, and emitted photons can be detected by the nearest pixels of the first device element(s), mitigating pixel cross-talk and permitting higher resolution imaging. In some embodiments, imaging resolution can be further increased by forming an opaque grid between one or both of the first scintillator layer and/or the second scintillator layer to confine photons emitted by the first scintillator layer and/or the second scintillator layer to the nearest relevant pixel of the first device element(s). Meanwhile, implementing method 4300 with both activity 4302 and activity 4305 can increase a sensitivity and/or a resolution of an imaging system incorporating an electronic device manufactured by method 4300 by permitting radiation to be detected at both (e.g., opposing) sides of the electronic device.

In many embodiments, an imaging system integrating an electronic device manufactured by method 4300 can be portable, flexible, and/or durable. Also, a thickness of the imaging system can be reduced. Accordingly, the imaging system may permit remote analysis of radiographs taken on the battlefield or in limited-infrastructure locales, non-destructive testing of curved objects such as oil pipelines, airframes, and airfoils, and identification of suspicious objects where a fixed detector is impractical. Further, a paramedic can slide the imaging system directly underneath a victim of a car accident at the scene or an inspector can wrap the imaging system around an oil pipeline for non-destructive structural health monitoring. By comparison, ruggedization of a conventional imaging system can increase a thickness of the conventional imaging system by up to approximately 5 centimeters, which may prevent a conventional imaging system from being slid underneath an injured patient who may need to be disturbed as little as possible. Because the imaging system can be made thinner than a conventional imaging system, the imaging system can permit closer contact with test subjects, thus providing higher resolution imaging for imaging techniques such as mammography where better resolution can permit earlier detection of cancerous cells. Further, higher costs associated with ruggedization of conventional imaging systems can be reduced or eliminated by implementing an imaging system integrating an electronic device manufactured by method 4300.

Notably, current digital radiography technology can be classified as direct, where the x-rays are converted directly into an electrical signal in a photoconductor such as amorphous selenium, or indirect, where the incident x-rays are converted into visible light in a scintillator phosphor layer which is then absorbed by a photodiode. In a flexible large area radiography system, direct detectors can be disadvantageous because the amorphous selenium photoconductor can be evaporated to prevent the substrate from melting. As a result of line-of-sight limitations from the evaporation process, the amorphous selenium deposition can be non-uniform. In addition, the amorphous selenium is frequently grown to a thickness of approximately 100 micrometers or greater to allow for sufficient capture and conversion of the incident x-rays, which can impart great stress on the flexible substrate and limit the flexible substrate bending radius of curvature. Accordingly, indirect digital x-ray detectors, such as, for example, an imaging system integrating an electronic device manufactured by method 4300, can be better suited for flexible radiography because the photodiodes can be deposited more uniformly using plasma enhanced chemical vapor deposition (PECVD) and the photodiodes can sufficiently absorb photons emitted by the scintillator phosphor layer down to thickness of approximately 1 micrometer. At a thickness of 1 micrometer, the photodiodes can still impart stress on the flexible substrate, but the effect can be mitigated by patterning the photodiodes. A weakness of conventional indirect radiography systems can be image blurring or cross-talk caused by a separation gap between the scintillator phosphor layer and the photodiodes as many scintillator phosphor layers are constructed separately from a digital x-ray detector backplane. For example, the two-step x-ray conversion process, in which the signal profile is broadened due to optical scatter, can lead to loss of spatial resolution and image degradation due to the lateral spread of optical photons. Integrating the scintillator phosphor layer into one of the device layers of the digital x-ray detector backplane can significantly reduce these issues.

Figure 50:
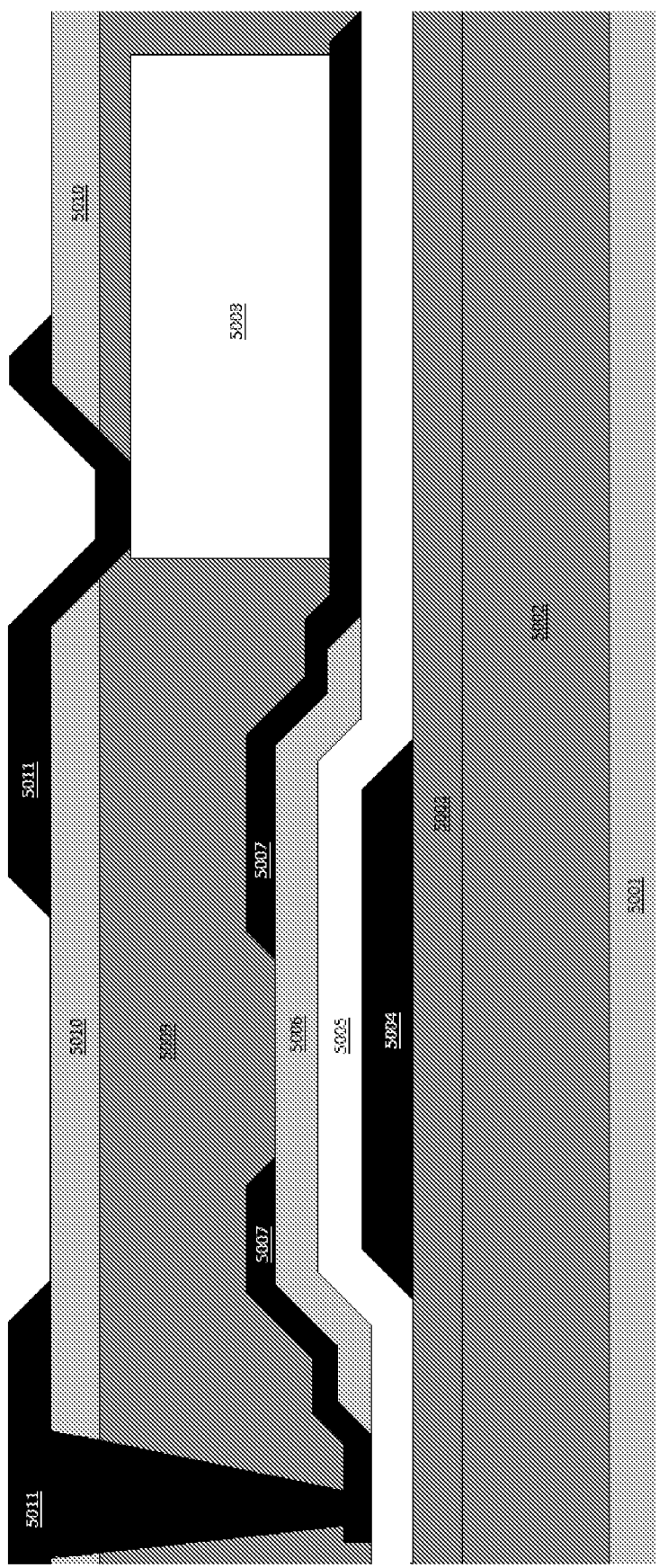
FIG. 50 illustrates a cross-sectional view of a device build area of an electronic device, according to an embodiment.

Turning ahead in the drawings, FIG. 50 illustrates a cross-sectional view of a device build area of an electronic device 5000, according to an embodiment. Electronic device 5000 is merely exemplary and is not limited to the embodiments presented herein. Electronic device 5000 can be employed in many different embodiments or examples not specifically depicted or described herein.

In many embodiments, electronic device 5000 can comprise substrate assembly 5001, first scintillator layer 5002, passivation layer 5003, gate metal layer 5004, gate dielectric layer 5005, patterned active layer 5006, first metal layer 5007, one or more first device elements 5008, second scintillator layer 5009, one or more interlayer dielectric layers 5010, and second metal layer 5011.

In some embodiments, substrate assembly 5001 can be similar or identical to the substrate assembly described above with respect to the substrate assembly described above with respect to activity 4301 (FIG. 43) and/or to substrate assembly 540 (FIGS. 5, 6, & 8-10, 13-22, 24-26, & 32); first scintillator layer 5002 can be similar or identical to the first scintillator layer described above with respect to activity 4302 (FIG. 43); passivation layer 5003 can be similar or identical to the passivation layer described above with respect to activity 4601 (FIG. 46) and/or to passivation layer 1352 (FIGS. 13-22, 24-26, & 32); gate metal layer 5004 can be similar or identical to the gate metal layer described above with respect to activity 4602 (FIG. 46) and/or to gate metal layer 1353 (FIGS. 13-22, 24-26, & 32); gate dielectric layer 5005 can be similar or identical to the gate dielectric layer described above with respect to activity 4603 (FIG. 46) and/or to gate dielectric layer 1554 (FIGS. 15-22, 24-26, & 32); patterned active layer 1555 can be similar or identical to the patterned active layer described above with respect to activity 4604 (FIG. 46) and/or to patterned active layer 1555 (FIGS. 15, 17, 19, 21, 24-26, & 32); first metal layer 5007 can be similar or identical to the first metal layer described above with respect to activity 4606 (FIG. 46) and/or to metal layer 2160 (FIGS. 21, 22, 24-26, & 32); first device element(s) 5008 can be similar or identical to the first device element(s) described above with respect to activity 4304 (FIG. 43); second scintillator layer 5009 can be similar or identical to the second scintillator layer described above with respect to activity 4305 (FIG. 43); interlayer dielectric layer(s) 5010 can be similar or identical to the interlayer dielectric layer(s) described above with respect to activity 4901 (FIG. 49); and/or second metal layer 5011 can be similar or identical to the second metal layer described above with respect to activity 4902 (FIG. 49). In some embodiments, one of first scintillator layer 5002 or second scintillator layer 5009 can be omitted.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that any of the activities of method 100 (FIG. 1), method 2700 (FIG. 27), method 3500 (FIG. 35), method 4000 (FIG. 40), and/or method 4300 (FIG. 43) may be comprised of many different activities and be performed by many different modules, in many different orders, that any element of FIGS. 1-50 may be modified, and that the foregoing discussion of certain of these embodiments does not necessarily represent a complete description of all possible embodiments.

Generally, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are expressly stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An electronic device comprising:
a first scintillator layer;
a transistor;
one or more device elements over the transistor; and
a substrate assembly;
wherein:
the one or more device elements comprise a photodetector;
the first scintillator layer is monolithically integrated with at least one of the transistor or the one or more device elements;
the transistor is over the substrate assembly;
the substrate assembly comprises a carrier substrate; and
the first scintillator layer is over the substrate assembly and under the transistor.

2. The electronic device of claim 1 wherein:
the first scintillator layer directly contacts the photodetector.

3. The electronic device of claim 1 wherein:
the first scintillator layer directly contacts at least one of the substrate assembly or the transistor.

4. The electronic device of claim 1 further comprising:
a second scintillator layer;
wherein:
the second scintillator layer directly contacts the photodetector.

5. The electronic device of claim 4 wherein:
the second scintillator layer is monolithically integrated with the transistor and the one or more device elements.

6. The electronic device of claim 1:
wherein:
the substrate assembly further comprises a flexible substrate.

7. The electronic device of claim 4 wherein:
the first scintillator layer directly contacts at least one of the substrate assembly or the transistor;

the second scintillator layer is monolithically integrated with the transistor and the one or more device elements; and
the substrate assembly further comprises a flexible substrate.

8. A method of manufacturing an electronic device, the method comprising:
providing a first scintillator layer;
providing a substrate assembly comprising a carrier substrate;
providing a transistor over the substrate assembly; and
providing one or more device elements over the transistor;
wherein:
providing the one or more device elements comprises:
providing a photodetector;
the first scintillator layer is monolithically integrated with at least one of the transistor or the one or more device elements; and
the first scintillator layer directly contacts at least one of the substrate assembly or the transistor.

9. The method of claim 8 wherein:
providing the first scintillator layer comprises:
forming the first scintillator layer such that the first scintillator layer directly contacts the photodetector.

10. The method of claim 8 further comprising:
wherein:
the substrate assembly further comprises:
a flexible substrate.

11. The method of claim 8 wherein:
providing the first scintillator layer comprises at least one of:
forming the first scintillator layer such that the first scintillator layer is over the substrate assembly and under the transistor.

12. The method of claim 8 further comprising:
providing a second scintillator layer;
wherein:
providing the second scintillator layer comprises:
forming the second scintillator layer such that the second scintillator layer directly contacts the photodetector.

13. The method of claim 12 wherein:
the first scintillator layer is monolithically integrated with the transistor and the one or more device elements; and
the second scintillator layer is monolithically integrated with the transistor and the one or more device elements.

14. The electronic device of claim 8 wherein:
the substrate assembly further comprises a flexible substrate; and
providing the first scintillator layer comprises forming the first scintillator layer such that the first scintillator layer is over the substrate assembly and under the transistor.

15. An electronic device comprising:
a substrate assembly comprising a carrier substrate and a flexible substrate coupled to the carrier substrate;
a transistor over the substrate assembly;
one or more device elements over the transistor, the one or more device elements comprising a photodetector; and
a first scintillator layer over the one or more device elements, the first scintillator layer comprising one or more first radiation absorbing materials and one or more first phosphorescent materials;
wherein:
the first scintillator layer directly contacts the photodetector; and the first scintillator layer is monolithically integrated with the transistor and the photodetector.

16. The electronic device of claim 15 wherein:
the first scintillator layer directly contacts at least one of the substrate assembly or the transistor.

17. The electronic device of claim 15 further comprising:
a second scintillator layer;
wherein:
   the second scintillator layer directly contacts the photodetector.

18. The electronic device of claim 17 wherein:
the second scintillator layer is monolithically integrated with the transistor and the one or more device elements.

19. The electronic device of claim 15 wherein:
the substrate assembly further comprises a carrier substrate.

20. The electronic device of claim 15 wherein:
the first scintillator layer directly contacts at least one of the substrate assembly or the transistor; and
the substrate assembly further comprises a carrier substrate.

* * * * *